(12) United States Patent
Qian et al.

(10) Patent No.: US 10,738,093 B2
(45) Date of Patent: Aug. 11, 2020

(54) DISCOVERY OF CATIONIC NONRIBOSOMAL PEPTIDES AS GRAM-NEGATIVE ANTIBIOTICS THROUGH GLOBAL GENOME MINING

(71) Applicants: The Hong Kong University of Science and Technology, Hong Kong (CN); China Ocean Mineral Resources R&D Association (COMRA), Beijing (CN)

(72) Inventors: Pei-Yuan Qian, Hong Kong (CN); Yongxin Li, Hong Kong (CN); Zheng Zhong, Hong Kong (CN); Weipeng Zhang, Hong Kong (CN)

(73) Assignees: The Hong Kong University of Science and Technology, Hong Kong (CN); China Ocean Mineral Resources R&D Assocation (COMRA), Beijing (CN)

( * ) Notice: Subject to any disclaimer, the term of this patent is extended or adjusted under 35 U.S.C. 154(b) by 0 days.

(21) Appl. No.: 16/255,287

(22) Filed: Jan. 23, 2019

(65) Prior Publication Data
US 2019/0225663 A1 Jul. 25, 2019

Related U.S. Application Data

(60) Provisional application No. 62/621,929, filed on Jan. 25, 2018.

(51) Int. Cl.
| | | |
|---|---|---|
| *A61K 38/00* | (2006.01) | |
| *A61K 38/04* | (2006.01) | |
| *A61P 31/04* | (2006.01) | |
| *C07K 14/47* | (2006.01) | |
| *C07K 14/345* | (2006.01) | |

(52) U.S. Cl.
CPC .......... *C07K 14/4723* (2013.01); *A61K 38/04* (2013.01); *A61P 31/04* (2018.01); *C07K 14/345* (2013.01); *A61K 38/00* (2013.01)

(58) Field of Classification Search
CPC ......... A61K 38/00; A61K 38/04; A61P 31/04; C07K 14/435; C07K 14/4723; C07K 14/47
USPC ........... 514/1.1, 2.3, 2.4, 2.8, 21.5; 530/300, 530/327, 319
See application file for complete search history.

(56) References Cited

U.S. PATENT DOCUMENTS

| | | | |
|---|---|---|---|
| 3,595,956 A * | 7/1971 | Florestano | A01N 31/08 514/2.9 |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |

OTHER PUBLICATIONS

Hancock et al., "Peptide Antibiotics," Antimicrobial Agents and Chemotherapy, 43(6): 1317-1323. (Year: 1999).*
Tsubery et al., "Structure-Function Studies of Polymyxin B Nonapeptide: Implications to Sensitization of Gram-Negative Bacteria," J. Med. Chem., 43: 3085-3092. (Year: 2000).*
Hydrochloric Acid from ChemicalSafetyFacts.org, pp. 1-2. Accessed Feb. 3, 2020. (Year: 2020).*
Blin, K. et al., "The antiSMASH database, a comprehensive database of microbial secondary metabolite biosynthetic gene clusters," *Nucleic Acids Research*, 2017, 45:D555-D559.
Bode, H. B., "Entomopathogenic bacteria as a source of secondary metabolites," *Current Opinion in Chemical Biology*, 2009, 13:224-230, Elsevier Ltd.
Boucher, H. W. et al., "Bad Bugs, No Drugs: No ESKAPE! An Update from the Infectious Diseases Society of America," *Clinical Infectious Diseases*, Jan. 1, 2009, 48:1-12, Infectious Diseases Society of America.
Chu, J. et al., "Discovery of MRSA active antibiotics using primary sequence from the human microbiome," *Nat Chem Biol.* Dec. 2016, 12(12):1-12.
Clardy, J. et al., "New antibiotics from bacterial natural products," *Nature Biotechnology*, Dec. 2006, 24(12):1541-1550, Nature Publishing Group.
Cochrane, S. A. et al., "Lipopeptides from *Bacillus* and *Paenibacillus* spp.: A Gold Mine of Antibiotic Candidates," *Medicinal Research Reviews*, 2016, 36(1):4-31, 2014 Wiley Periodicals, Inc.
Cochran, S. A. et al., "Antimicrobial lipopeptide tridecaptin $A_1$ selectively binds to Gram-negative lipid II," *Proceedings of the National Academy of Sciences*, Oct. 11, 2016, 113(41):11561-11566.
Crosa, J. H. et al., "Genetics and Assembly Line Enzymology of Siderophore Biosynthesis in Bacteria," *Microbiology and Molecular Biology Reviews*, Jun. 2002, 66(2):223-249, American Society for Microbiology.
Deryke, C. A. et al., "Bactericidal Activities of Meropenem and Ertapenem against Extended-Spectrum-β-Lactamase-Producing *Escherichia coli* and *Klebsiella pneumoniae* in a Neutropenic Mouse Thigh Model," *Antimicrobial Agents and Chemotherapy*, Apr. 2007, 51(4)1148-11486, American Society for Microbiology.

(Continued)

*Primary Examiner* — Julie Ha
(74) *Attorney, Agent, or Firm* — Saliwanchik, Lloyd & Eisenschenk

(57) ABSTRACT

Pharmacological compositions comprising a cationic nonribosomal peptide (CNRP) or a salt thereof are described. Further, methods of treating a bacterial infection in a subject by administering to the subject a CNRP or a salt thereof are provided.

6 Claims, 40 Drawing Sheets
Specification includes a Sequence Listing.

(56) References Cited

OTHER PUBLICATIONS

Epand, R. M. et al., "Diversity of antimicrobial peptides and their mechanisms of action," *Biochimica et Biophysica Acta*, 1999, 1462:11-28, Elsevier Science B.V.

Fischbach, M. A. et al., "Antibiotics for Emerging Pathogens," *Science*, Aug. 28, 2009, 325(5944):1089-1093.

Fjell, C. D. et al., "Designing antimicrobial peptides: form follows function," *Nature Reviews*, Jan. 2012, 11:37-51, Macmillan Publishers Limited.

Forst, S. et al., "*Xenorhabdus* and *Photorhabdus* spp.: Bugs That Kill Bugs," *Annu. Rev. Microbiol.*, 1997, 51:47-72, Annual Reviews Inc.

Fuchs, S. W. et al., "Neutral Loss Fragmentation Pattern Based Screening for Arginine-Rich Natural Products in *Xenorhabdus* and *Photorhabdus*," Aug. 6, 2012, 84:6948-6955, American Chemical Society.

Gerlt, J. A. et al., "Enzyme Function Initiative-Enzyme Similarity Tool (EFI-EST): A web tool for generating protein sequence similarity networks," *Biochim Biophys Acta.*, Aug. 2015, 1854(8):1019-1037, Elsevier B.V.

Gordan, Y. J. et al., "A Review of Antimicrobial Peptides and Their Therapeutic Potential as Infective Drugs," *Current Eye Research*, 2005, 30:505-515, Taylor & Francis Group.

Gross, H. et al., "Genomics of secondary metabolite production by *Pseudomonas* spp †," *Natural Product Reports*, 2009, 26:1408-1446, The Royal Society of Chemistry.

Hancock, R. E. W. et al., "Antimicrobial and host-defense peptides as new anti-infective therapeutic strategies," *Nature Biotechnology*, Dec. 11, 2016, 24(12):1551-1557, Nature Publishing Group.

Hancock, R. E. W. et al., "Cationic peptides: a new source of antibiotics," *Tibtech*, Feb. 1998, 16:82-88, Elsevier Science Ltd.

Huang, E. et al., "The Lipopeptide Antibiotic Paenibacterin Binds to the Bacterial Outer Membrane and Exerts Bactericidal Activity through Cytoplasmic Membrane Damage," *Applied and Environmental Microbiology*, May 2014, 80(9):2700-2704, American Society for Microbiology.

Kosikowska, P. et al., "Antimicrobial peptides (AMPs) as drug candidates: a patent review (2003-2015)," *Expert Opinion on Therapeutic Patents*, 2016, 26(6):689-702, Taylor & Francis Group.

Law, V. et al., "DrugBank 4.0: shedding new light on drug metabolism," *Nucleic Acids Research*, Nov. 6, 2013, 42:D1091-D1097, Oxford University Press.

Laxminarayan, R. et al., "Antibiotic resistance—the need for global solutions," *The Lancet Infectious Diseases Commission*, Dec. 2013, 13:1057-1098.

Lewis, K., "Platforms for antibiotic discovery," *Nature Reviews*, May 2013, 12:371-387, Macmillan Publishers Limited.

Li, Y. et al., "Resistance to nonribosomal peptide antibiotics mediated by D-stereospecific peptidases," *Nature Chemical Biology*, Apr. 2018, 14:381-387, Nature America Inc., part of Springer Nature.

Labler, L. et al., "The use of vacuum assisted closure (VAC™) in soft tissue injuries after high energy pelvic trauma," *Langenbecks Arch Surg*, 2007, 392:601-609, Springer-Verlag 2006.

Li, Y. et al., "Discovery of cationic nonribosomal peptides as Gram-negative antibiotics through global genome mining," *Nature Communications*, 2018, 9:1-9.

Mahlapuu, M. et al., "Antimicrobial Peptides: An Emerging Category of Therapeutic Agents," *Frontiers in Cellular and Infection Microbiology*, Dec. 27, 2016, 6(194):1-12.

Marr, A. K. et al., "Antibacterial peptides for therapeutic use: obstacles and realistic outlook," *Current Opinion in Pharmacology*, 2006, 6:468-472, Elsevier Ltd.

Moon, S. H. et al., "Novel Linear Lipopeptide Paenipeptins with Potential for Eradicating Biofilms and Sensitizing Gram-Negative Bacteria to Rifampicin and Clarithromycin," *Journal of Medicinal Chemistry*, Nov. 14, 2017, 60:9630-9640, American Chemical Society.

Garber, J.C. et al., "Guide for the Care and Use of Laboratory Animals," *National Research Council of the National Academies*, 2011, 246 pages, National Academy of Sciences.

Odds, F.C., "Synergy, antagonism, and what the chequerboard puts between them," *Journal of Antimicrobial Chemotherapy*, Jun. 12, 2003, 52:1, The British Society for Antimicrobial Chemotherapy.

Schwarzer, D. et al., "Nonribosomal peptides: from genes to products," *Natural Product Reports*, Mar. 10, 2003, 20:275-287, The Royal Society of Chemistry.

Smoot, M. E. et al., "Cytoscape 2.8: new features for data integration and network visualization," *Systems biology*, Dec. 12, 2010, 27(3):431-432, Oxford University Press.

Trimble, M. J. et al., "Polymyxin: Alternative Mechanisms of Action and Resistance," *Cold Spring Harbor Perspectives in Medicine*, 2016, 6:1-22, Cold Spring Harbor Laboratory Press.

Vaara, M. et al., "A Novel Polymyxin Derivative That Lacks the Fatty Acid Tail and Carries Only Three Positive Charges Has Strong Synergism with Agents Excluded by the Intact Outer MembraneV," *Antimicrobial Agents and Chemotherapy*, Aug. 2010, 54(8):3341-3346, American Society for Microbiology.

Weber, T. et al., "antiSMASH 3.0—a comprehensive resource for the genome mining of biosynthetic gene clusters," *Nucleic Acids Research*, 2015, 43:W237-W243, Oxford University Press on behalf of Nucleic Acids Research.

Yeung, A. T. Y. et al., "Multifunctional cationic host defence peptides and their clinical applications," *Cellular and Molecular Life Sciences*, May 15, 2011, 68:2161-2176, Springer Basel AG.

Liu, Y. et al., "Emergence of plasmid-mediated colistin resistance mechanism MCR-1 in animals and human beings in China: a microbiological and molecular biological study," *Lancet Infect Dis*, Feb. 2016, 16:161-168.

Fujii, K. et al., "A Nonempirical Method Using LC/MS for Determination of the Absolute Configuration of Constituent Amino Acids in a Peptide: Combination of Marfey's Method with Mass Spectrometry and Its Practical Application," *Analytical Chemistry*, Dec. 15, 1997, 69(24):5146-5151, American Chemical Society.

Garber, J. C. et al., "Guide for the Care and Use of Laboratory Animals," *National Research Council of the National Academies*, 2011, p. 1-246, National Academy of Sciences.

Stokes, J. M. et al., "Pentamidine sensitizes Gram-negative pathogens to antibiotics and overcomes acquired colistin resistance," *Nature Microbiology*, Mar. 6, 2017, 2(17028):1-8, Macmillan Publishers Limited, part of Springer Nature.

\* cited by examiner

| Amino Acid Residue | 1 | | 6 | | 7 | | 4 | | Configuration |
|---|---|---|---|---|---|---|---|---|---|
| | D-FDLA (D) | L-FDLA (L) | D | L | D | L | D | L | |
| Asn1 | 10.4 | 10.8 | 10.4 | 10.8 | - | - | | | D |
| Tyr2(di) | 15.2 | 16.1 | 15.2 | 16.1 | - | - | | | D |
| Trp3 | 12.7, 13.2 | 12.7, 13.2 | 12.7 | 13.2 | | | | | D |
| Trp8 | | | | | | | 13.2 | 12.7 | L |
| Orn4 | 8.6, 9.2 | 8.6, 9.2 | 9.2 | 8.6 | | | | | D |
| Orn5 | | | | | 8.6, 9.2 | 8.6, 9.2 | | | L |
| Orn7 | | | | | | | | | D |
| Thr9 | 11.2 | 10.3 | | | | | 11.2 | 10.3 | L |
| Ile10 | 14.5 | 12.6 | | | | | 14.5 | 12.6 | L |
| Ser12 | 10.7 | 10.4 | | | | | 10.7 | 10.4 | L |

Figure 9c

— 1H-1H COSY    ⁀ HMBC

| Amino Acid Residue | 2 D-FDLA (D) | 2 L-FDLA (L) | 10 D | 10 L | 7 D | 7 L | 8 D | 8 L | Configuration |
|---|---|---|---|---|---|---|---|---|---|
| Ser₁ | 10.4, 10.6 | 10.6 | 10.4 | 10.6 | - | - |  |  | D |
| Tyr₂(di) | 15.1, 15.6, 15.9 | 15.9 | 15.1, 15.6, 15.9 | 15.9 | - | - |  |  | D |
| Trp₃ | 12.7, 13.2 | 12.7, 13.2 |  |  |  |  |  |  | D |
| Trp₆ |  |  |  |  |  |  |  |  | L |
| Orn₄ | 8.6, 9.2 | 8.6, 9.2 | 8.6, 9.2 | 8.6 |  |  |  |  | D |
| Orn₅ |  |  |  |  | 8.6, 9.2 | 8.6, 9.2 |  |  | L |
| Orn₇ |  |  |  |  |  |  |  |  | D |
| Thr₉ | 11.4, 10.3 | 10.3 |  |  |  |  | 11.4, 10.3 | 10.3 | L |
| Ile₁₀ | 14.4, 12.5 | 12.5 |  |  |  |  | 14.4, 12.5 | 12.5 | L |
| Asn₁₁ | 10.8, 10.5 | 10.5 |  |  |  |  | 10.8, 10.5 | 10.5 | L |

| Compound | Human HeLa cells (HL60) $IC_{50}$ (µg mL$^{-1}$) |
|---|---|
| brevicidine | >128 |
| laterocidine | >128 |
| bogorol | <8 |

```
                    SEQUENCE LISTING

<160> NUMBER OF SEQ ID NOS: 2

<210> SEQ ID NO 1
<211> LENGTH: 12
<212> TYPE: PRT
<213> ORGANISM: Brevibacillus laterosporus
<220> FEATURE:
<221> NAME/KEY: misc_feature
<222> LOCATION: (1)..(1)
<223> OTHER INFORMATION: Asparagine is D-asparagine
<220> FEATURE:
<221> NAME/KEY: misc_feature
<222> LOCATION: (1)..(1)
<223> OTHER INFORMATION: Asparagine is connected to 4-Methyl-Hexanal
<220> FEATURE:
<221> NAME/KEY: misc_feature
<222> LOCATION: (2)..(2)
<223> OTHER INFORMATION: Tyrosine is D-tyrosine
<220> FEATURE:
<221> NAME/KEY: misc_feature
<222> LOCATION: (3)..(3)
<223> OTHER INFORMATION: Tryptophan is D-Tryptophan
<220> FEATURE:
<221> NAME/KEY: misc_feature
<222> LOCATION: (4)..(4)
<223> OTHER INFORMATION: Xaa is D-ornithine
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (7)..(7)
<223> OTHER INFORMATION: Xaa is D-ornithine
<220> FEATURE:
<221> NAME/KEY: misc_feature
<222> LOCATION: (9)..(9)
<223> OTHER INFORMATION: lactone formation between Thr and the
      C-terminus

<400> SEQUENCE: 1

Asn Tyr Trp Xaa Xaa Gly Xaa Trp Thr Ile Gly Ser
1               5                   10

<210> SEQ ID NO 2
<211> LENGTH: 13
<212> TYPE: PRT
<213> ORGANISM: Brevibacillus laterosporus
<220> FEATURE:
<221> NAME/KEY: misc_feature
<222> LOCATION: (1)..(1)
<223> OTHER INFORMATION: Serine is D-serine
<220> FEATURE:
<221> NAME/KEY: misc_feature
<222> LOCATION: (1)..(1)
<223> OTHER INFORMATION: Serine is connected to 7-Methyl-Octanal
```

```
<220> FEATURE:
<221> NAME/KEY: misc_feature
<222> LOCATION: (2)..(2)
<223> OTHER INFORMATION: Tyrosine is D-tyrosine
<220> FEATURE:
<221> NAME/KEY: misc_feature
<222> LOCATION: (3)..(3)
<223> OTHER INFORMATION: Tryptophan is D-Tryptophan
<220> FEATURE:
<221> NAME/KEY: misc_feature
<222> LOCATION: (4)..(4)
<223> OTHER INFORMATION: Xaa is D-ornithine
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (7)..(7)
<223> OTHER INFORMATION: Xaa is D-ornithine
<220> FEATURE:
<221> NAME/KEY: misc_feature
<222> LOCATION: (9)..(9)
<223> OTHER INFORMATION: lactone formation between Thr and the
      C-terminus

<400> SEQUENCE: 2

Ser Tyr Trp Xaa Xaa Gly Xaa Trp Thr Ile Asn Gly Gly
1               5                   10
```

DISCOVERY OF CATIONIC NONRIBOSOMAL PEPTIDES AS GRAM-NEGATIVE ANTIBIOTICS THROUGH GLOBAL GENOME MINING

CROSS-REFERENCE TO RELATED APPLICATION

This application claims the benefit of U.S. Provisional Patent Application Ser. No. 62/621,929, filed Jan. 25, 2018, which is hereby incorporated by reference in its entirety, including any tables, figures, or drawings.

BACKGROUND OF THE INVENTION

Infection caused by multidrug-resistant Gram-negative bacteria has become a major threat to public health. Over the last 40 years, no truly novel class of antibiotics against Gram-negative bacteria has been introduced to the market. This, coupled with emergence of antibiotic resistance highlights the urgent need for new antibiotics. Cationic peptides represent a huge family of antibiotics and have attracted extensive interest with their diverse chemical structures and great potential for combating Gram-negative pathogens. Cationic nonribosomal peptides, including polymyxins and gramicidin S, are the most structurally diverse families of cationic peptides with great antimicrobial potential.

Cationic peptides are found in all forms of life (mammals, plants, and bacteria), and are among the most widespread and structurally-diverse antibiotics in nature. Carrying unique chemical properties that not only facilitate their penetration through the highly impermeable outer membrane of Gram-negative bacteria but also enable their interaction with multiple anionic intracellular targets, cationic peptides are highly effective against drug-resistant Gram-negative pathogens. In the past four decades, thousands of cationic peptides with broad antimicrobial activities have been identified and most of them are natural or naturally derived host defense peptides from multicellular organisms. However, only a handful of these cationic peptides have entered clinical application, due to their high cost of supply, instability to proteolytic degradation, and unknown toxicological profile. Bacterial cationic nonribosomal peptides (CNRPs) with sufficient supply and proteolytic stability are attractive therapeutic candidates. Polymyxins and gramicidin S produced by bacilli bacteria are among the few precedents with clinical efficacy. However, the diversity and complexity of CNRPs have made systematic investigation difficult and consequently, the vast majority of genetically encoded CNRPs in bacteria have been overlooked and remain unknown.

BRIEF SUMMARY OF THE INVENTION

This disclosure provides a global genome mining of CNRPs from 7,395 bacterial genomes to investigate their biosynthesis capacity and facilitate genome-guided discovery of antibacterial peptides, particularly, against Gram-negative bacteria. The disclosure also provides two novel peptides (brevicidine and laterocidine) with strong antibacterial activity, particularly, against Gram-negative bacteria. Brevicidine and laterocidine exhibit high efficacy in animal model and a low risk of resistance.

The disclosure further provides enterocidines designed using the predicted primary peptide sequence as a potential adjuvant for antibiotics that potentiate conventional Gram-positive antibiotics against Gram-negative pathogens. Thus, the disclosure describes a global genome mining platform to provide insight into the biosynthesis capacity of CNRPs and facilitate the genome-guided discovery antimicrobials, such as antibiotics against Gram-negative bacteria (FIG. 4).

BRIEF DESCRIPTION OF THE DRAWINGS

FIG. 2a Three gene clusters for investigated cationic peptides, with amino acids incorporated. Cationic residues are marked in grey. FIG. 2b Structure of isolated cationic peptides identified by MS/NMR analysis.

FIG. 3a Time-kill assays. E. coli cells were grown to early phase and challenged with 10 times the MIC of antibiotics. Data are representative of three independent experiments±s.d. FIG. 3b Bacterial growth kinetics. Optical densities of E. coli cells exposed to two times the MIC of antibiotics. FIG. 3c CNRPs treatment resulted in the lysis of E. coli. The figure is representative of three independent experiments. FIG. 3d Resistance acquisition during serial passaging in the presence of sub-MIC levels of antimicrobials. FIG. 3e Atomic force microscopy of E. coli grown at 37° C. to mid-log phase (OD of ~0.5) in the presence of 10 times the MIC of CNRP antibiotics. The white box highlights the region scanned to obtain high-resolution topographical images of the brevicidine-treated cell surface. Scans are representative of two independent experiments. FIG. 3f Efficacy of brevicidine and laterocidine in a mouse thigh model using E. coli infection. Brevicidine (30 mg/kg) or laterocidine (15 mg/kg) treatment (2 times) of E. coli thigh infections (5 mice) leads to reduced numbers of viable bacteria after 26 h. Significant differences between groups analyzed by the Mann-Whitney test (*P<0.01). For a-f, con: negative control, bre: brevicidine, lat: laterocidine, ply: polymyxin, lev: levofloxacin, and cfp: ciprofloxacin.

FIG. 5a Global BGCs analysis of bacteria complete genomes (5,585) revealed that CNRPs were abundantly distributed in Proteobacteria, Actinobacteria, and Firmicutes. FIG. 5b The wide distribution of CNRP BGCs at the genus level. To further investigate the biosynthesis capacity of CNRPs, 1810 draft genomes from top 20 abundant genera were also selected for BGCs analysis. CNRP BGCs obtained from 7,395 bacterial genomes were filtered and subjected to sequence similarity study as showed in FIG. 1.

FIG. 6a The diversity of CNRPs in terms of peptide length. The length of CNRPs (n=1,818) varied from 2 to 34, with an average of 6.6 and a median of 5, which indicated their high diversity. Below the dotted line (length≥6) are CNRPs (n=817) that exist in the similarity network in FIG. 1. These CNRPs have an average length of 9.7 and a median length of 9. FIG. 6b The diversity of CNRPs in positively-charged residues percentage. The percentage of positively-charged residues arranged from 6.3% to 78.6% with an average of 33.0% (median 30.0%).

FIGS. 9a-9c show MS, NMR and Marfey-type analyses of brevicidine (1). FIG. 9a $MS_n$ analysis of 1. FIG. 9b The key $^1H$-$^1H$-COSY and $^1H$-$^{13}C$-HMBC correlation of compounds 1. FIG. 9c Marfey-type analysis of brevicidine (Retention times (in min) of 1 constituent amino acid derivatized with D/L-FDLA). The $^1H$, $^1H$-$^1H$-COSY, $^1H$-$^{13}C$-HSQC, and $^1H$-$^{13}C$-HMBC NMR data of 1 were recorded on a Bruker AV500 spectrometer (500 MHz) using DMSO-$d_6$ (1H-NMR MeOH-$d_4$: δ=3.31 ppm; DMSO-$d_6$: δ=2.50 ppm; $^{13}C$-NMR: MeOH-$d_4$: δ=49.00 ppm; DMSO-$d_6$: δ=39.8 ppm). Compound 1 was obtained as a white amorphous solid. Based on HRESIMS data (m/z: 760.4046 [M+2H]$^{2+}$, calc 760.4064 m/z: 507.2729 [M+3H]$^{3+}$, calc 507.2734), its molecular formula was established as $C_{74}H_{106}N_{18}O_{17}$. The characteristic signals of the amide NH and α-amino proton in the $^1H$ NMR spectrum and carbonyl groups in the $^{13}C$ NMR spectrum (FIG. 20) indicated the peptidic nature of the compound. The gross structure of 1 was further established by analyses of the $^1H$, $^{13}C$, $^1H$-$^1H$ COSY, HMQC, and HMBC NMR spectral data (FIGS. 9b and 20), revealing the presence in its structure of Orn (3), Trp (2), Gly (2), Ile (1), Ser (1), Thr (1), Asn(1), Tyr (1) and a lipidic residue that was identified as 4-methylhexanoic acid. The gross structure established by NMR analysis was also corroborated by MS/MS analysis (FIG. 9a).

Figure 12A:
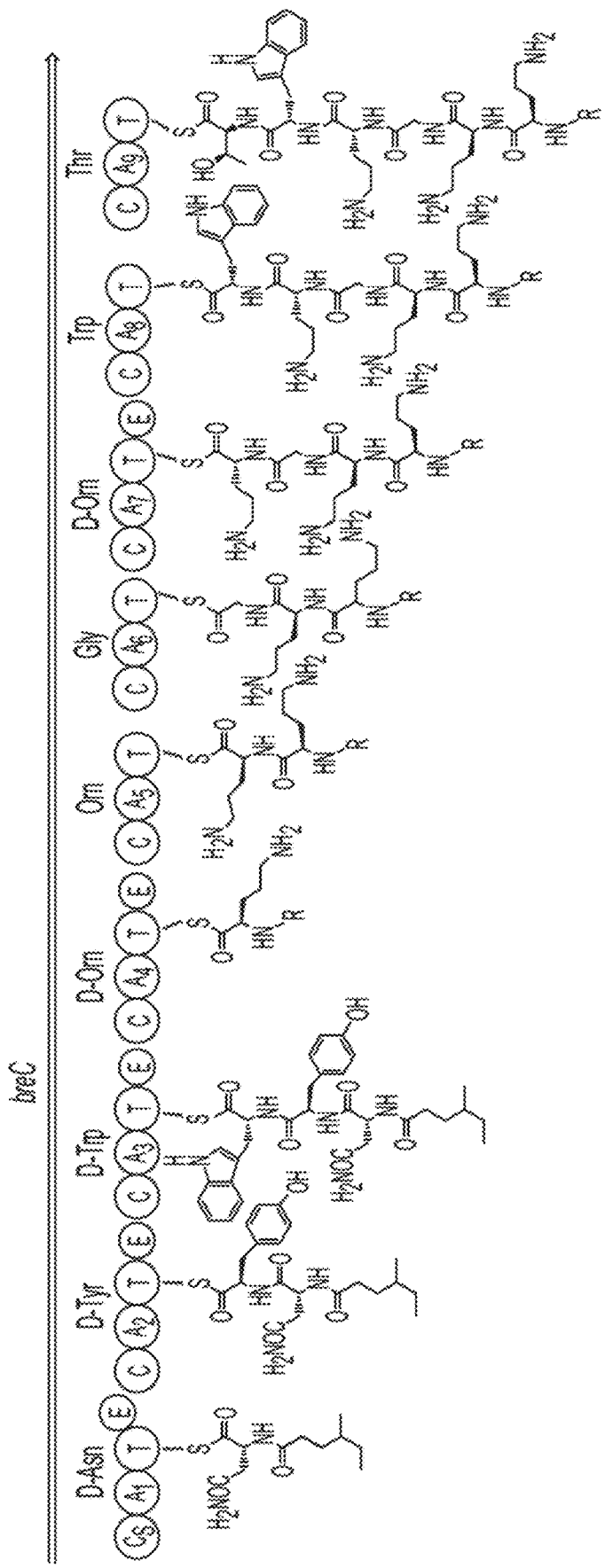
Figure 12B:
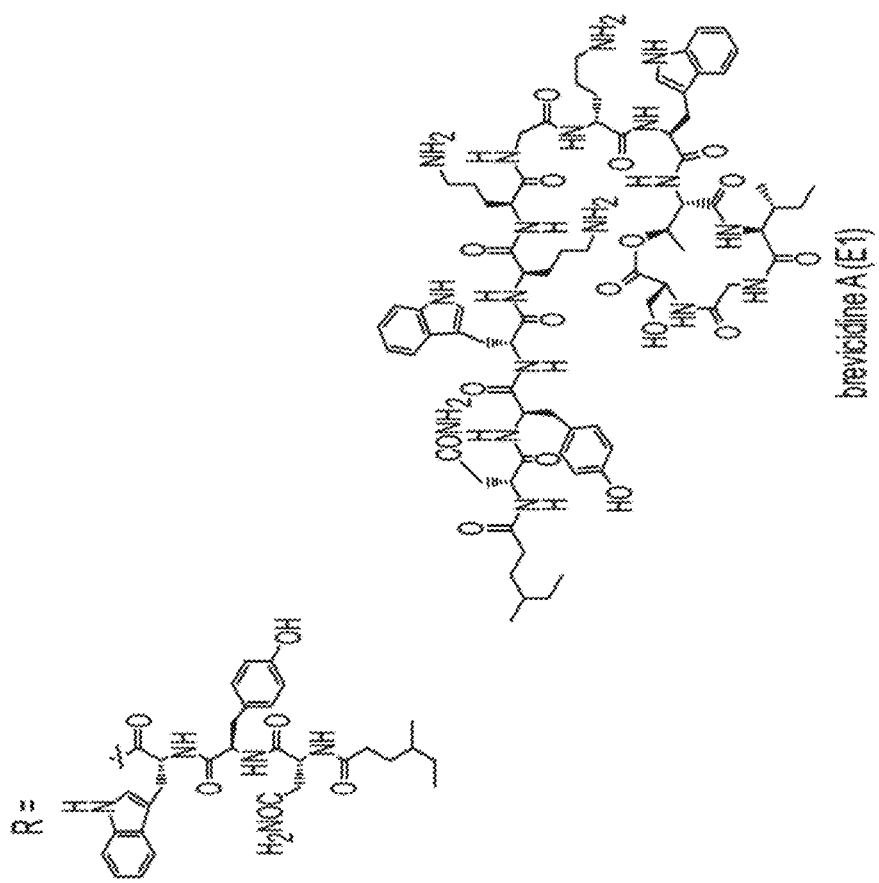
Figure 12B:
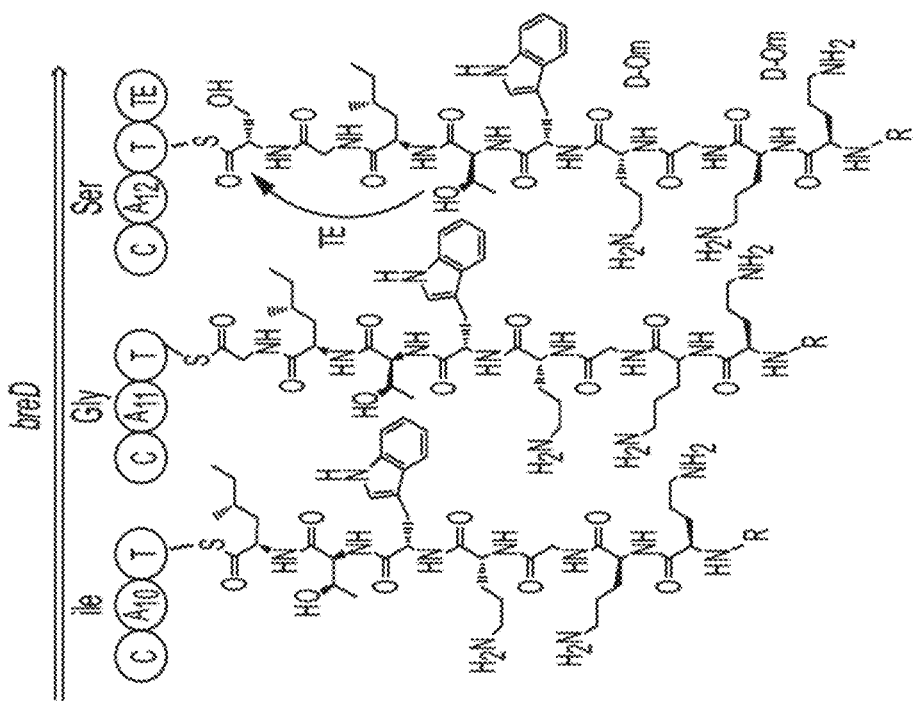

Amino acid configurations of 1 were determined using the advanced Marfey's method. The compound 1 and its hydrolytic products 4, 6 and 7 (0.1-0.2 mg) were hydrolyzed in 6 M HCl at 110° C. overnight. Each solution was evaporated to dryness and the residue was dissolved in 100 μL water and divided into two portions. Each portion was treated with 20 μL NaHCO$_3$ (1M) and 50 μL 1-fluoro-2,4-dinitrophenyl-5-L-leucinamide (L-FDLA) or D-FDLA (1M) at 40° C. for 2 h. The reaction was quenched with 5 μL HCl (1M) and diluted with 200 μL MeOH. The stereochemistry was determined by comparison of the L-/D FDLA derivatized samples using UPLC-MS analysis. On the basis of the combination of the data generated by advanced Marfey's analysis of four compounds, a lipodepsipeptide 4-Methyl-Hexanoyl-D-Asn-D-Tyr-D-Trp-D-Orn-Orn-Gly-D-Orn-Trp-Thr-Ile-Gly-Ser (cyclized via lactone formation between Thr and the C-terminus) was established for the natural product brevicidine. The structure of 1 is consistent with prediction based on biosynthetic pathway analysis (FIGS. 12a-12b).

Figure 10A:
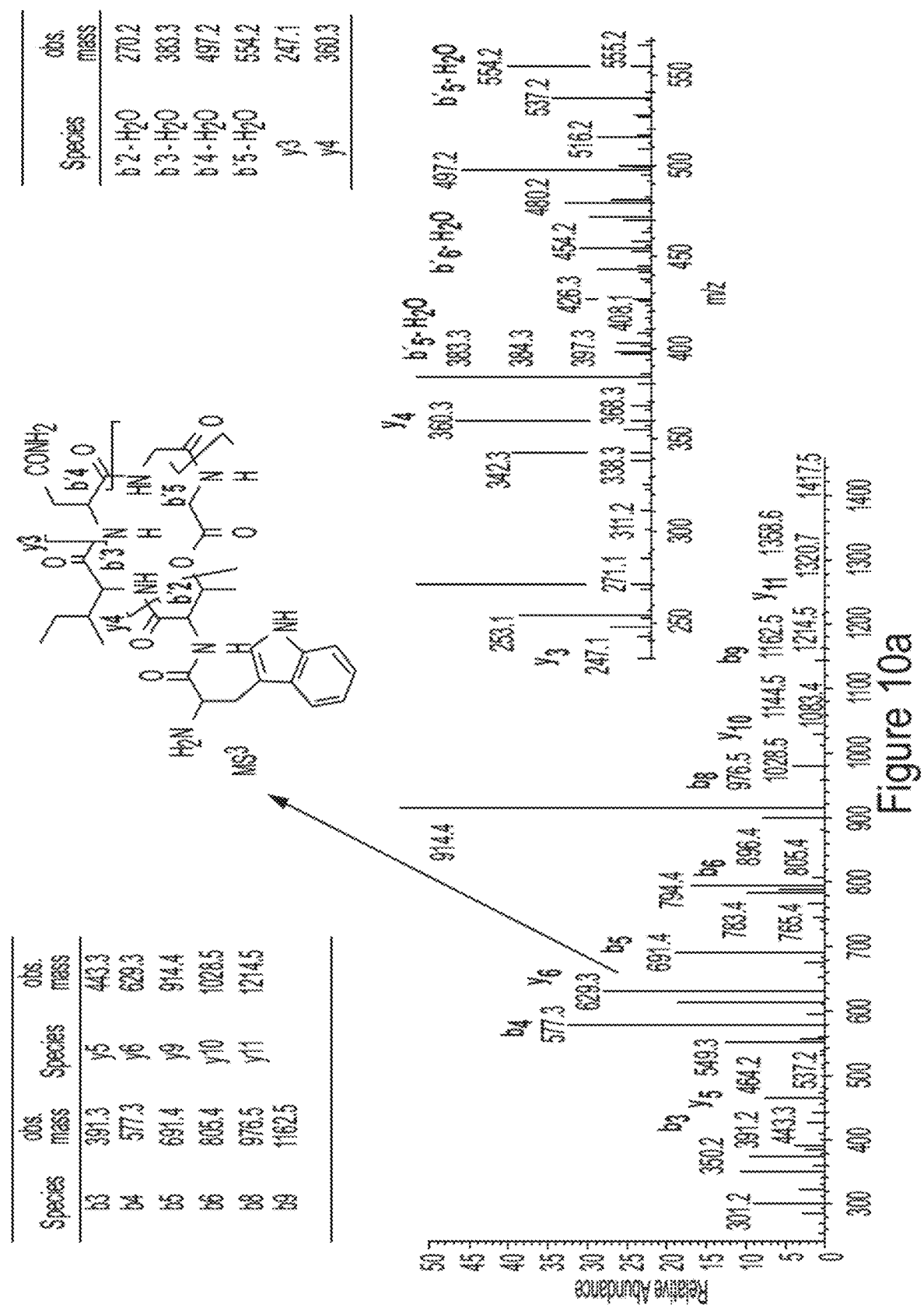
Figures 10B, 10C:
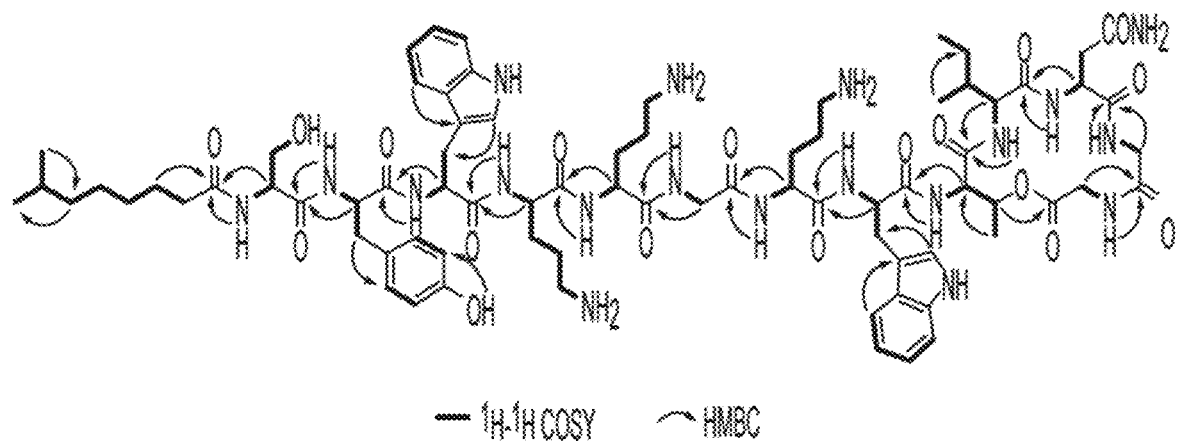

FIGS. 10a-10c show MS, NMR, and Marfey-type analyses of laterocidine (2). FIG. 10a $MS_n$ analysis of laterocidine. FIG. 10b The key $^1H$-$^1H$-COSY and $^1H$-$^{13}C$-HMBC correlation of compounds 2. FIG. 10c Marfey-type analysis of brevicidine (Retention times (in min) of 2 constituent amino acids derivatized with D/L-FDLA). The $^1H$, $^1H$-$^1H$-COSY, $^1H$-$^{13}C$-HSQC, and $^1H$-$^{13}C$-HMBC NMR data of 2 were recorded on a Bruker AV500 spectrometer (500 MHz) using DMSO-$d_6$ (1H-NMR: DMSO-$d_6$: δ=2.50 ppm; $^{13}C$-NMR: DMSO-$d_6$: δ=39.8 ppm). Compound 2 was obtained as a white amorphous solid. Based on HRESIMS data (m/z: 802.9345 [M+2H]$^{2+}$, calc 802.9329), its molecular formula was established as $C_{78}H_{113}N_{19}O_{18}$. The characteristic signals of the amide NH and α-amino proton in the $^1H$ NMR spectrum and carbonyl groups in the $^{13}C$ NMR spectrum (FIG. 21) indicated the peptidic nature of the compound. The gross structure of laterocidine was further established by analyses of the $^1H$, $^{13}C$, $^1H$-$^1H$ COSY, HMQC, and HMBC NMR spectral data (FIGS. 10b and 21), revealing the presence in its structure of Orn (3), Trp (2), Gly (3), Ile (1), Ser (1), Thr (1), Asn(1), Tyr (1) and a lipidic residue that was identified as 7-methyloctanoic acid. The gross structure established by NMR analysis was also corroborated by MS/MS analysis (FIG. 10a).

Amino acid configurations of 2 were determined through Marfey's analysis of compound 2 and its hydrolytic products 7, 8 and 10 as described above. On the basis of the combination of the data generated by advanced Marfey's analysis and biosynthetic pathway analysis (FIGS. 13a-13b), a lipodepsipeptide 7-Methyl-Octanoyl-D-Ser-D-Tyr-D-Trp-D-Orn-Orn-Gly-D-Orn-Trp-Thr-Ile-Asn-Gly-Gly (cyclized via lactone formation between Thr and the C-terminus) was established for the natural product laterocidine.

Figures 11A, 11B:
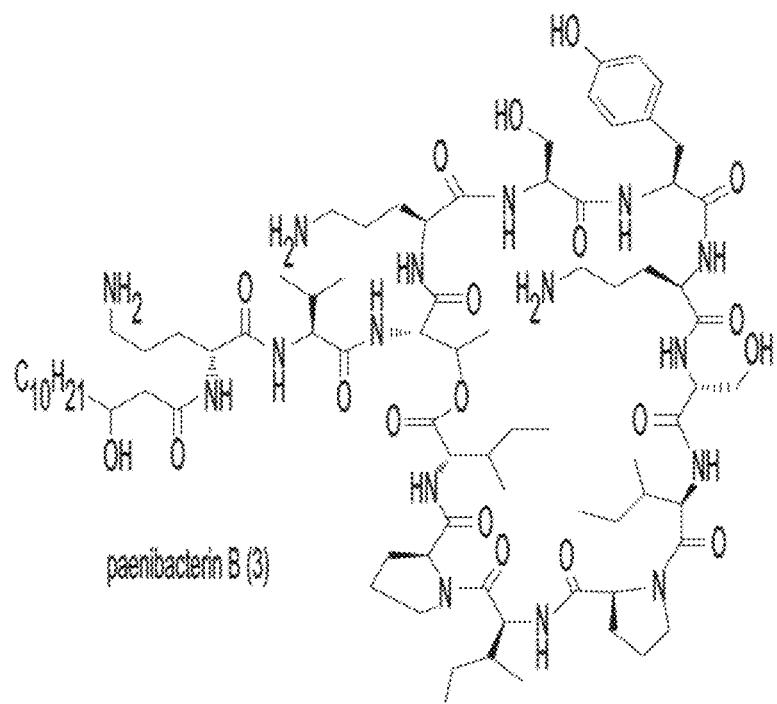
Figure 11C:
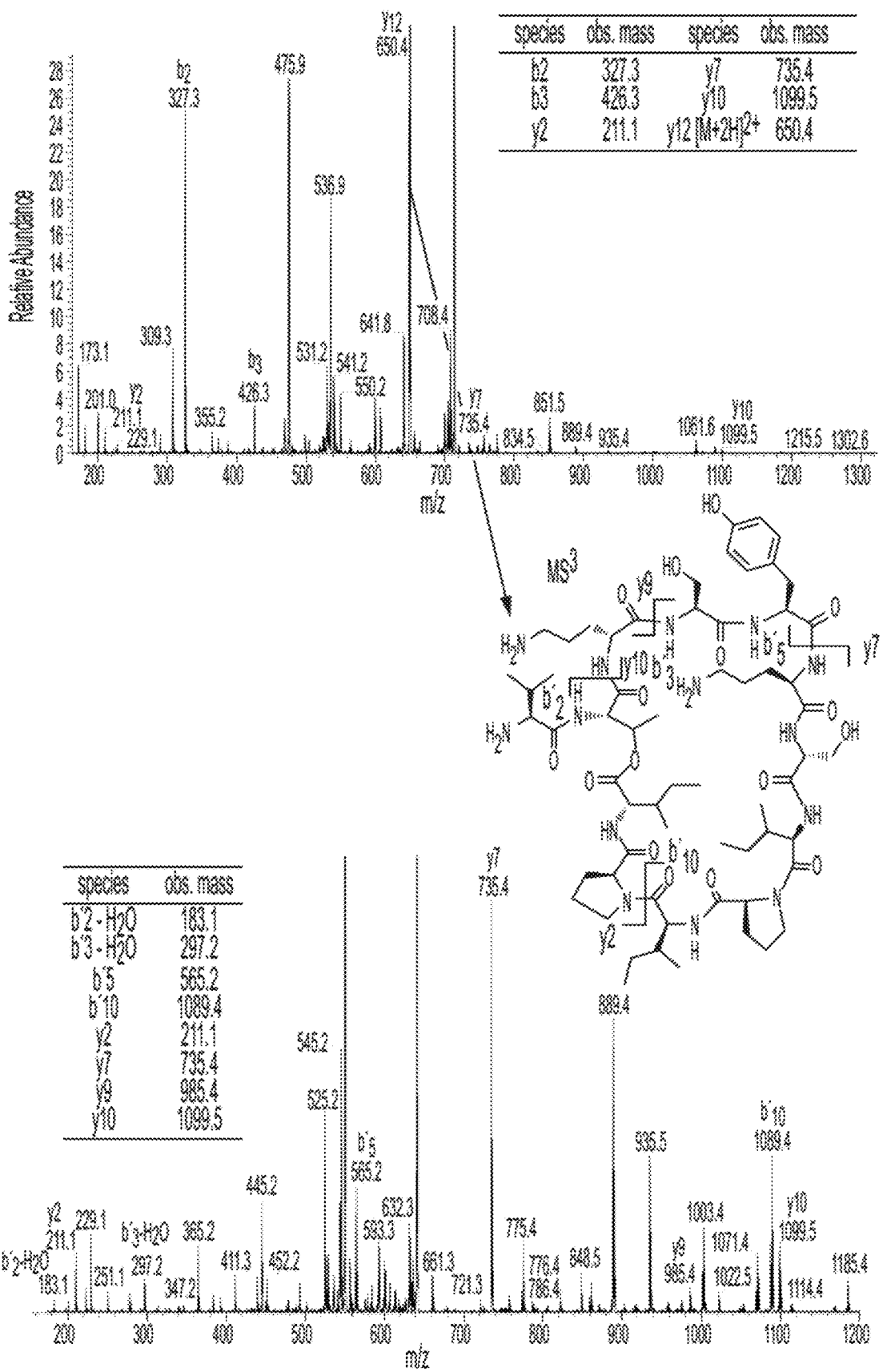

FIGS. 11a-11c show MS analyses of Paenibacterin B (3). FIG. 11a Comparison of BGCs of paenibacterin B (paeA-G, from NZ_AMBZ01000008, 57,959-110,917 nt)) and paenibacterin A (pbtA-C). FIG. 11b Structure of paenibacterin B, identified by MS/MS analysis. FIG. 11c $MS_n$ analysis of paenibacterin.

FIGS. 12a-12b show the predicted biosynthetic pathway of brevicidine (Domain abbreviation, C, condensation; A, adenylation; T, thiolation (carrier); E, epimerization; and TE, thioesterase; gene cluster location: KB894285, 144,281-196,331 nt) Biosynthesis of brevicidine starts with the typical starting module for NRPs with a condensation starter domain that acylates the N-terminal with a fatty acid. In accordance with the co-linearity rule, 12 amino acids are introduced into the linear peptide, and the ring closure between the last $Ser_{12}$ and $Thr_9$ is catalyzed by the thioesterase domain during product offloading, resulting in brevicidine.

Figure 13A:
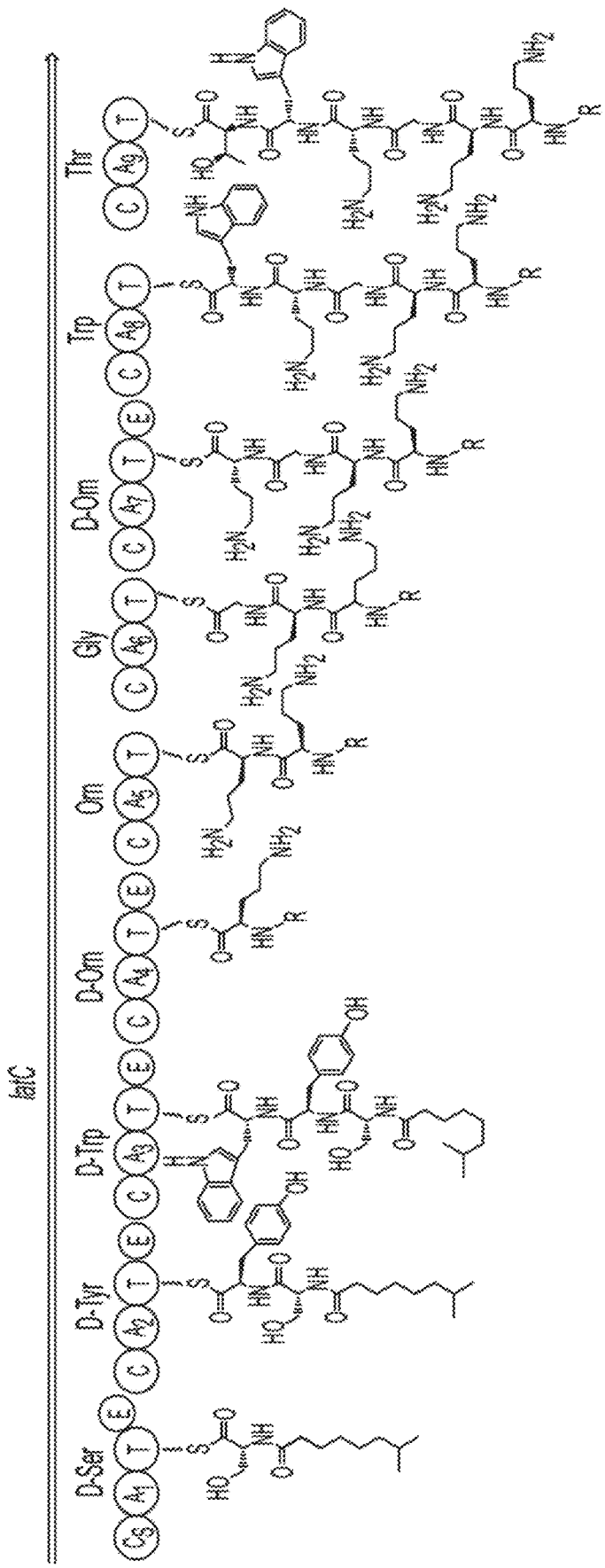
Figure 13B:
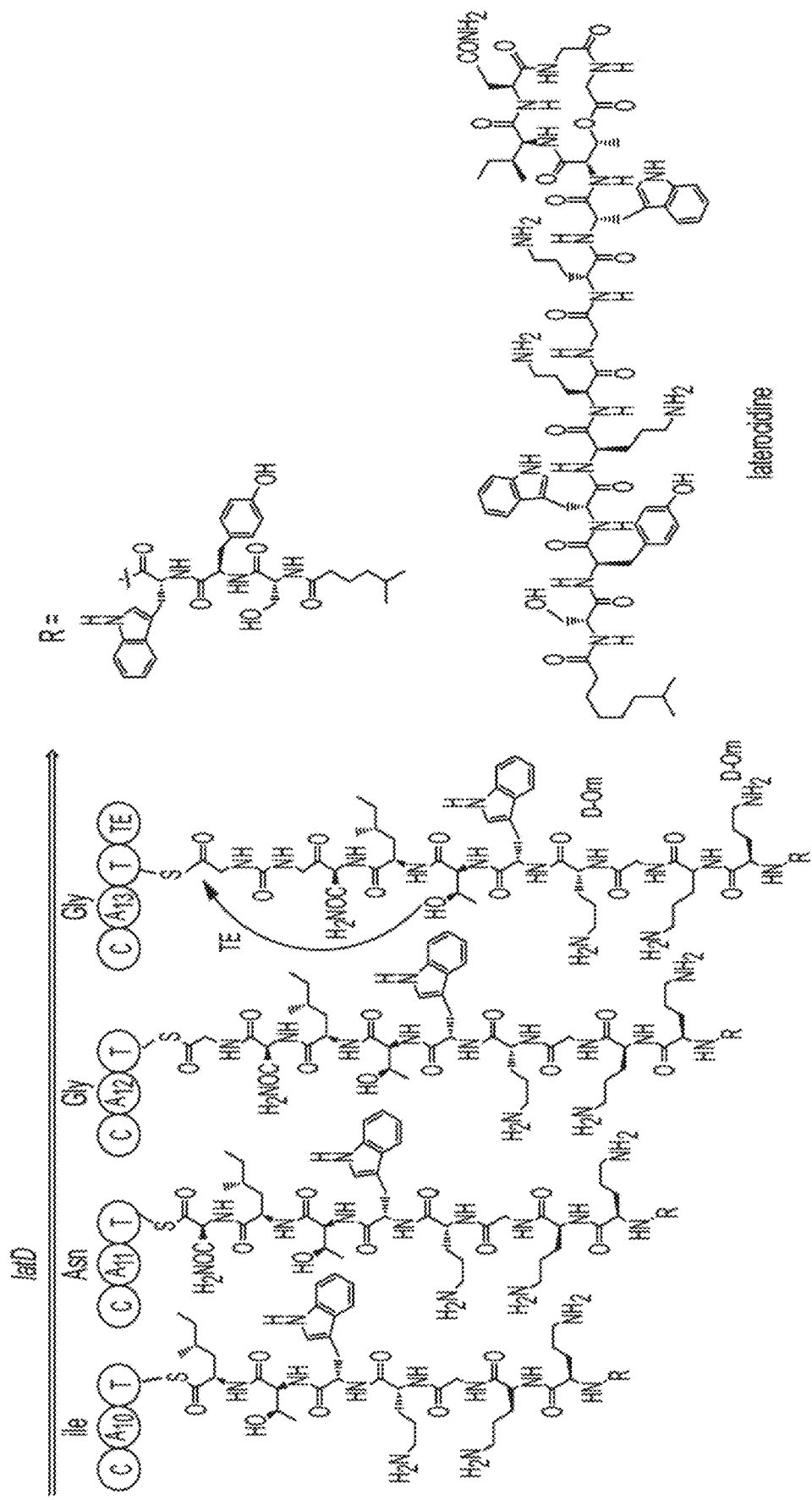

FIGS. 13a-13b show the predicted biosynthetic pathway of laterocidine (Domain abbreviation, C, condensation; A, adenylation; T, thiolation (carrier); E, epimerization; and TE, thioesterase; gene cluster location: NZ_CP007806.1, 2,835,471-2,890,522) Biosynthesis of laterocidine starts with the typical starting module for NRPs with a condensation starter domain that acylates the N-terminal with a fatty acid. In accordance with the co-linearity rule, 13 amino acids are introduced into the linear peptide, and the ring closure between the last $Gly_{13}$ and $Thr_9$ is catalyzed by the thioesterase domain during product offloading, resulting in laterocidine.

Figure 14:
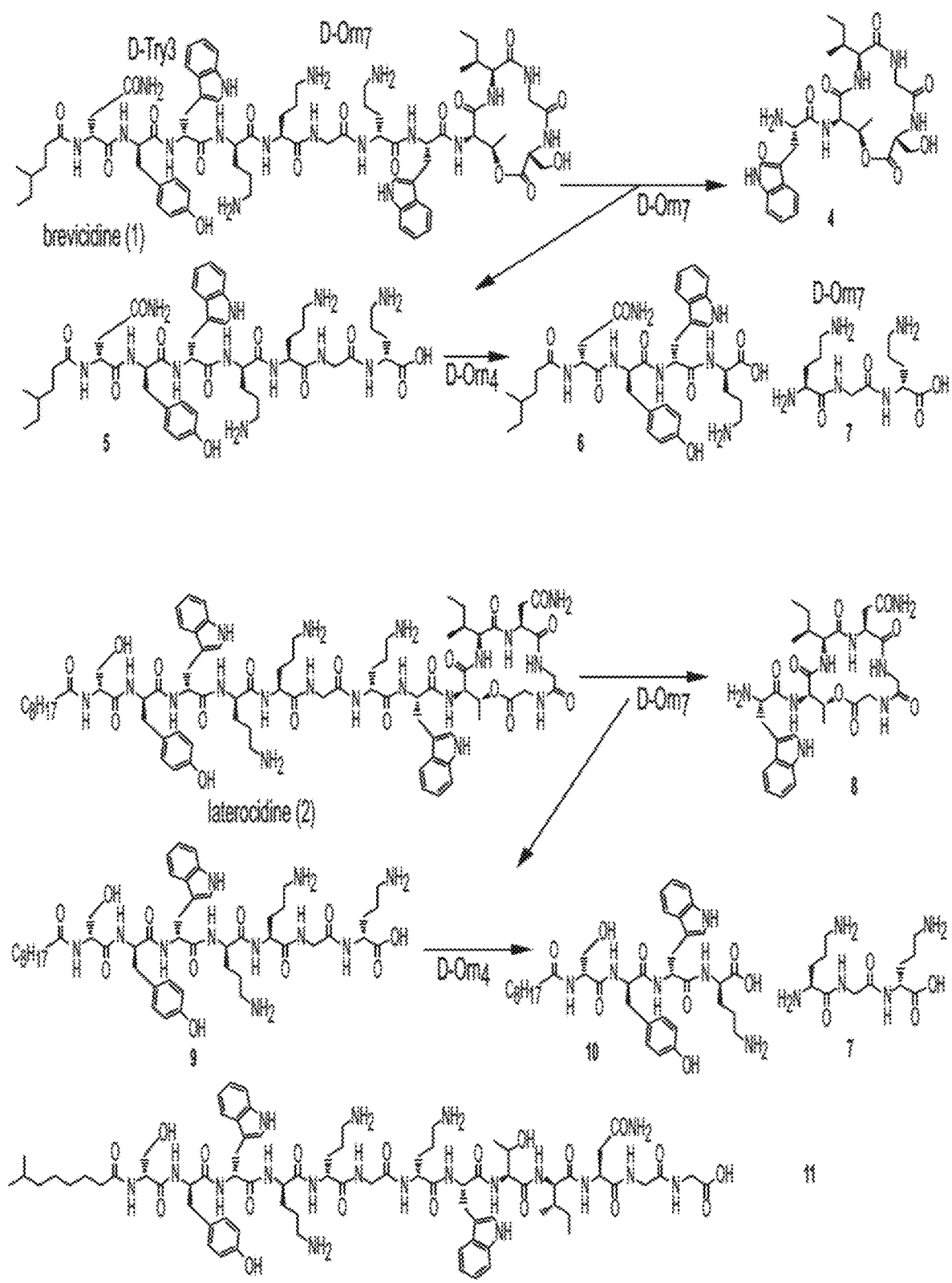

FIG. 14 shows chemical structures of CNRP derivatives.

Figures 15A, 15B:
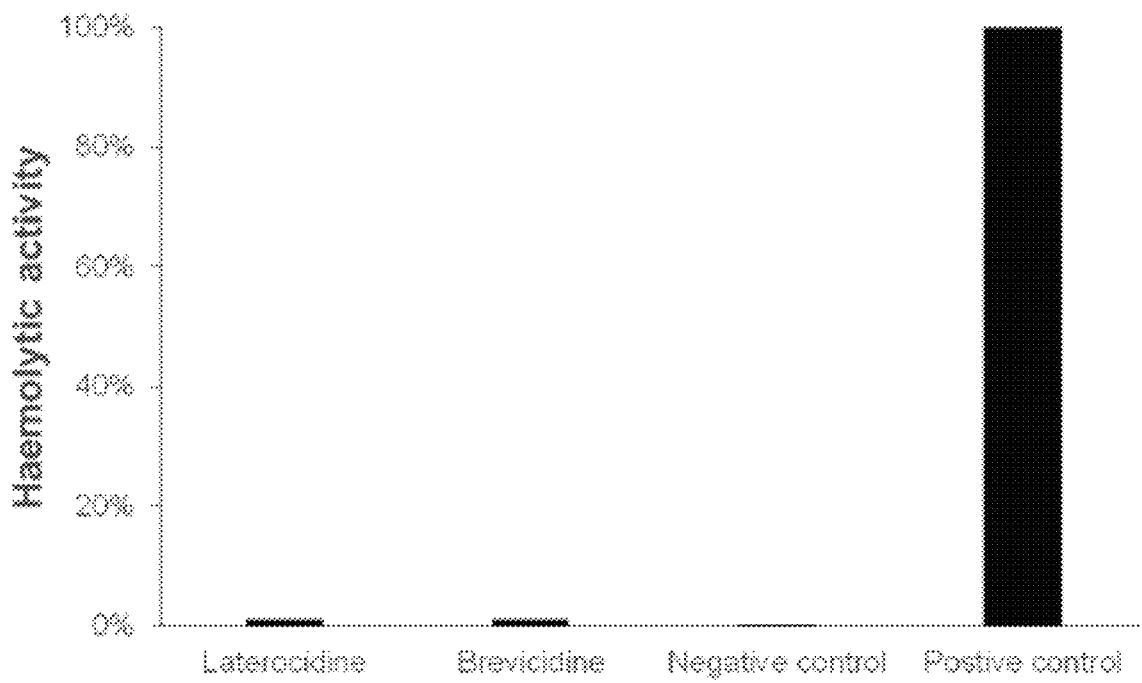

FIGS. 15a-15b show brevicidine and laterocidine activity against eukaryotic cells. FIG. 15a Rabbit erythrocytes were incubated with brevicidine or laterocidine at concentrations up to 128 μg mL$^{-1}$. Their lysis was monitored by the release of hemoglobin. Cells without a tested compound were used as negative control. Incubation of cells in 10% Triton X-100 was used as positive control for complete lysis. The data are representative of two independent experiments. FIG. 15b Cytotoxicity of brevicidine and laterocidine. The data are representative of three independent experiments.

Figure 16:
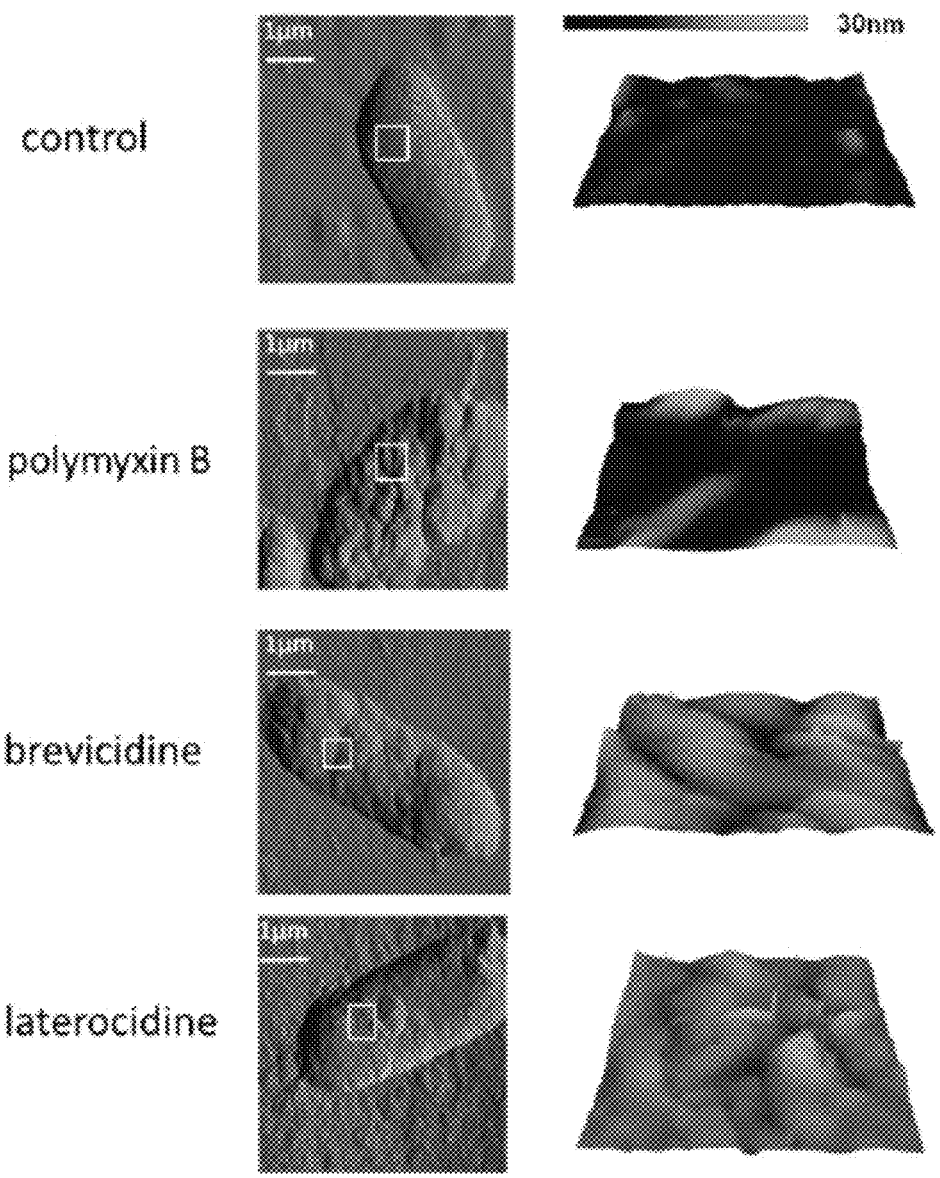

FIG. 16 show atomic force microscopy of brevicidine/laterocidine-treated *E. coli* ATCC 25922 revealed a dramatic effect on the outer membrane structure. The data are representative of three independent experiments.

Figure 17:
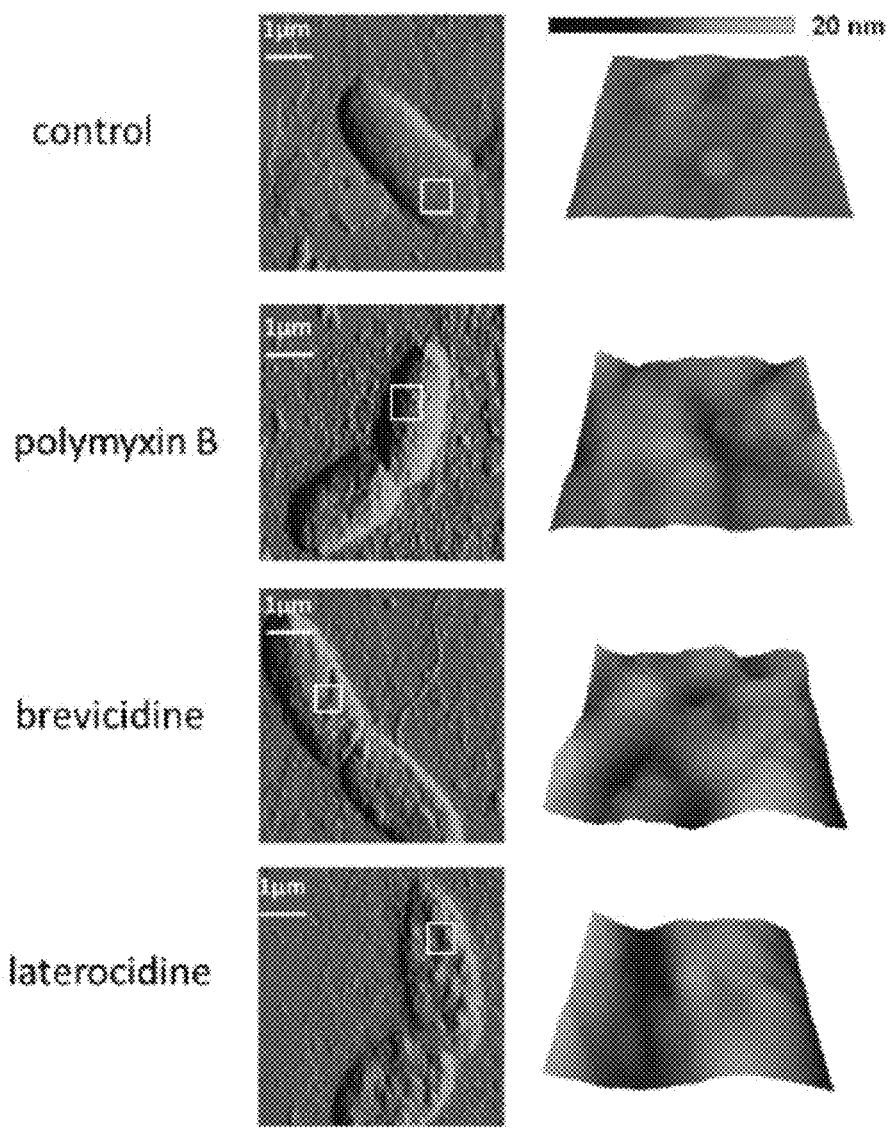

FIG. 17 show atomic force microscopy of brevicidine/laterocidine-treated *P. aeruginosa* PAO1 revealed a dramatic effect on the outer membrane structure. The data are representative of three independent experiments.

Figure 18A:
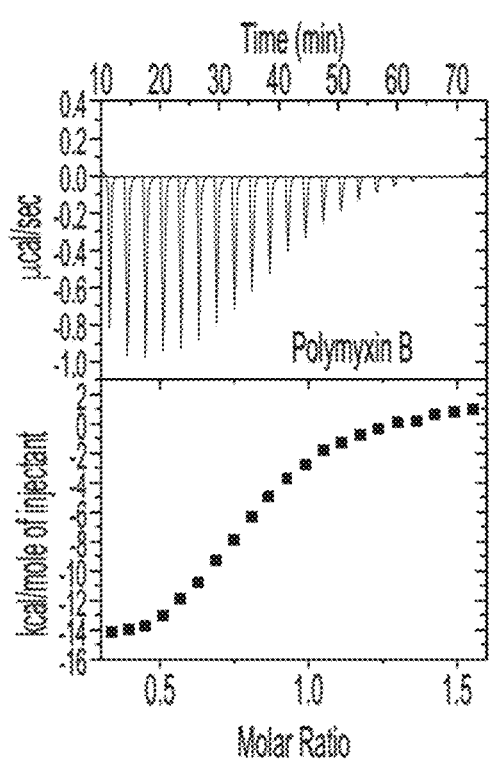
Figure 18B:
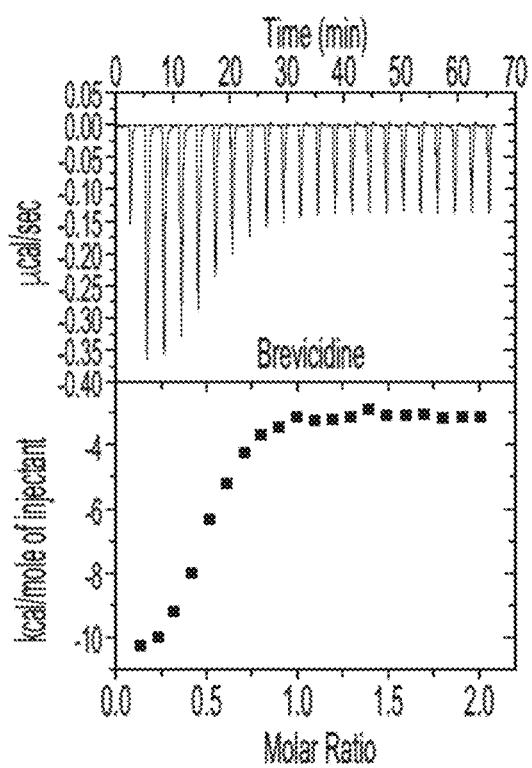

FIGS. 18a-18b show binding of brevicidine and polymyxin B to LPS from *E. coli* revealed by isothermal titration calorimetry (ITC). FIG. 18a Polymyxin B+LPS. FIG. 18b Brevicidine+LPS. All results show strong binding to LPS.

Figure 19:
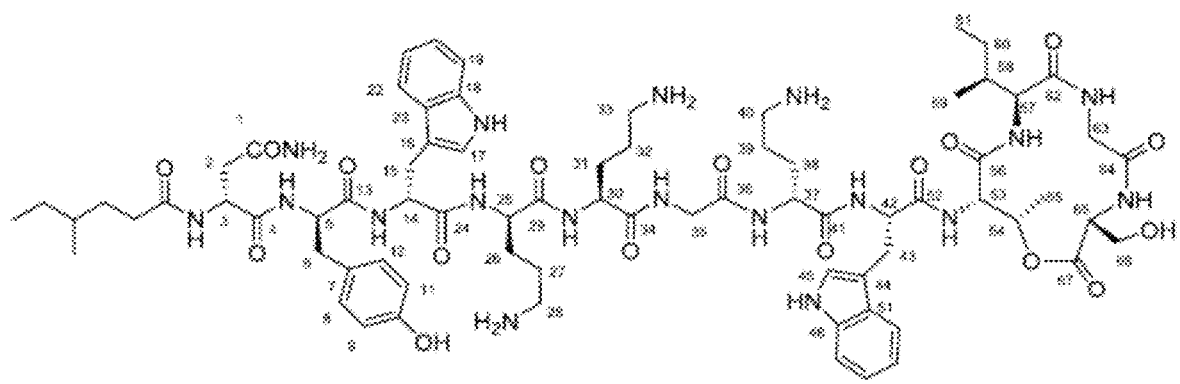

FIG. 19 shows the structure of brevicidine (1) with NMR assignments.

Figure 20A:
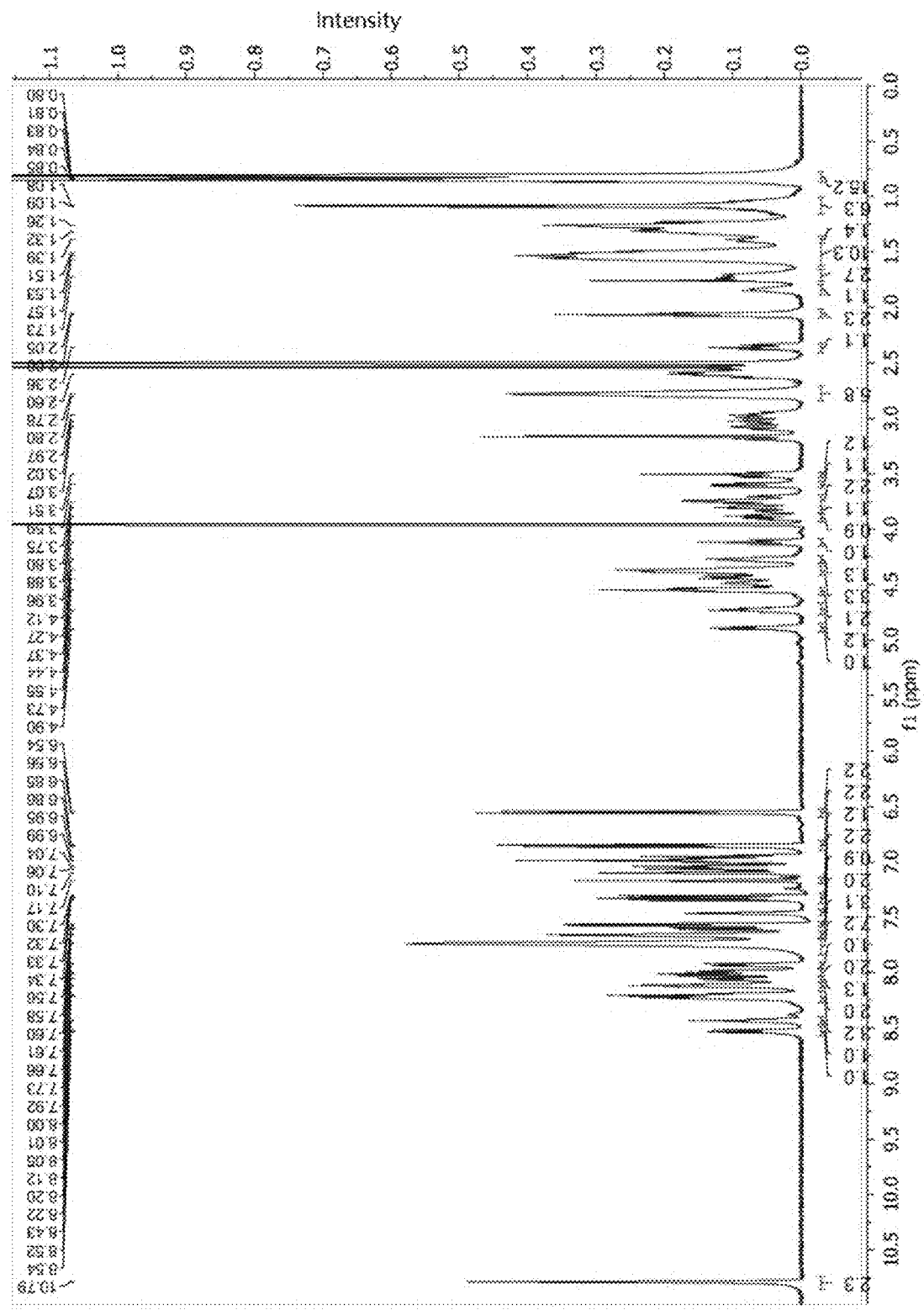
Figure 20B:
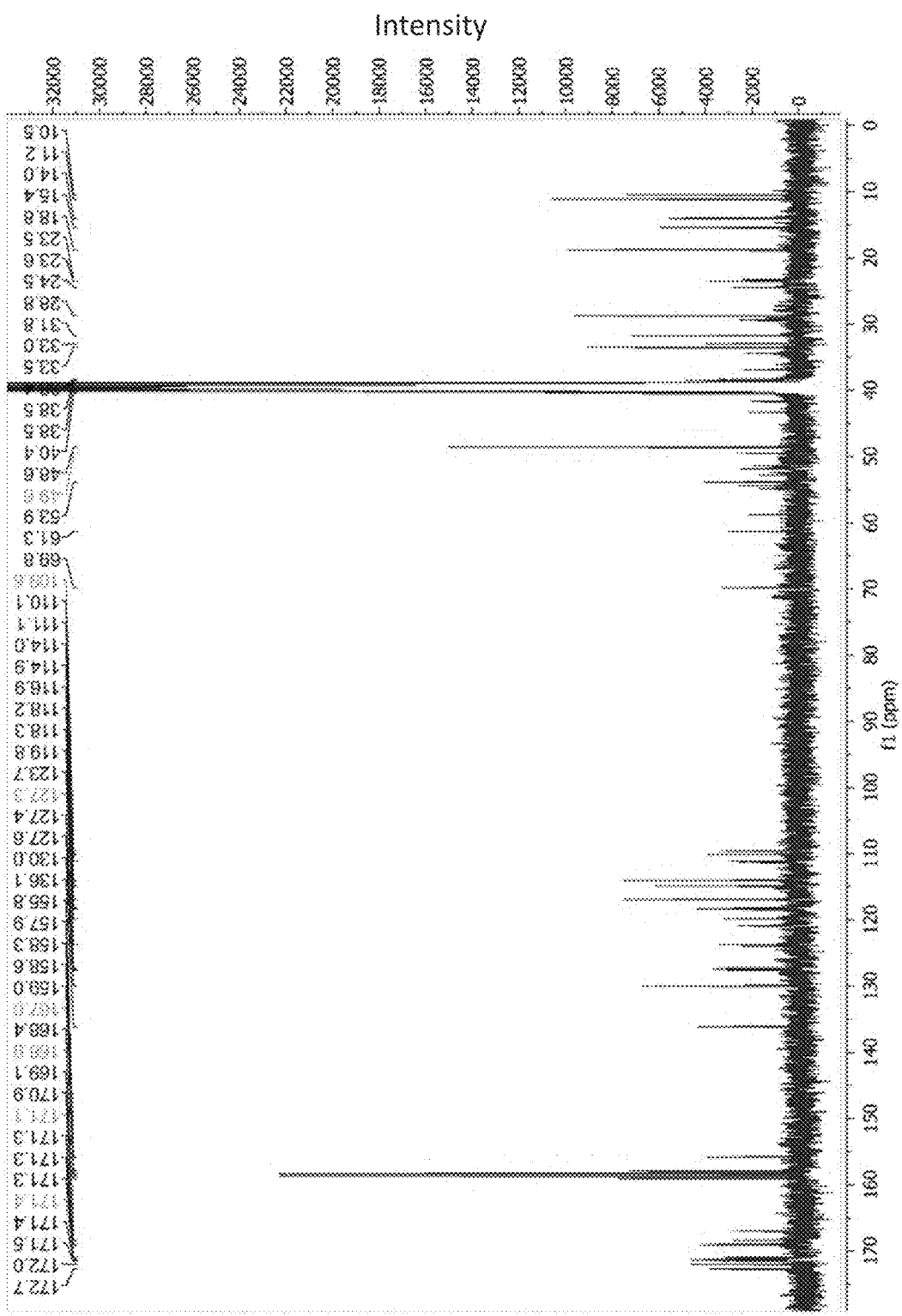
Figure 20C:
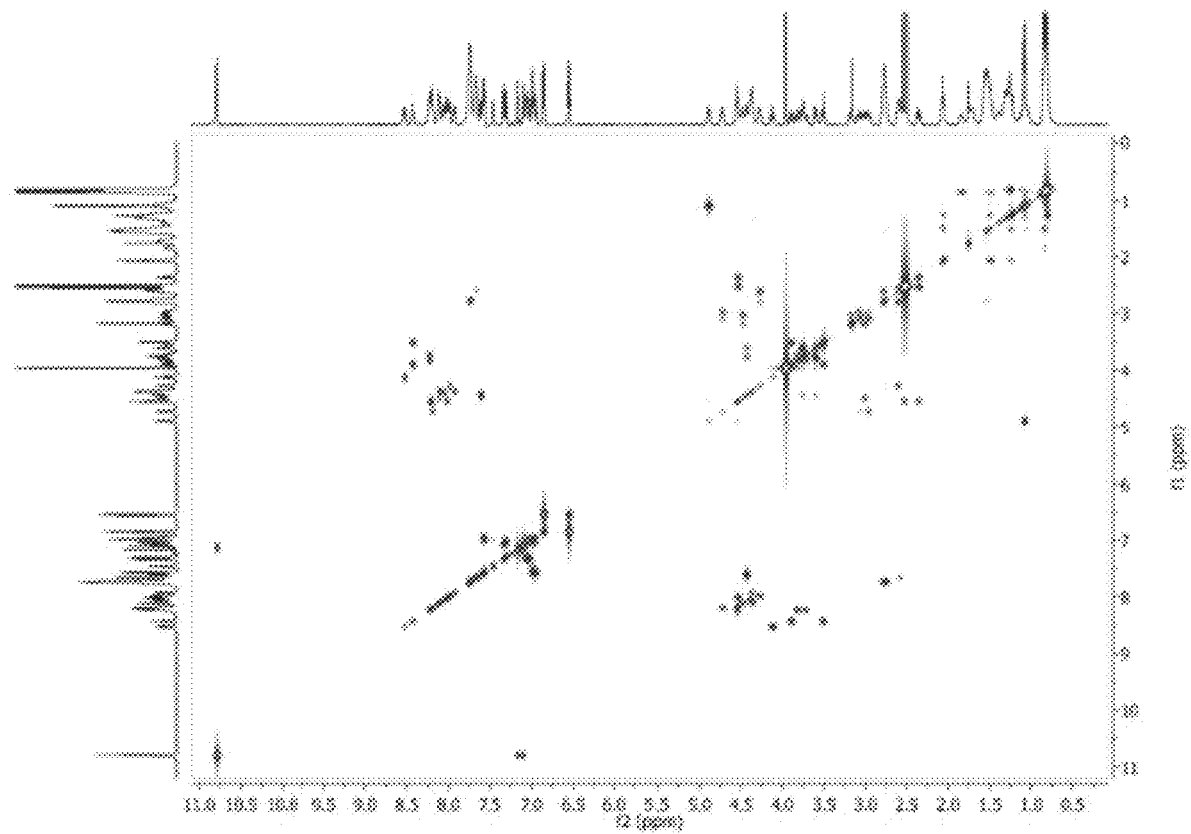
Figure 20D:
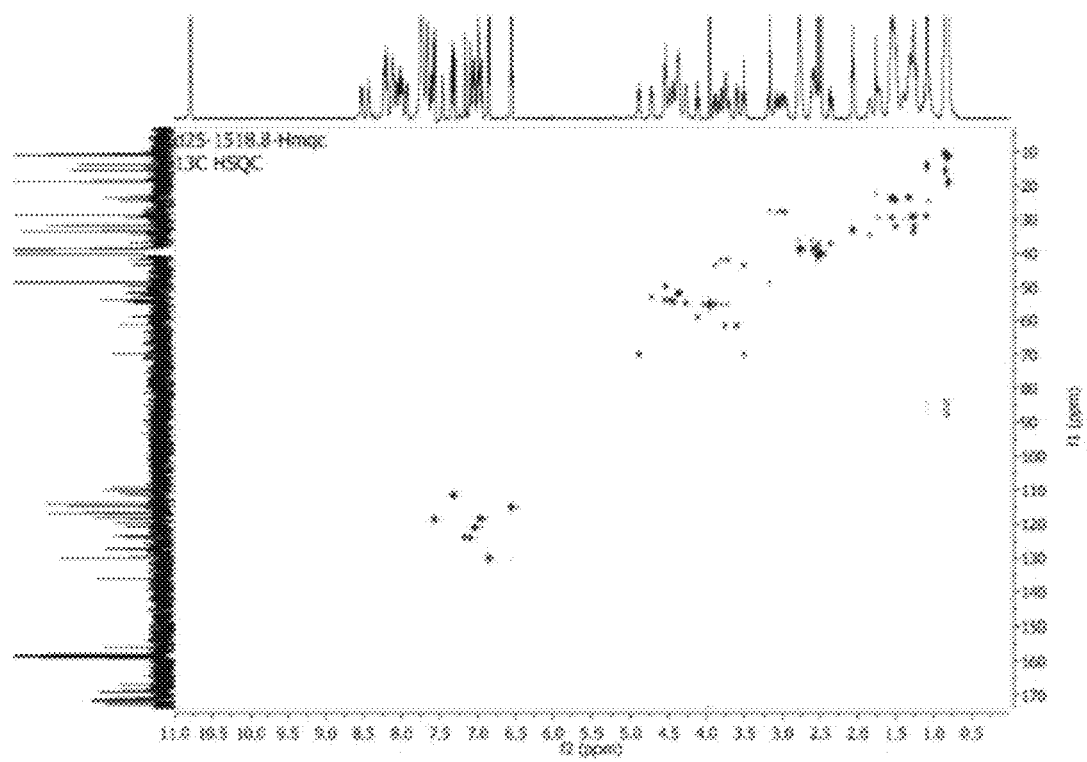
Figure 20E:
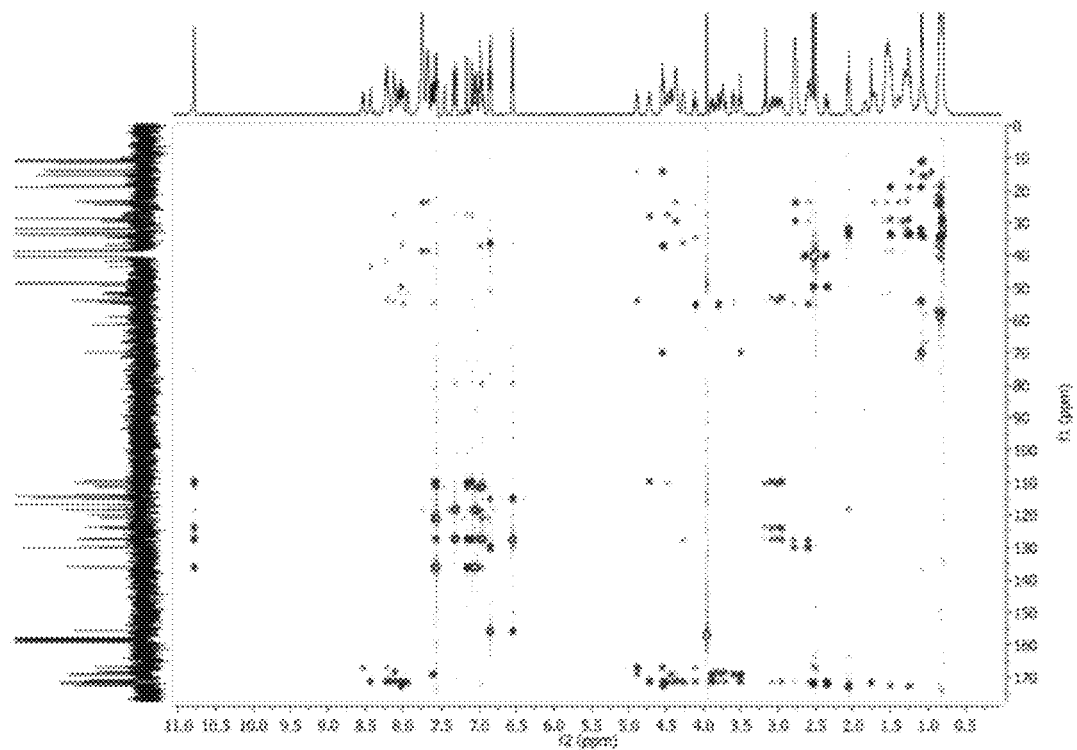
Figure 20F:
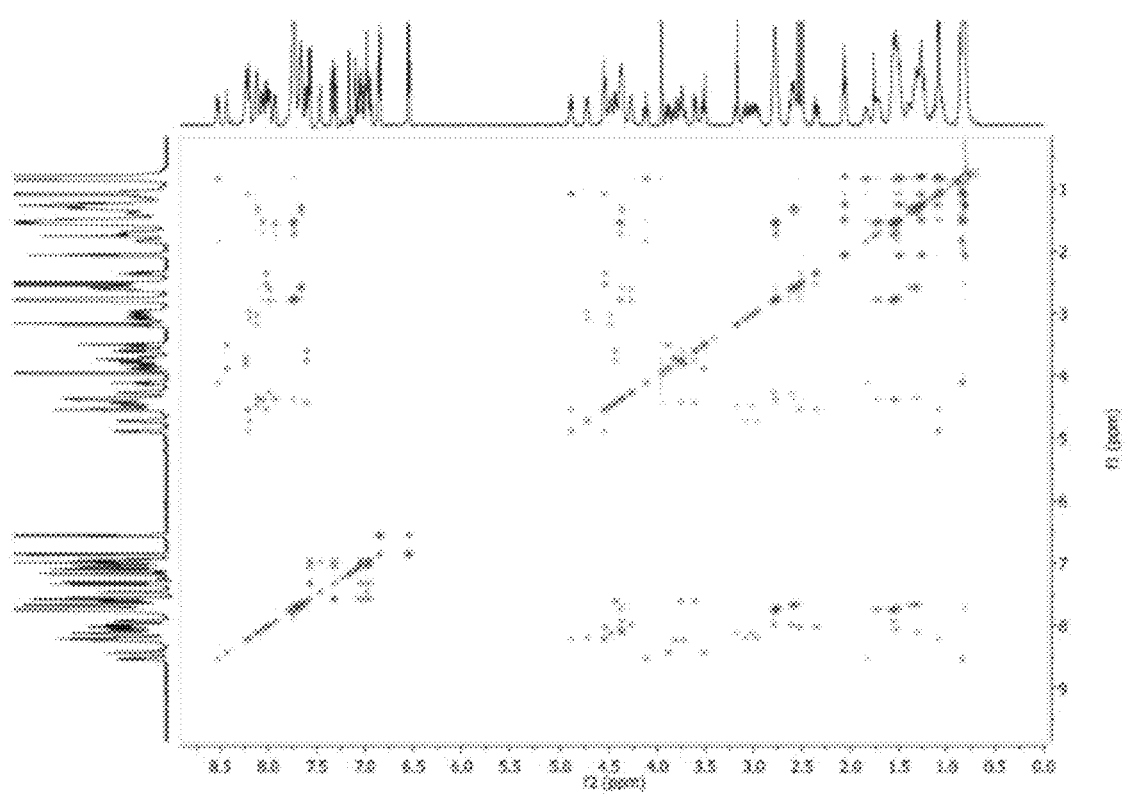

FIGS. 20a-20f show: FIG. 20a $^1$HNMR of brevicidine (1) (DMSO-d$_6$, 500 MHz); FIG. 20b $^{13}$C-NMR of brevicidine (1) (DMSO-d$_6$, 100 MHz); FIG. 20c $^1$H-$^1$H COSY of brevicidine (1) (DMSO-d$_6$, 500 MHz); FIG. 20d $^1$H-$^{13}$C HSQC of brevicidine (1) (DMSO-d$_6$, 500 MHz); FIG. 20e $^1$H-$^{13}$C HMBC of brevicidine (1) (DMSO-d$_6$, 500 MHz); and FIG. 20f $^1$H-$^1$H TOCSY of brevicidine (1) (DMSO-d$_6$, 500 MHz).

Figure 21:
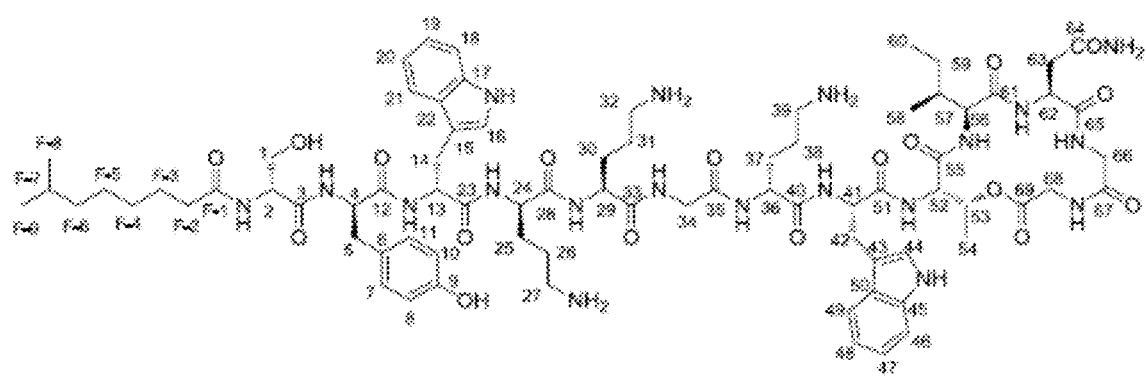

FIG. 21 shows the structure of laterocidine (2) with the NMR assignments.

Figure 22A:
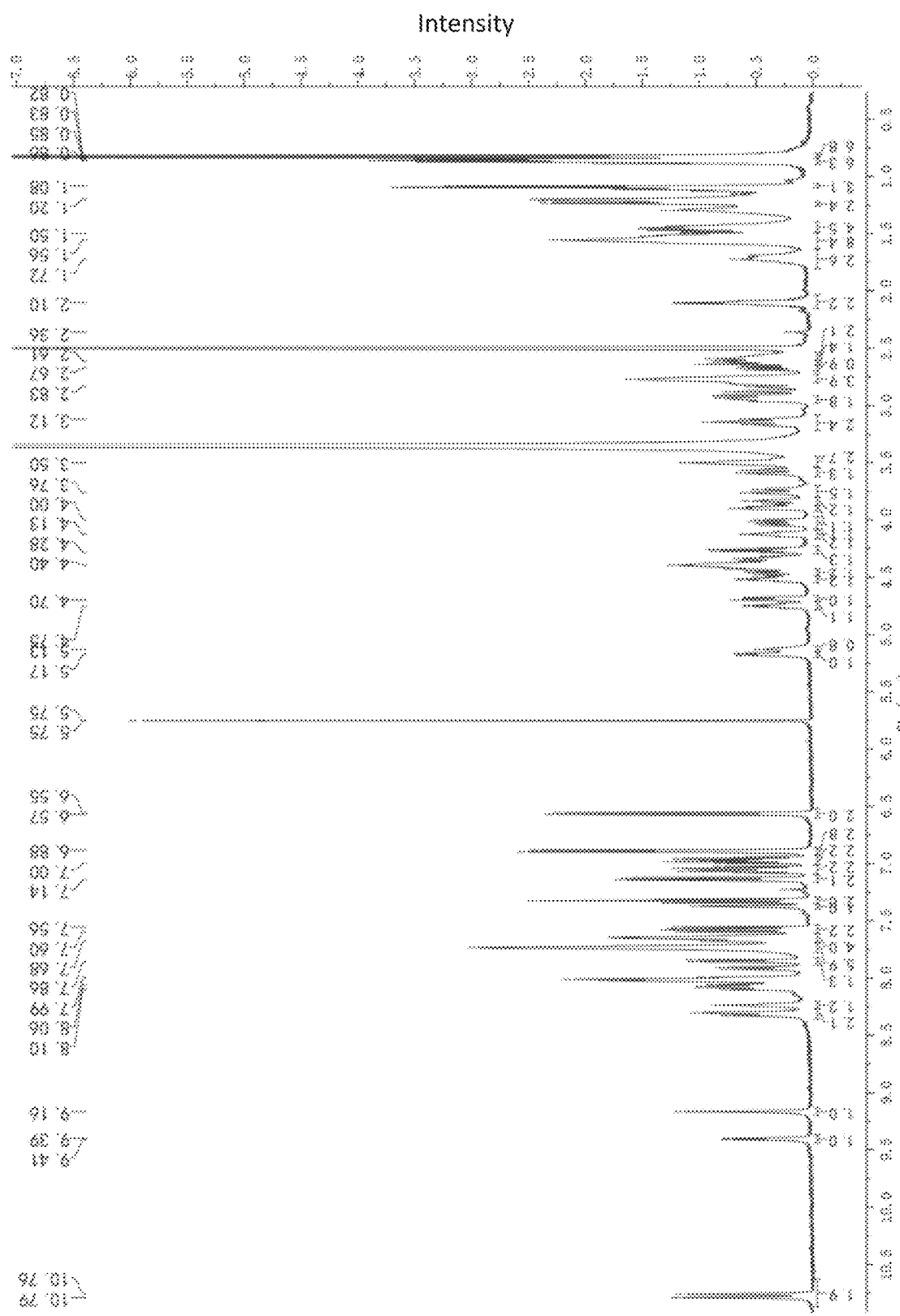
Figure 22B:
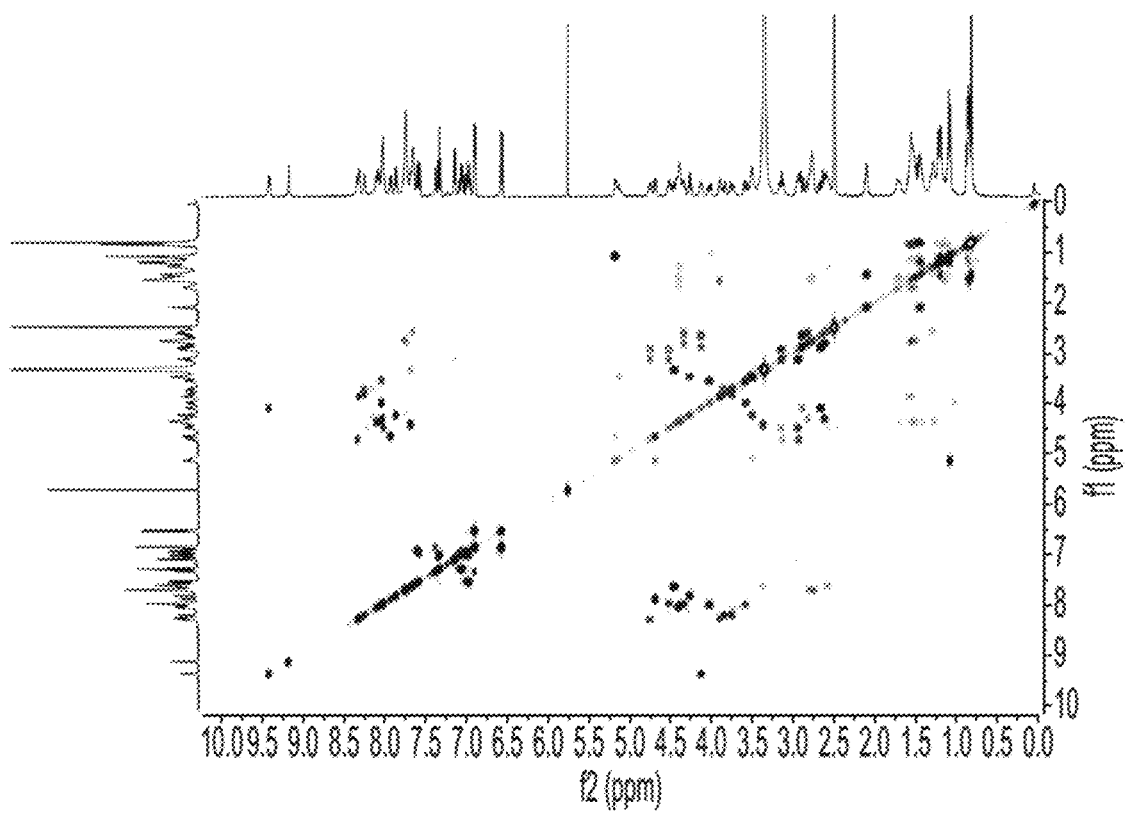
Figure 22C:
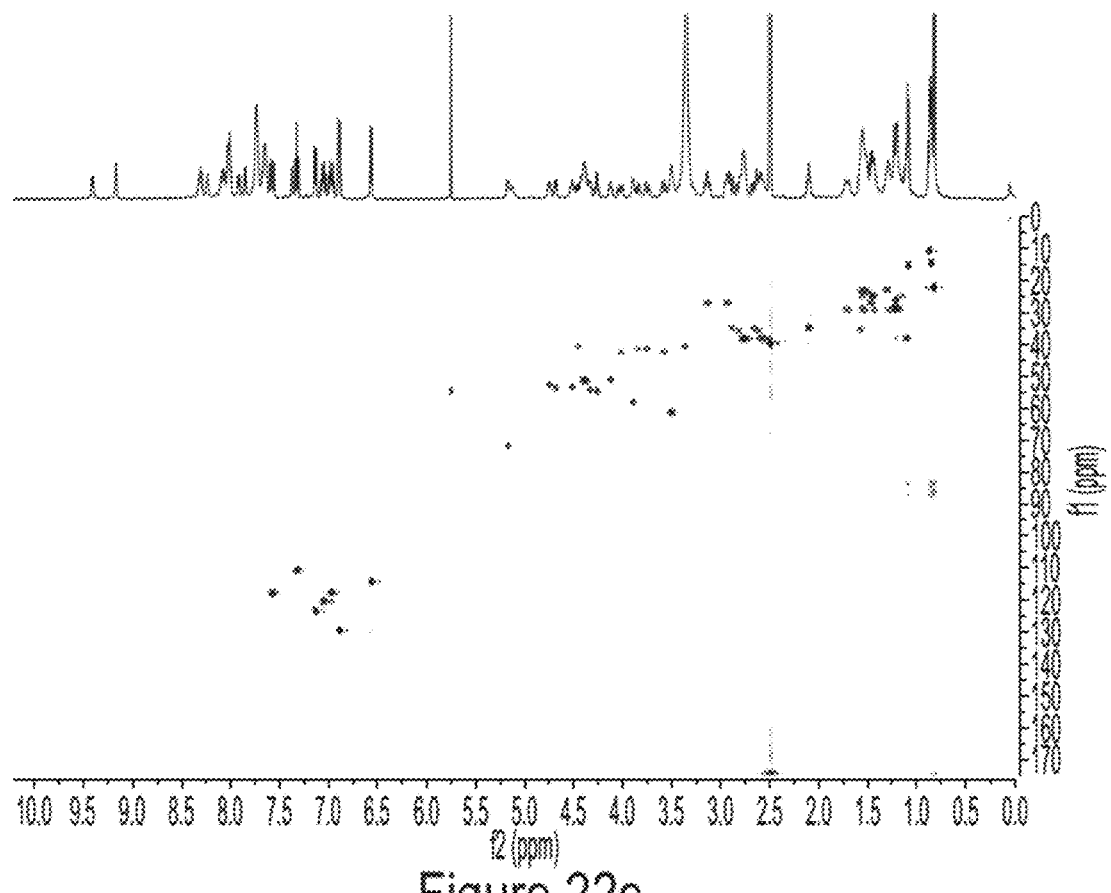
Figure 22D:
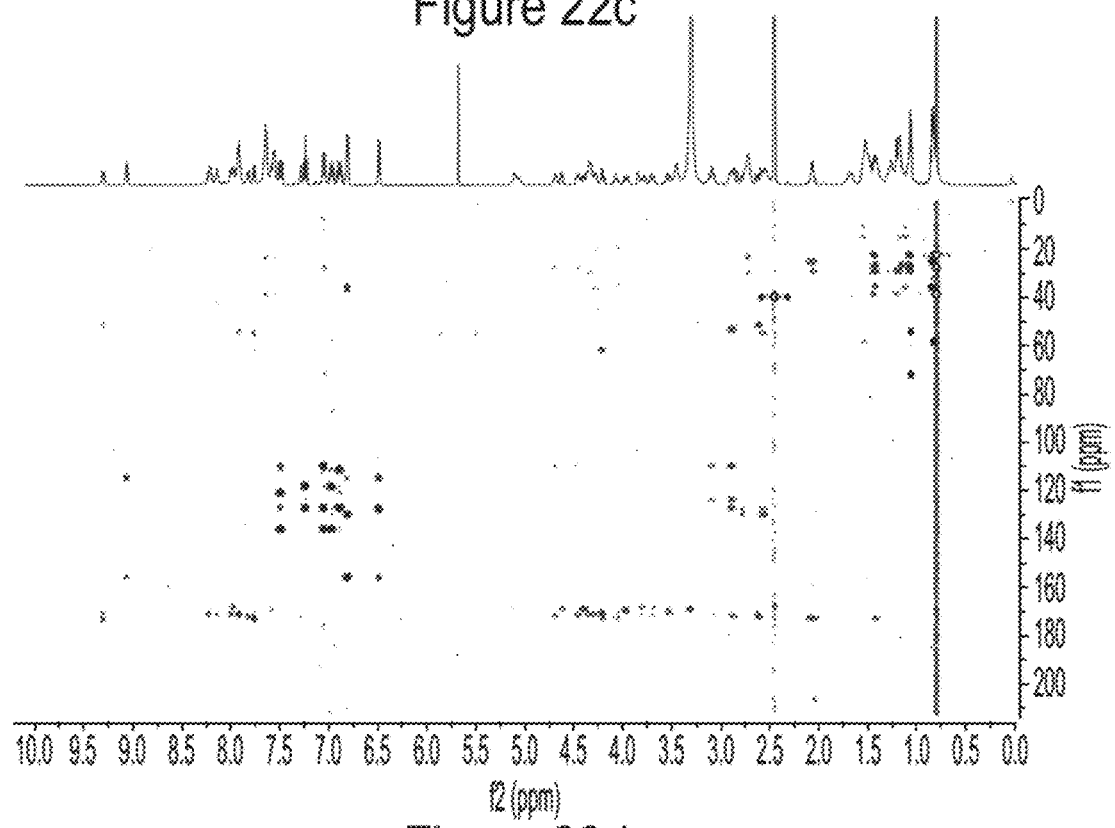
Figure 22E:
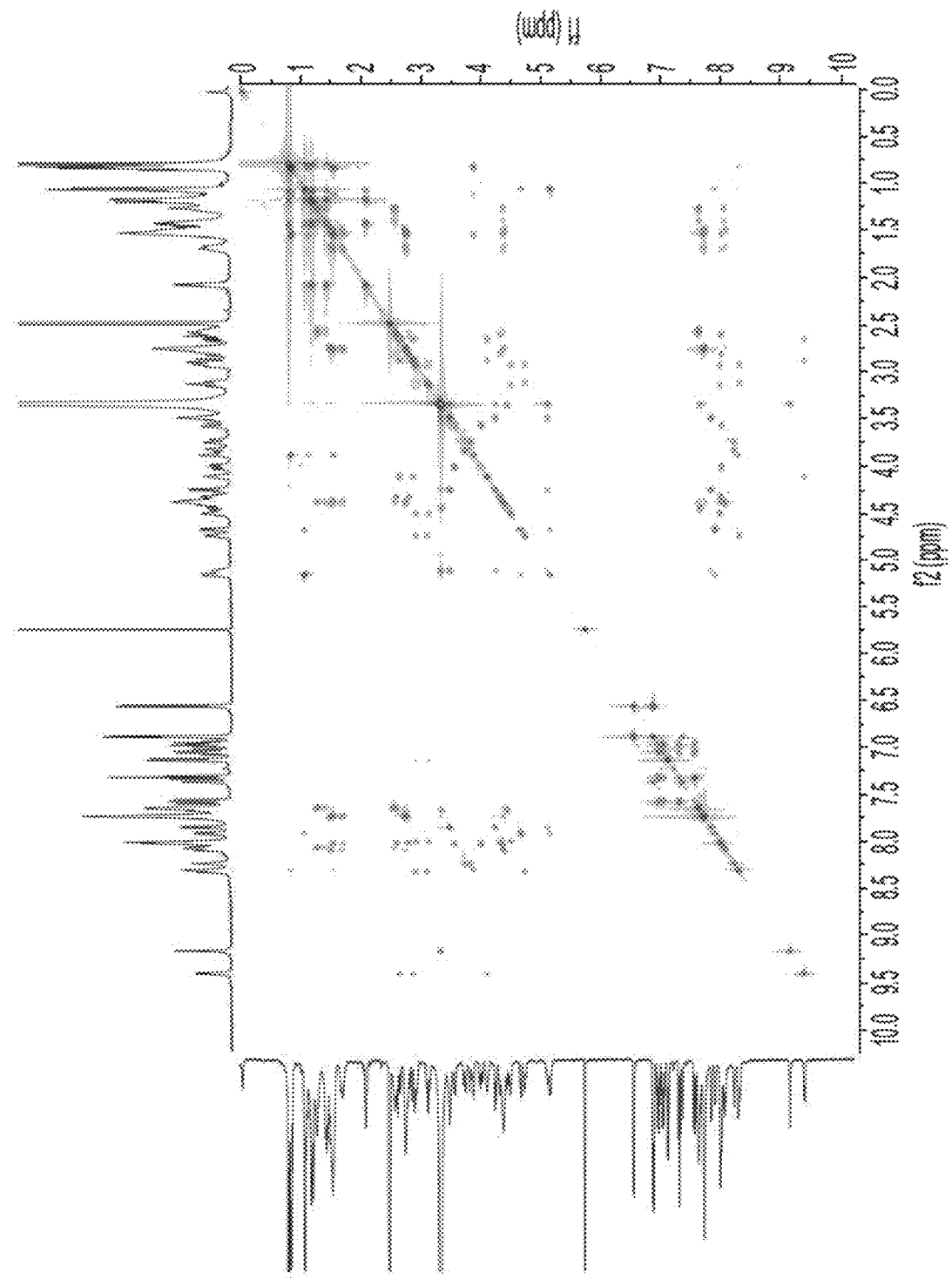

FIGS. 22a-22e show: FIG. 22a $^1$HNMR of laterocidine (2) (DMSO-d$_6$, 500 MHz); FIG. 22b $^1$H-$^1$H COSY of laterocidine (2) (DMSO-d$_6$, 500 MHz); FIG. 22c $^1$H-$^{13}$C HSQC of laterocidine (2) (DMSO-d$_6$, 500 MHz); FIG. 22d $^1$H-$^{13}$C HMBC of laterocidine (2) (DMSO-d$_6$, 500 MHz); FIG. 22e $^1$H-$^1$H TOCSY of laterocidine (2) (DMSO-d$_6$, 500 MHz).

Figure 23:
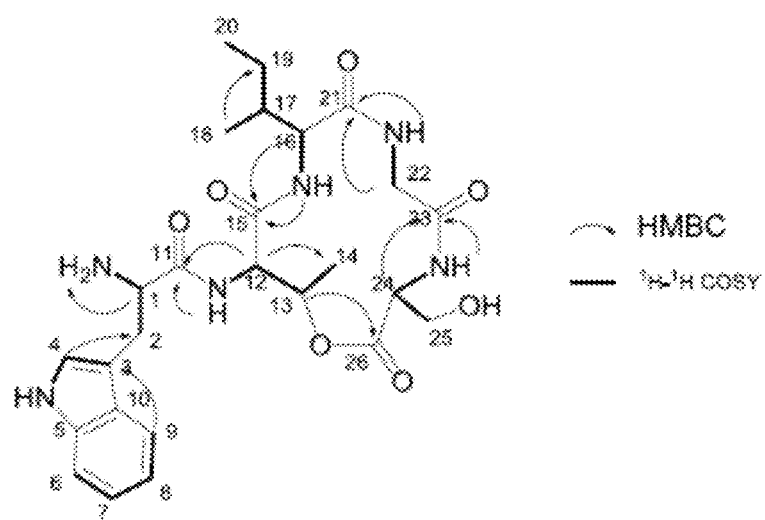

FIG. 23 shows Key $^1$H-$^1$H COSY and HMBC correlation of 4.

Figure 24A:
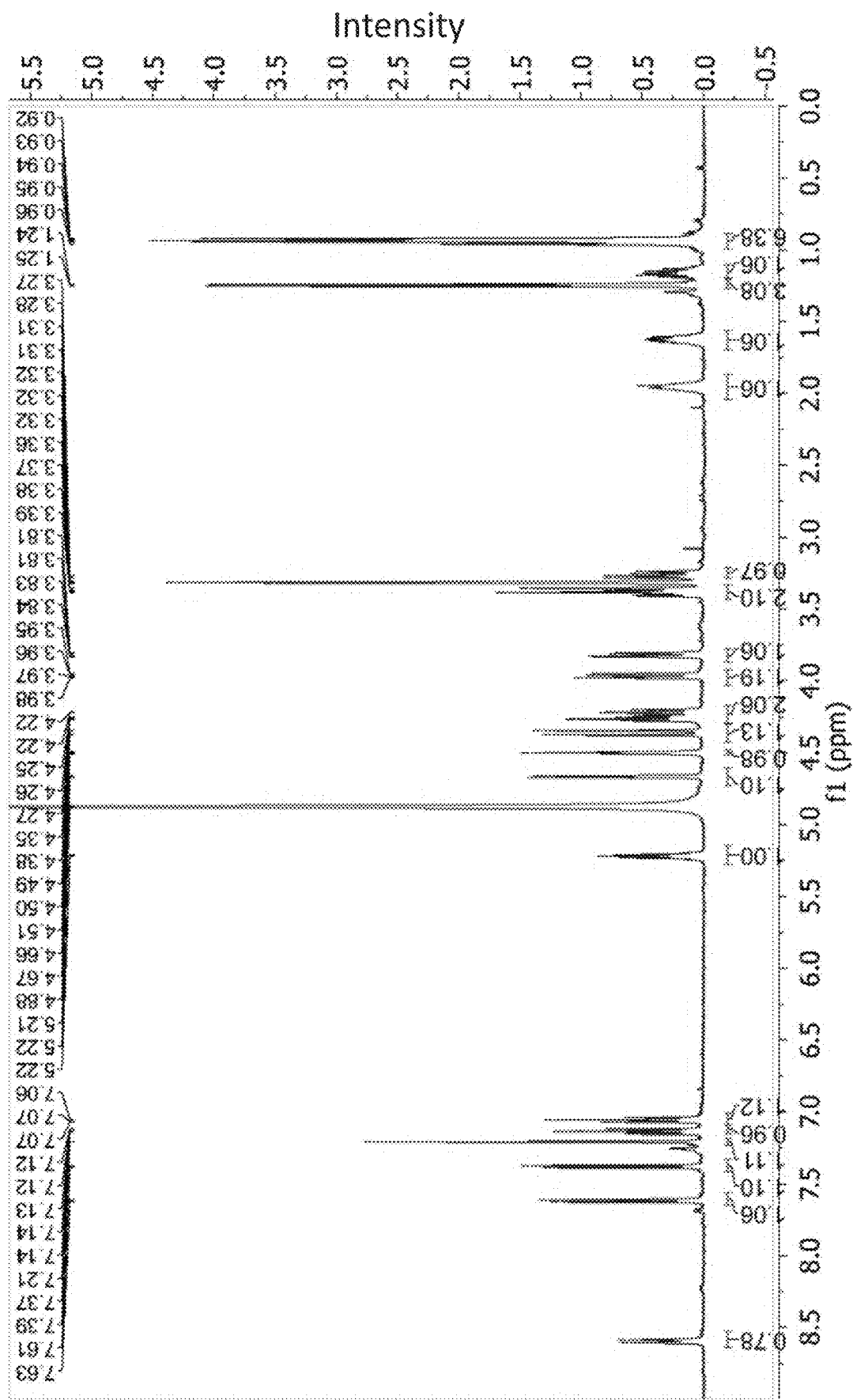
Figure 24B:
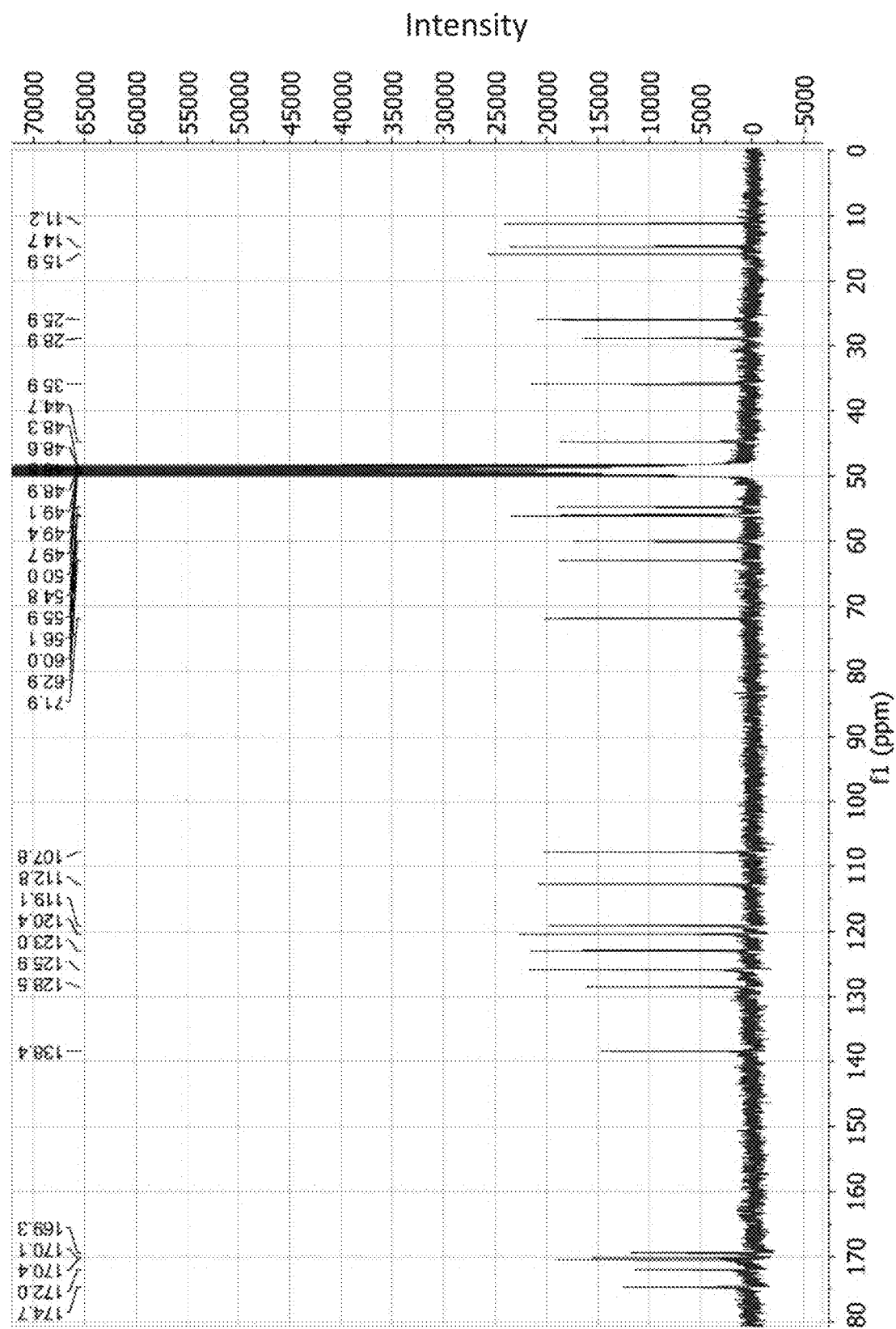
Figure 24C:
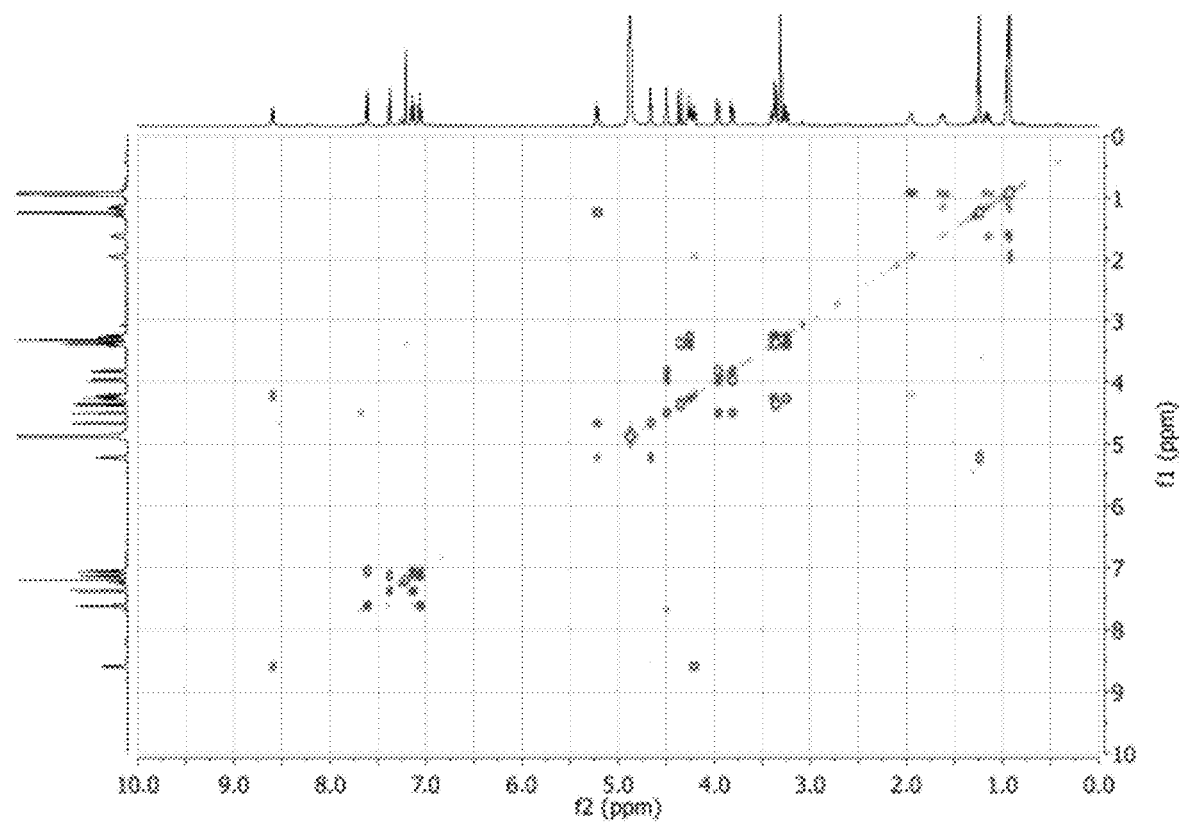
Figure 24D:
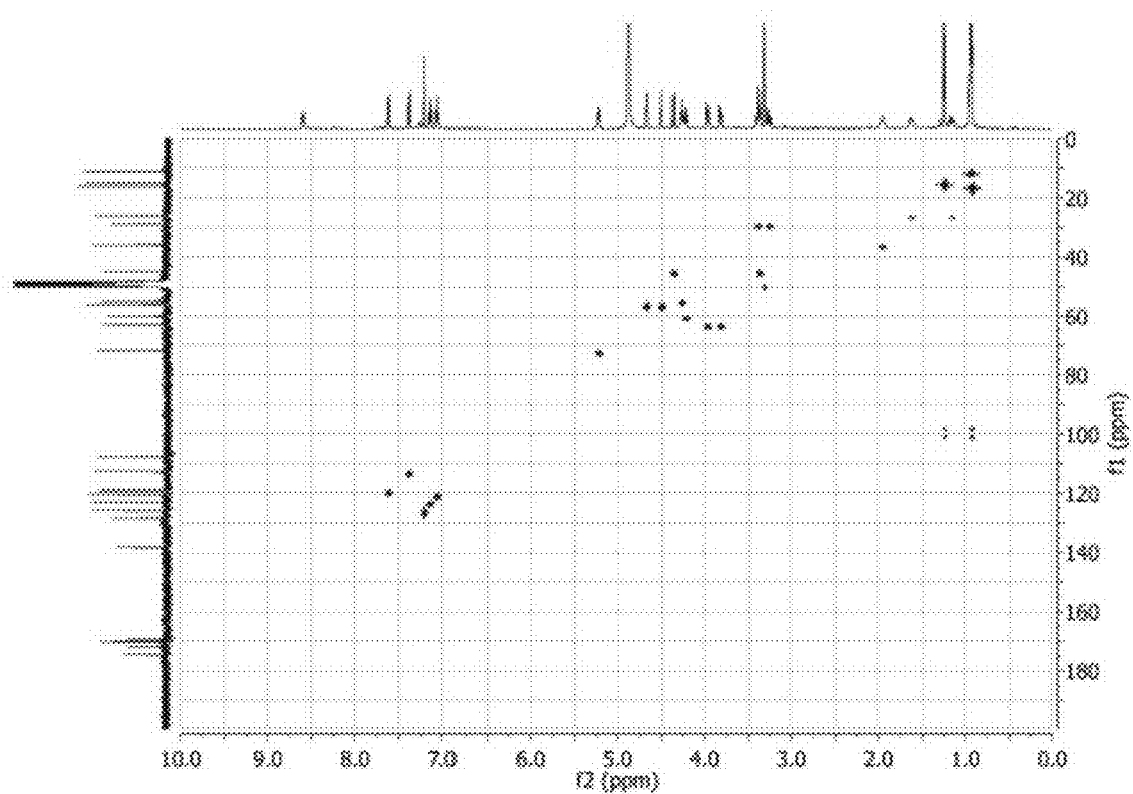
Figure 24E:
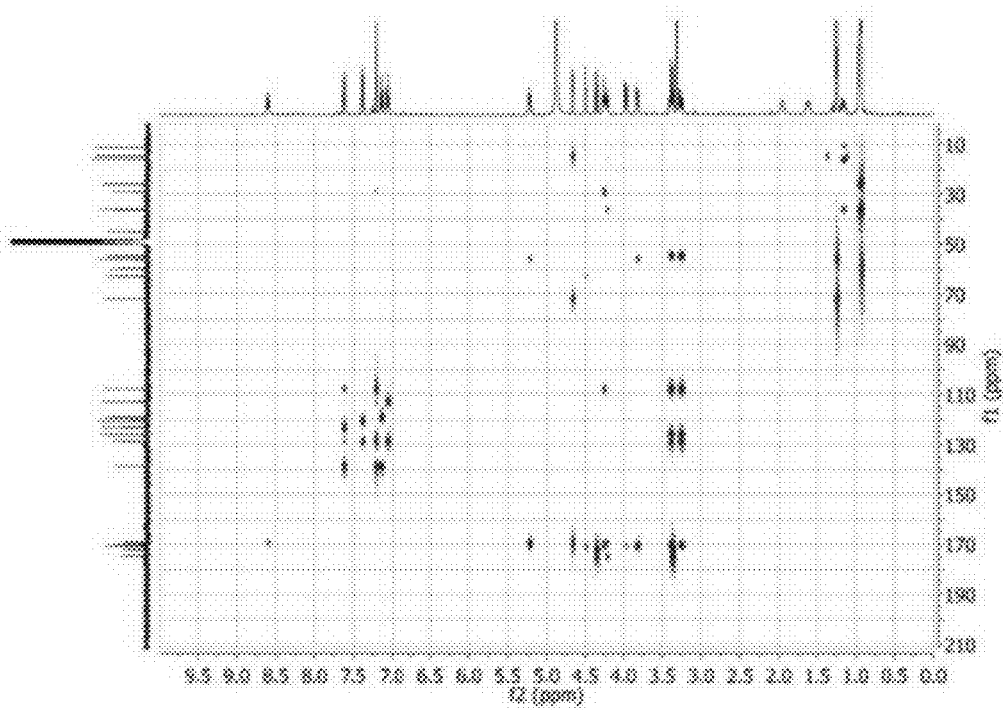

FIGS. 24a-24e show: FIG. 24a $^1$HNMR of 4 (CD$_3$OD, 500 MHz); FIG. 24b $^{13}$NMR of 4 (CD$_3$OD, 100 MHz); FIG. 24c $^1$H-$^1$H COSY of 4 (CD$_3$OD, 500 MHz); FIG. 24d $^1$H-$^{13}$C HSQC of 4 (CD$_3$OD, 500 MHz); FIG. 24e $^1$H-$^{13}$C HMBC of 4 (CD$_3$OD, 500 MHz).

BRIEF DESCRIPTION OF THE SEQUENCES

SEQ ID NO: 1: Sequence of brevicidine (also referenced herein 1 or Compound 1)
SEQ ID NO: 2: Sequence of laterocidine (also referenced herein as 2 or Compound 2)

DETAILED DESCRIPTION OF THE INVENTION

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

"Treatment" or "treating" (and grammatical variants of these terms), as used herein, refer to an approach for obtaining beneficial or desired results including but not limited to therapeutic benefit. A therapeutic benefit is achieved with the eradication or amelioration of one or more of the physiological symptoms associated with the underlying infection such that an improvement is observed in the subject, notwithstanding that the subject may still be afflicted with the underlying infection.

The term "effective amount" or "therapeutically effective amount" refers to that amount of a CNRP or a salt thereof that is sufficient to effect treatment of the infection. The therapeutically effective amount may vary depending upon the intended application, the subject, and the infection being treated, e.g., the weight and age of the subject, the severity of the infection, the manner of administration and the like. The specific dose will vary depending on the particular dosing regimen to be followed, whether it is administered in combination with other compounds, timing of administration, the tissue to which it is administered, and the physical delivery system in which it is carried.

A "sub-therapeutic amount" of a CNRP or a salt thereof is an amount less than the effective amount for a CNRP or a salt thereof but which when combined with an effective or sub-therapeutic amount of another agent or therapy can produce a desired result, due to, for example, synergy in the resulting efficacious effects (e.g., therapeutic benefit) for the subject, or reduced side effects associated with the compounds administered to the subject.

A "synergistically effective" therapeutic amount or "synergistically effective" amount of a CNRP or a salt thereof is an amount which, when combined with an effective or subtherapeutic amount of another agent or therapy, produces a greater effect than when either of the two agents are used alone. A synergistically effective therapeutic amount of a CNRP or a salt thereof produces a greater effect when used in combination than the additive effects of each of the two agents or therapies when used alone. The term "greater effect" encompasses not only a reduction in symptoms of the infection to be treated, but also reduced side effects, improved tolerability, improved subject compliance, improved efficacy, or any other improved clinical outcome.

As used herein, "therapeutic agent" refers to a CNRP or a salt thereof. The salts can be with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in a CNRP or a salt thereof is either replaced by a metal ion, e.g., an alkali metal ion, an alkaline earth ion, a selenium ion or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like.

The terms "co-administration," "administered in combination with," and their grammatical equivalents encompass administration of two or more agents to a subject so that both agents and/or their metabolites are present in the subject at the same time. Co-administration includes simultaneous administration in separate compositions, administration at different times in separate compositions, or administration in a composition in which both agents are present. Co-administered agents may be in the same formulation. Co-administered agents may also be in different formulations.

A "therapeutic effect," as used herein, encompasses a therapeutic benefit as described above. This includes delaying the appearance of an infection, delaying the onset of symptoms of an infection, slowing, halting, or reversing the progression of an infection, or any combination thereof.

"Pharmaceutically acceptable carrier" or "pharmaceutically acceptable excipient" includes any and all solvents, dispersion media, coatings, antibacterial and antifungal agents, isotonic, and absorption delaying agents, and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. Non-limiting examples of subjects include canine, porcine, rodent, feline, bovine, poultry, equine, human, and a non-human primate.

The increasing incidence of infection caused by multidrug-resistant Gram-negative pathogens, especially, colistin-resistant pathogens, threatens to overwhelm healthcare practices worldwide. This disclosure utilizes global genome mining to systematically investigate bacterial CNRPs and provide targeted discovery of CNRPs based on genome sequencing. The successful demonstration of the antimicrobial efficacy of two novel CNRPs against Gram-negative pathogens, especially, colistin-resistant pathogens and identifies bacterial CNRPs as a new source of antibiotics against Gram negative bacteria. The identification of antibiotics against Gram-negative bacteria through the global genome mining of CNRPs provides a powerful strategy for discovering suitable drug candidates to combat antibiotic resistance in Gram-negative pathogens.

Figure 1:
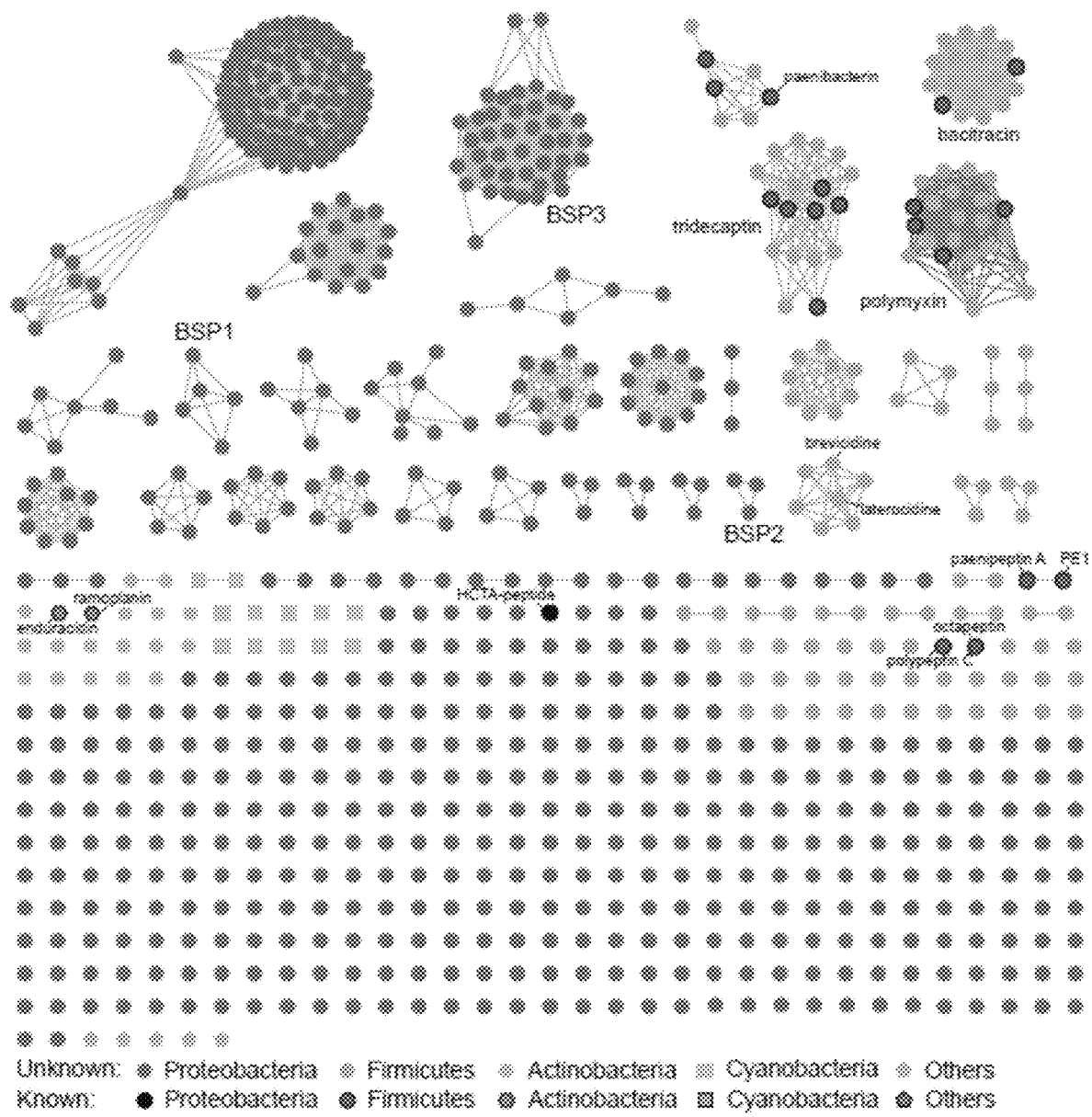
FIG. 1 shows a peptide similarity network of the CNRPs showing their diversity, distribution, and discovery status. The majority of CNRPs remains unexplored, particularly the ones in the Firmicutes and Proteobacteria.
Figure 5A:
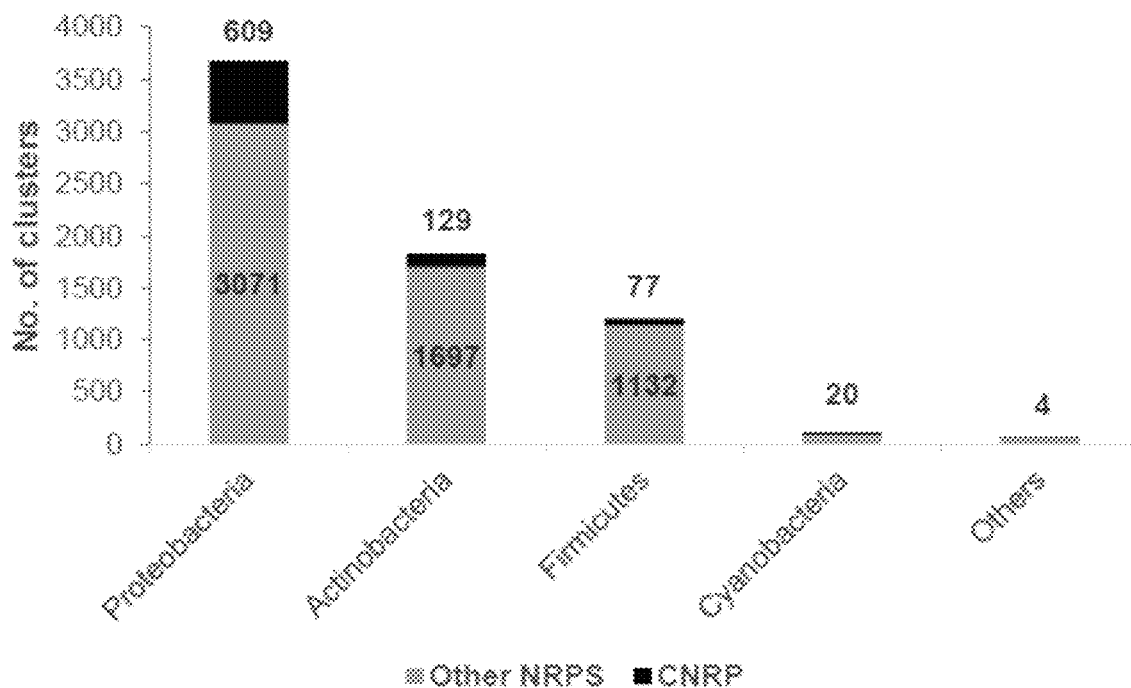
FIGS. 5a-5b show the phylogenetic distribution of CNRP BGCs in bacteria revealed by global genome mining.
Figure 5B:
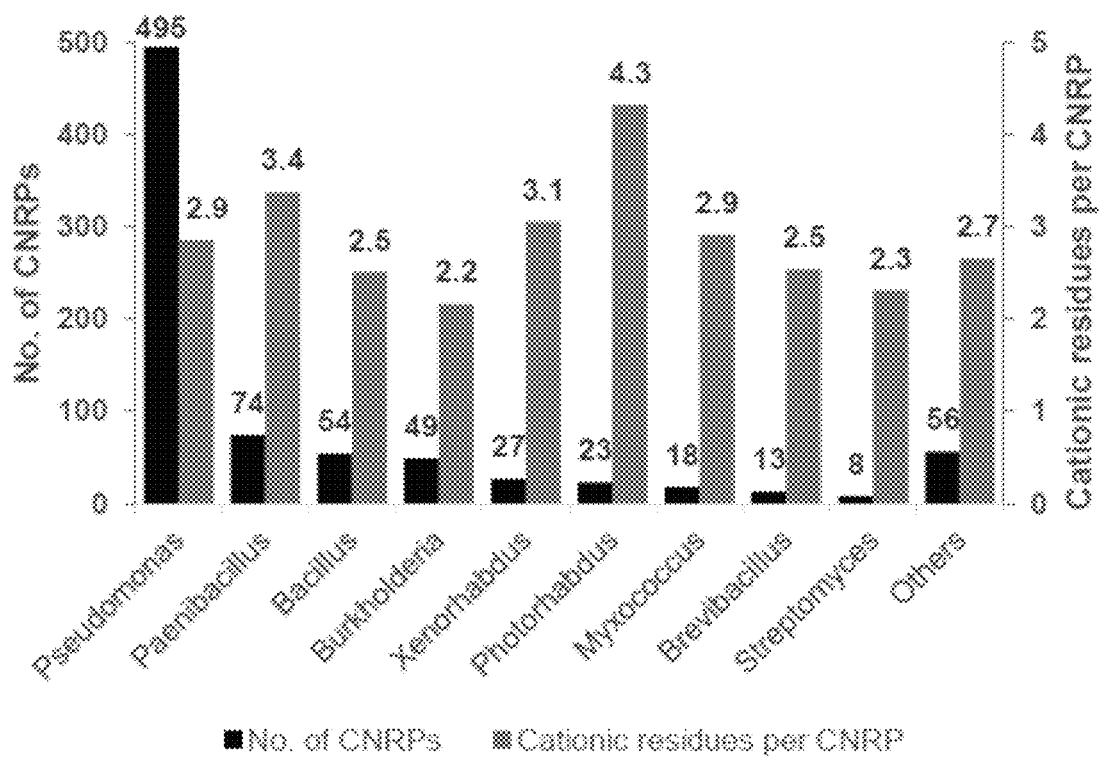
Figure 6A:
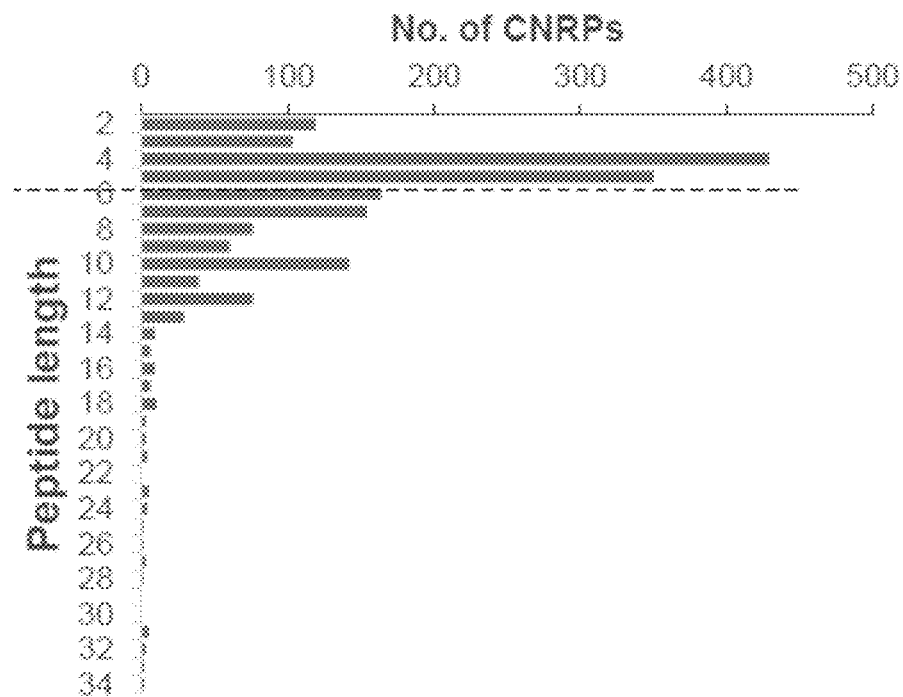
FIGS. 6a-6b show the diversity of CNRPs revealed by global genome mining of 7,395 bacterial genomes.
Figure 6B:
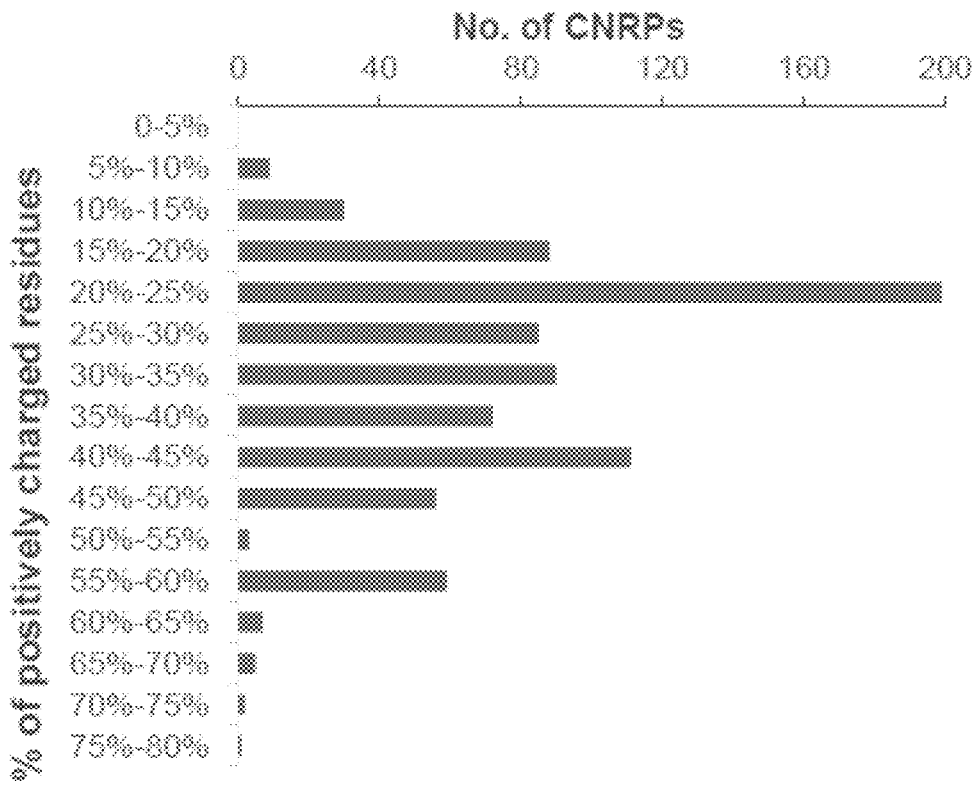

To gain insight into the diversity of bacterial CNRPs, 7,395 bacterial genomes were bioinformatically analyzed for biosynthesis gene clusters (BGCs) encoding CNRPs. 8,567 BGCs encoding nonribosomal peptides (NRPs) with positively-charged residues were detected and 2,676 of them were putative CNRPs containing two or more positively-charged residues. BGC analysis of these putative CNRPs excluding peptides with N-formyl-N—OH-Lys/Orn residues (i.e., siderophores) or shorter peptides led to the identification of 817 CNRPs (≥6 residues, ≥2 positively-charged residues), which were extremely diverse and widely distributed in bacteria (FIGS. 5a-5b). The length of putative CNRPs varied from 6 to 34 with an average of 9.7 (median 9), while their percentage of positively-charged residues ranged from 6.3% to 78.6% with an average of 33.0% (median 30.0%) (FIGS. 6a-6b). Using a sequence similarity networking algorithm genetically encoded CNRPs were classified on the basis of predicted peptide sequence, visualizing their diversity, distribution, and discovery status (FIG. 1). It immediately became apparent that the majority of CNRPs remained unexplored, most of which were mainly harbored in Proteobacteria and Firmicutes. Among the 817 selected cationic peptides, 495 were from the genus *Pseudomonas*, most of which did not have any isolated members.

Figure 2A:
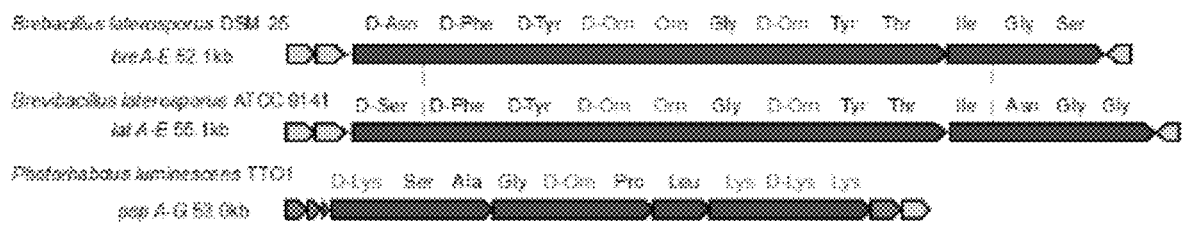
FIGS. 2a-2b show cationic antibacterial peptides discovered via global genome mining.
Figure 2B:
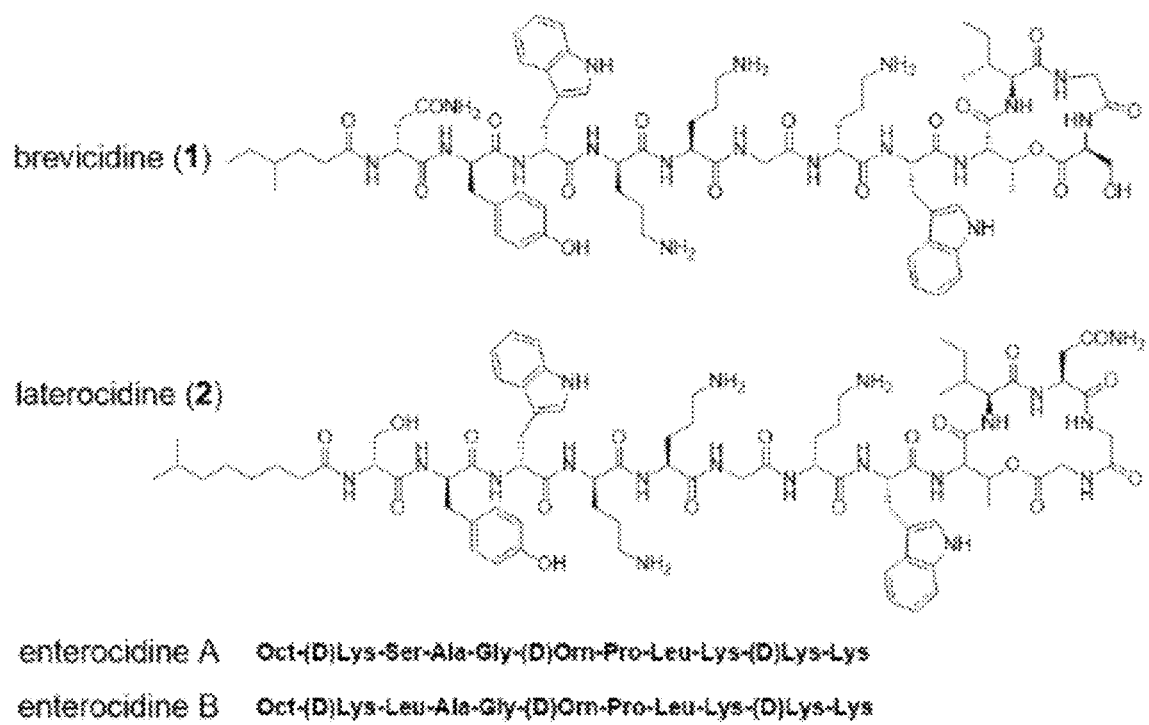
Figure 4:
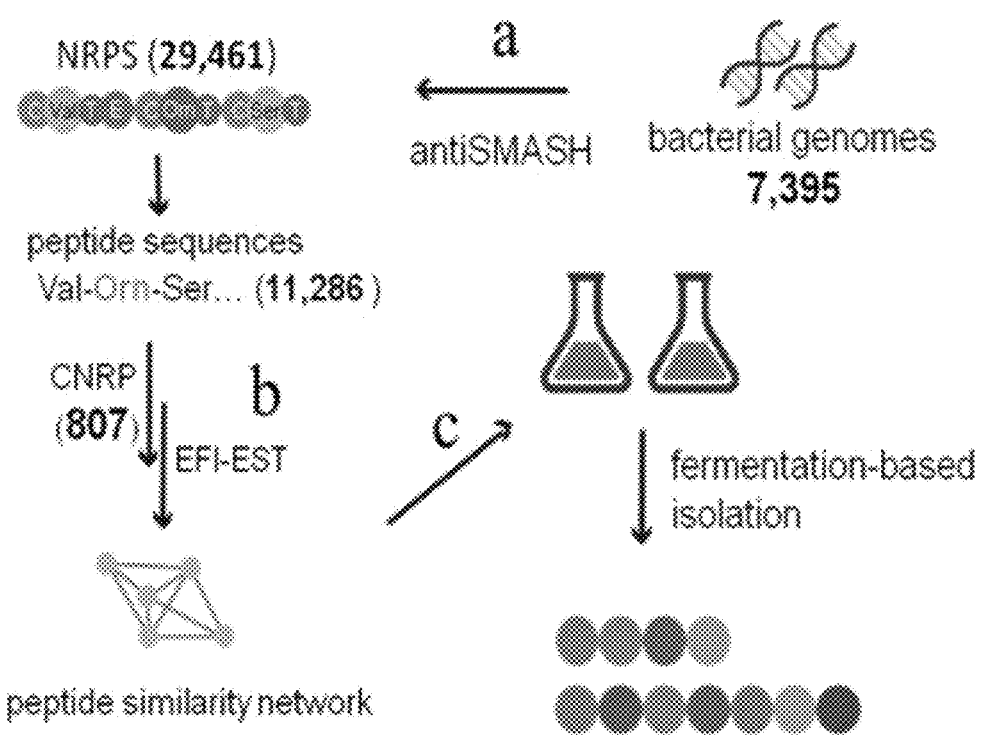
FIG. 4 shows computational workflow of global genome mining of CNRP BGCs. Step a) 7,395 complete or draft bacterial genomes were downloaded from GenBank and subjected to standalone antiSMASH for BGC analysis and NRP sequence prediction, leading to the identification of 29,461 NRP BGCs, in which 817 encoded CNRPs whose lengths were equal to or greater than 6. Step b) Predicted peptide sequences were submitted to the EFI-ENZYME SIMILARITY TOOL (EFI-EST) for constructing the peptide similarity network. Step c) The CNRPs with desirable chemical features were obtained by either traditional fermentation-based isolation or BGC inspired synthesis.
Figure 7:
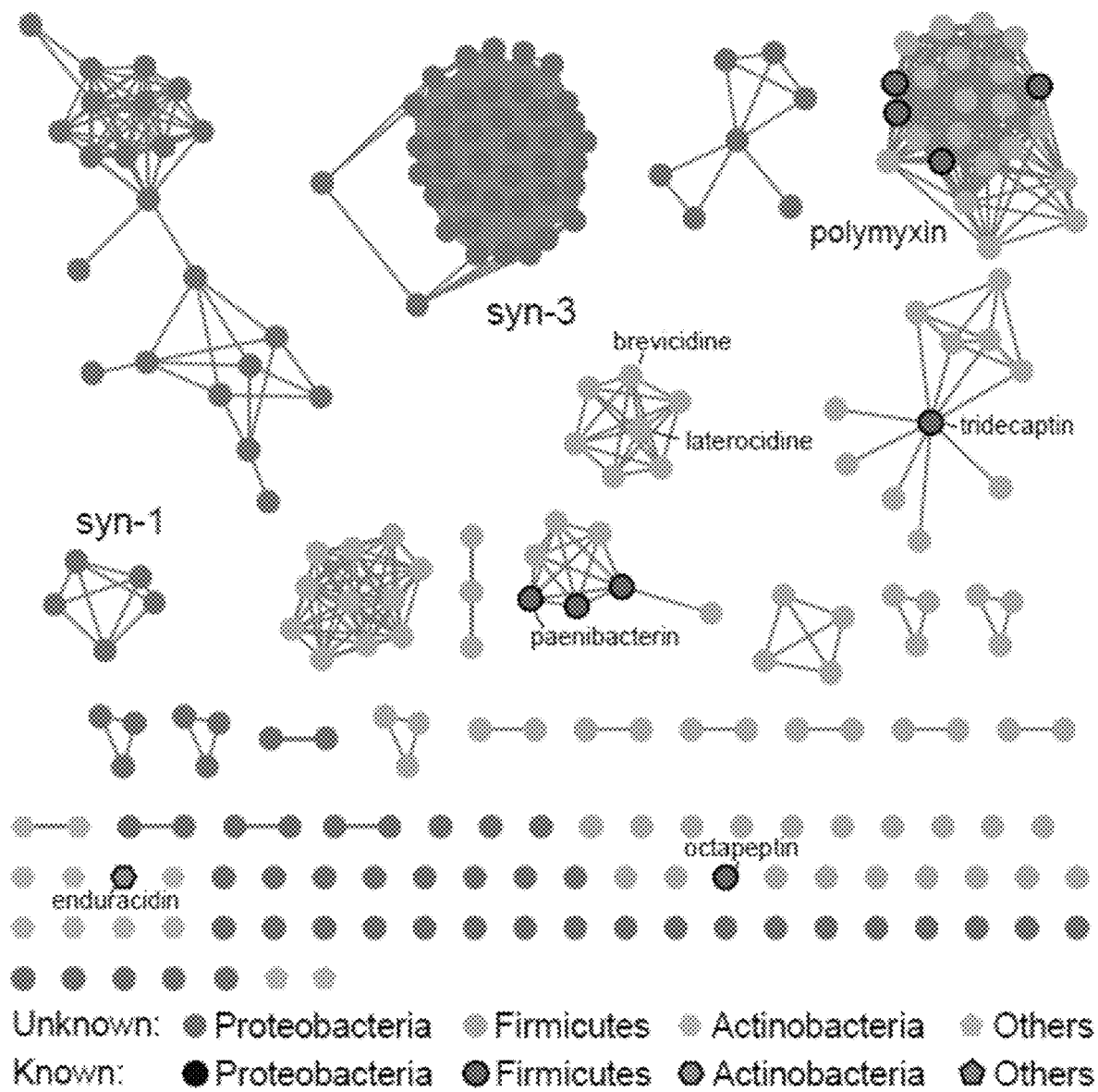
FIG. 7 shows a sequence similarity network of N-acylated CNRPs (cationic lipopeptides) showing their diversity, distribution, and discovery status. Clearly, the majority of N-acylated CNRPs remain unexplored.
Figure 8:
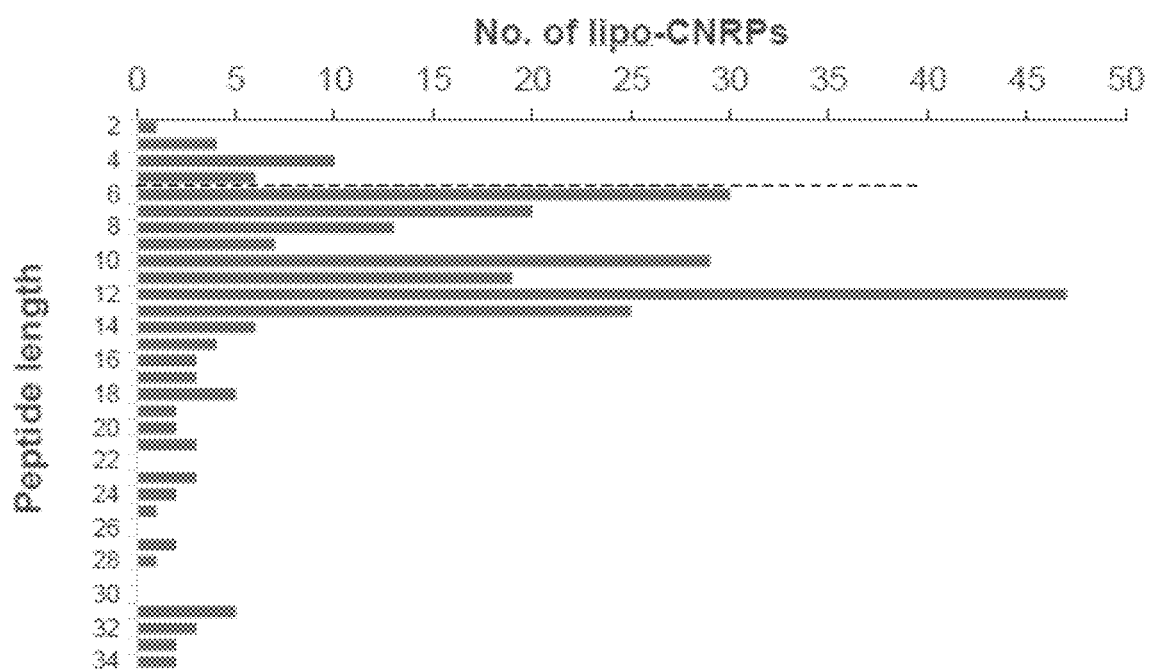
FIG. 8 shows the diversity of putative N-acylated CNRPs (cationic lipopetides) in terms of peptide length. CNRPs with a condensation starter domain (Cs) in their BGCs were considered as N-acylated CNRPs. The length of N-acylated CNRPs (n=260) varied from 2 to 34, with an average of 11.7 and a median of 11. Below the dotted line (length≥6) are N-acylated CNRPs (n=239) that exist in the sequence similarity network (See FIG. 8). These N-acylated CNRPs have an average length of 12.38 and a median length of 12.
Figure 9A:
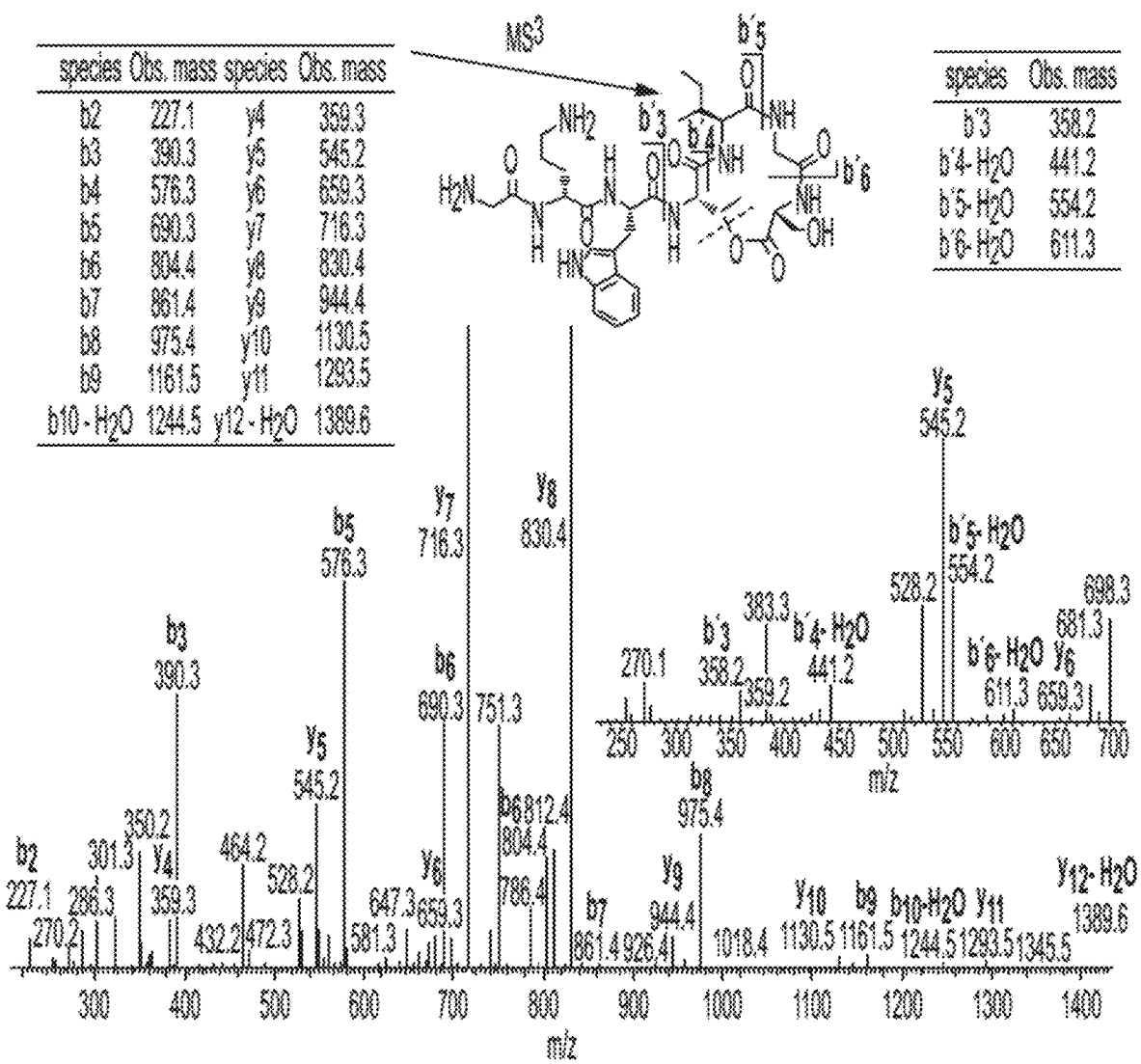
Figure 9B:
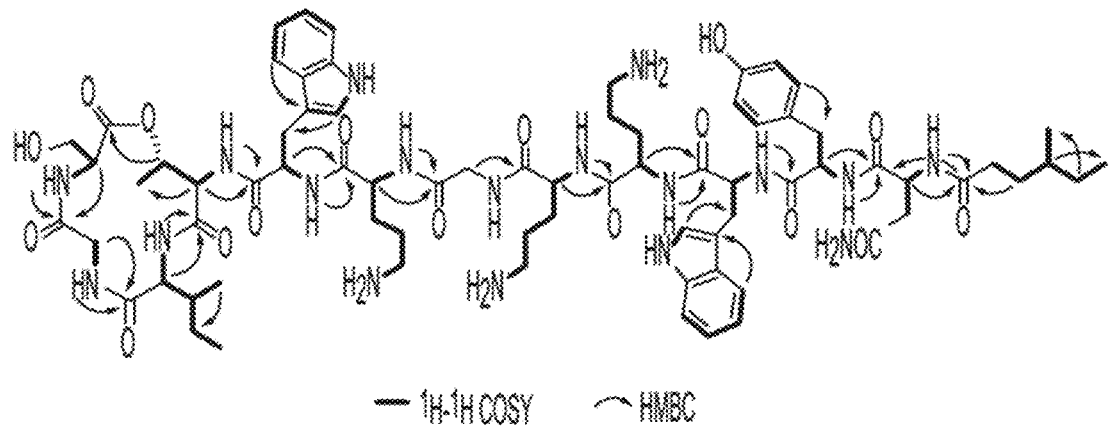

Traditional fermentation-based isolation was then carried out to discover CNRPs with the potential to kill Gram-negative pathogens (FIG. 4). N-acylated CNRPs, also known as cationic lipopeptides including polymyxin and tridecaptin, were very effective against infections caused by Gram-negative pathogens, representing a growing family of attractive antibiotics candidates (FIGS. 7-8). The follow-up screening was then focused on putative cationic lipopeptides with three or more positively-charged residues, as positively-charged residues enable electrostatic interaction with negatively-charged cell membranes while the hydrophobic acyl chain defines membranolytic and cell-penetrating properties. While bacilli are well-known producers of CNRP antibiotics, *Brevibacillus laterosporus* DSM 25, ATCC 9141 and *Paenibacillus alvei* DSM 29 of this class that harbored the desired BGCs were selected for traditional fermentation-based discovery (FIGS. 2a-2b). Cationic lipopeptides and their derivatives were subsequently isolated from three strain cultures on the basis of genome mining and metabolic analysis and characterized structurally by MS/MS, NMR and Marfey-type analyses (FIGS. 2a-2b and 9-11). These CNRPs, named brevicidine (1), laterocidine (2), and paenibacterin B (3), were new cyclic depsipeptides with an N-acylated side chain and a lactone ring that formed through the condensation of a C-terminal residue with a threonine (Thr) residue. Paenibacterin B was a new derivative of paenibacterin (FIGS. 11a-11c), which is a bactericidal antibiotic binding to bacterial outer membrane. Brevicidine and laterocidine were a new class of CNRPs exhibiting three key structural features: a hydrophobic N-terminal fatty acyl chain; a linear cationic segment with three positively-charged ornithine residues, and a hydrophobic tetrapeptide/pentapeptide ring (FIG. 2b). Predicted biosynthesis of brevicidine started with a typical starting module for N-acylated NRPs with a condensation starter domain that acylates the first amino acid with a fatty acid. In accordance with the co-linearity rule, the other 12 amino acids, including positively-charged residues (D-Orn$_4$, L-Orn$_5$, D-Orn$_7$) were introduced into the linear peptide and the ring closure between the last Ser$_{12}$ and Thr$_9$ was catalyzed by a thioesterase domain during product offloading (FIGS. 12a-12b). A similar biosynthetic assembling line was also followed by the laterocidine biosynthesis pathway (FIGS. 13a-13b).

Figure 3A:
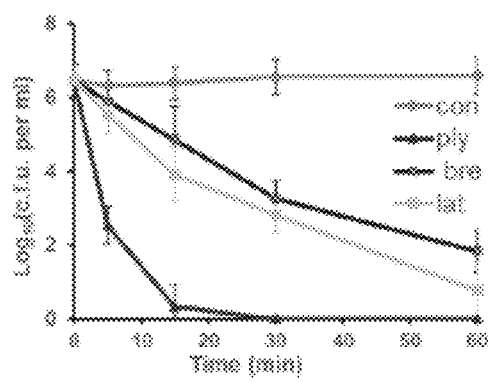
FIGS. 3a-3f show that brevicidine and laterocidine have bactericidal activity, a low risk of resistance, and efficacy in a mouse thigh infection model.
Figure 3B:
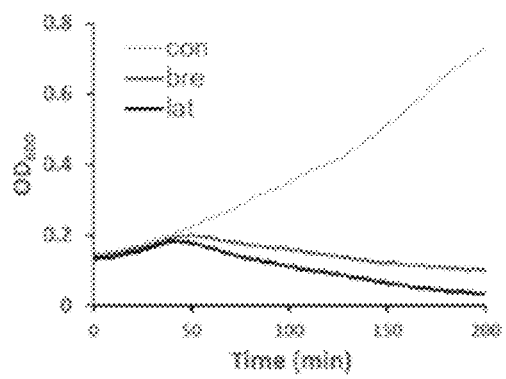
Figure 3C:
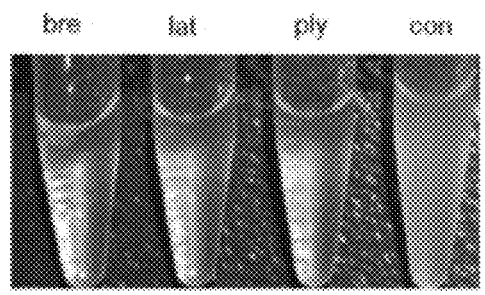

All of the isolated compounds 1-11 (Table 4) were assessed for bioactivities against ESKAPE bacteria which cause the majority of hospital-acquired infection. Both brevicidine and laterocidine exhibited broad antibacterial activities against Gram-negative bacteria including opportunistic pathogens such as difficult-to-treat *Pseudomonas aeruginosa* and colistin-resistant *E. coli*. Minimal inhibitory concentration (MIC) values in the micromolar range (1-16 μg mL$^{-1}$; 0.66-10.5 μM) testified to their high potency. Furthermore, their activities were not impaired in the presence of fetal bovine serum (Table 1). Preliminary structure-activity relationship study suggested that both the linear cationic segment and the hydrophobic lactone ring were crucial for their activities. For example, the lack of either the lactone ring or the cationic side chain increased MIC values 8- to 32-fold (1 vs. 4-5, 2 vs. 9-11) (Table 2). The two CNRPs 1 and 2 were bactericidal against *E. coli* as revealed by the growth kinetics of *E. coli*, time-kill assay, and lysis assay (FIGS. 3a-3c). They neither caused lysis of erythrocytes nor showed significant toxicity against the human cell line HeLa at concentration up to 128 μg mL$^{-1}$ (FIGS. 15a-15b), suggesting 1-2 as promising candidates as Gram-negative antibiotics.

TABLE 1

Activity of CNRPs against microorganisms

| | MIC (μg/ml) | | | |
| --- | --- | --- | --- | --- |
| Target species | 1 | 2 | polymyxin B | colistin |
| *Escherichia coli* ATCC 25922 | 2 | 2 | 1 | 2 |
| Colistin-resistant *E. coli*[a] | 2 | 2 | 16 | 16 |
| *E. coli* ATCC 25922 + 10% serum | 2-4 | 2-4 | 1-2 | 2-4 |
| *E. coli* ATCC 25922 + Mg$^{2+}$ (21 mM) | >64 | >64 | >64 | >64 |
| *E. coli* ATCC 25922 + LPS (1.0 mg L$^{-1}$) | >64 | >64 | >64 | >64 |
| *E. coli* Top10 | 2 | 2 | 2 | 2 |
| *Pseudomonas aeruginosa* PAO1 | 1 | 2 | 1 | 1 |
| *Acinetobacter baumannii* | 16 | 4 | 4 | |
| *Klebsiella pneumoniae* NRRL-B-408 | 2 | 4 | 16 | |
| *K. pneumoniae* NRRL-B-3521 | 4 | 4 | 2 | |
| *Enterobacter cloacae* NRRL-B-413 | 2 | 2 | 8 | |
| *E. cloacae* NRRL-B-425 | 2 | 3 | 64 | |
| *Bacillus subtilis* 168 | 32 | 32 | 4 | |
| *Candida albicans* | >64 | >64 | >64 | |
| *Saccharomyces cerevisiae* | >64 | >64 | >64 | |
| *Staphylococcus aureus* (MRSA) | >64 | >64 | 32 | |

[a] *E. coli* ATCC 25922 carrying mcr-1.

TABLE 2

Antimicrobial activities of CNRPs and their derivatives. Bacterial strains (MIC/μg · mL$^{-1}$)

| Comp. | Ec | Pa | Ab | Kp | En | Bs | MRSA | Ca | Sc |
| --- | --- | --- | --- | --- | --- | --- | --- | --- | --- |
| 1 | 2 | 1 | 16 | 2 | 2 | 32 | ND | ND | ND |
| 2 | 2 | 2 | 4 | 4 | 2 | 32 | ND | ND | ND |
| 4 | ND | ND | ND | ND | ND | ND | ND | ND | ND |
| 5 | ND | ND | ND | ND | ND | ND | ND | ND | ND |
| 6 | ND | ND | — | — | — | ND | ND | — | — |
| 7 | ND | ND | — | — | — | ND | ND | — | — |
| 8 | ND | ND | — | — | — | ND | ND | — | — |
| 9 | ND | ND | — | — | — | ND | ND | — | — |
| 10 | ND | ND | — | — | — | ND | ND | — | — |
| 11 | 16 | 8 | — | — | — | ND | ND | — | — |
| Polymyxin | 1 | 1 | 4 | 16 | 8 | 4 | 32 | ND | ND |

Ec = *Escherichia coli* ATCC 25922,
Pa = *Pseudomonas aeruginosa* PAO1,
Ab = *Acinetobacter baumannii*,
Kp = *Klebsiella pneumoniae* NRRL-B-408,
En = *Enterobacter cloacae* NRRL-B-413,
Bs = *B. subtilis* 168,
MRSA = Methicillin-resistant *Staphylococcus aureus* ATCC 43300,
Ca = *Candida albicans*,
Sc = *Saccharomyces cerevisiae* VL-48,
ND >64 μg/ml.

Figure 3D:
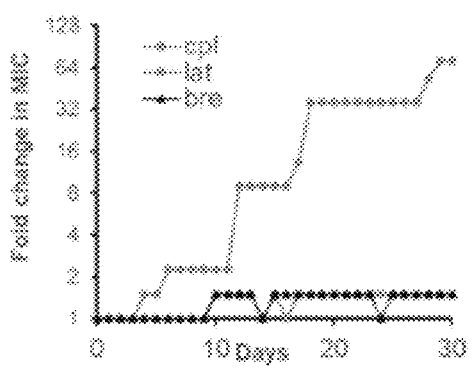

To explore the mode of action of compounds 1-2, attempts were made to identify *E. coli* ATCC 25922 resistant mutants. Interestingly, development of resistance was not observed in *E. coli* during continuous serial passaging in the presence of subinhibitory concentrations of either 1 or 2 over 30 days (FIG. 3d). In contrast, *E. coli* rapidly developed resistance to ciprofloxacin within a few days of exposure (FIG. 3d).

Figure 3E:
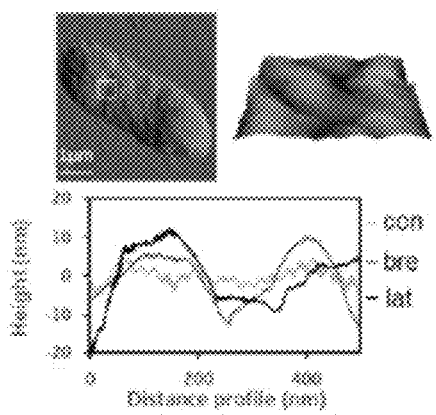
Figure 3F:
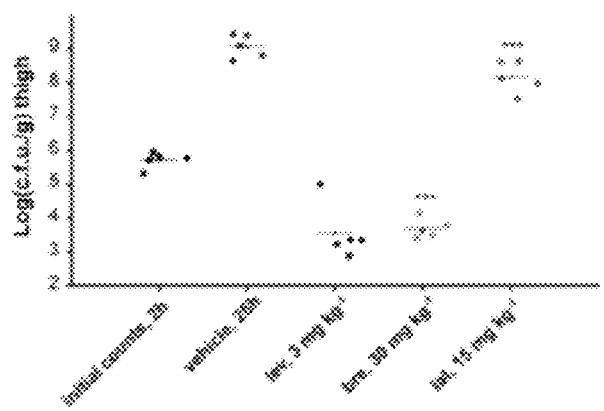

Neither 1 nor 2 exhibited antibiotic effect when cells were grown in the presence of exogenous lipopolysaccharide (LPS) or a high concentration of $Mg^{2+}$ (Table 1), suggesting that these cationic peptides disrupted the integrity of the outer membrane through association with LPS. This suggestion was further supported by atomic force microscopy (AFM) and isothermal titration calorimetry (ITC) analysis. AFM analysis of *E. coli* ATCC25922 and *P. aeruginosa* PAO1 treated with compound 1 or 2 showed that treated cells lost their regular rod-like shape and became lumpy and rugged (FIGS. 3e and 16-17). The morphology of compound-treated cells was extensively disrupted as characterized by undulations on the order of approximately 30 nm in amplitude, whereas untreated *E. coli* remained uniform. Indeed, compound 1 displayed high affinity for LPS in vitro (dissociation constant $K_d$ of 6.5 µM), similar to polymyxin B (FIGS. 18a-18b). Notably, antibacterial activities of both brevicidine and laterocidine were retained upon colistin-resistance *E. coli* ATCC 25922 carrying mcr-1[22] (Table 1), suggesting that the action of the two CNRPs was independent of phosphoethanolamine modifications on lipid A. The growth kinetics of *E. coli* cells showed that cells exposed to compound 1 or 2 grew at a reduced rate for 30 min, after which a steady decrease in cell count was observed (FIG. 3a). These data were different from that of polymyxin, which are generally bactericidal within minutes of exposure due to the formation of large, nonspecific pores in the bacterial membrane. *E. coli* cells exposed to 1 or 2 at 10 times the MIC in the time-kill assays showed slightly reduced cell viability after 15 min of exposure, and a significant reduction after 30 min. Polymyxin B acted more quickly, significantly reducing the viable cell population after 5 min and killing all cells within 30 min. These results suggested that compounds 1-2 were membrane targeting bactericidal peptides, but did not act through a generic membrane lysis mechanism like polymyxin B. This argument was further supported by the selectivity of the two CNRPs against Gram-negative bacteria (Table 1) because a bactericidal that functions through a generic lysis mechanism would also target Gram-positive organisms. No significant membrane disruption of compounds 1-2 was observed at concentrations of two times MIC, suggesting that potential intracellular targets exist for the two CNRPs. Given the low resistance risk and attractive mode of action of 1-2, an animal efficacy study was then performed in a mouse thigh model. Mice were intramuscularly infected with $1.50 \times 10^6$ c.f.u. of *E. coli* ATCC 25922. Two hour post-infection, brevicidine (30 mg/kg) or laterocidine (15 mg/kg) was introduced subcutaneously injected at two doses. Levofloxacin (MIC=0.032 µg/ml) was dosed at 3.0 mg/kg as a positive control. The compounds 1-2 showed potent bactericidal efficacy in a neutropenic mouse thigh infection model against *E. coli*. In particular, 1 was highly efficacious in mice infected with *E. coli*, causing a 5 $\log_{10}$ reduction of c.fu. in thigh compared to the vehicle control at 24 h (FIG. 3f).

Accordingly, certain embodiments of the invention provide a pharmaceutical composition comprising a cationic nonribosomal peptide (CNRP) or a salt thereof. The pharmaceutical composition of the invention can also contain a pharmaceutically acceptable carrier or excipient. In preferred embodiments, the CNRP is brevicidine (SEQ ID NO: 1) or laterocidine (SEQ ID NO: 2).

The salts of a CNRP that can be used in the compositions of the invention include salts of an CNRP with an acid selected from hydrochloric acid, hydrobromic acid, perchloric acid, nitric acid, thiocyanic acid, sulfuric acid, phosphoric acid, trifluoroacetic acid (TFA), formic acid, acetic acid, propionic acid, lactic acid, pyruvic acid, oxalic acid, malonic acid, succinic acid, maleic acid, and fumaric acid, hexanoic acid, cyclopentanepropionic acid, glycolic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. The salts of a CNRP can also be with a base selected from sodium hydroxide, ammonium hydroxide, potassium hydroxide, monoalkyl amine, dialkyl amine, trialkyl amine, aryl amine, ammonium, and tetraalkylammonium; or with a metal selected from sodium, potassium, calcium, and magnesium.

Further embodiments of the invention provide a method of treating a bacterial infection, comprising administering to a subject in need thereof, the composition comprising a CNRP or a salt thereof. The aspects of the invention disclosed above in connection with pharmaceutical compositions comprising a CNRP or a salt thereof are also applicable to the methods of the invention and such embodiments are within the purview of the invention.

In some embodiments, the infection being treated is caused by a Gram-negative bacterium. In preferred embodiments, the Gram-negative bacterium is resistant to an antibiotic selected from an aminoglycoside, carbapenem, monobactam, colistin, cephalosporin, penicillin, macrolide, quinolone, sulfonamide/thrimethoprim, and chloramphenicol. Thus, certain embodiments of the invention provide methods of treating an infection caused by a Gram-negative bacterium which cannot be effectively treated with conventional antibiotics.

Non-limiting examples of Gram-negative bacteria that can cause the infections to be treated according to the methods of the invention include bacteria belonging to a genus selected from *Acinetobacter, Actinobacillus, Bordetella, Brucella, Campylobacter, Cyanobacteria, Enterobacter, Erwinia, Escherichia, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio*, and *Yersinia*.

In more preferred embodiments, the antibiotic is effective against a Gram-positive bacterium and is not effective against a Gram-negative bacterium. The phrase "an antibiotic that is effective against a Gram-positive bacterium and not effective against a Gram-negative bacterium" refers to an antibiotic that is not as active against Gram-negative bacteria as it is against Gram-positive bacteria. Preferably, such antibiotic is not active against *E. coli* to the same extent that it is active against *Staphylococcus aureus*. Non-limiting examples of such antibiotics include a glycopeptide (e.g., vancomycin and teicoplanin), glycolipopeptide (e.g., oritavancin, dalbavancin, and telavancin), lipopeptide (e.g., daptomycin), methicillin, oxazolidinones (e.g., chloramphenicol, clindamycin, and linezolid), tedizolid, flucloxacillin, and fluoroquinolone. These antibiotics are not typically used to treat an infection by a Gram-negative bacterium, where antibiotics that are more active against Gram-negative bacteria are used. Antibiotics typically used against Gram-negative bacteria include aminoglycosides, carbapenems, monobactams, colistins, cephalosporins, penicillins, macrolides, quinolones, sulfonamide/thrimethoprims, and chloramphenicols.

In more preferred embodiments, the antibiotic is effective against a Gram-positive bacterium. In further embodiments, the antibiotic is effective against a Gram-positive bacterium and not effective against a Gram-negative bacterium. The antibiotics discussed above that are effective against Gram-positive bacteria and not effective against Gram-negative bacteria can be used in the methods of the invention. Non-limiting examples of such antibiotics include a glycopeptide (e.g., vancomycin and teicoplanin), glycolipopeptide (e.g., oritavancin, dalbavancin, and telavancin), lipopeptide (e.g., daptomycin), methicillin, oxazolidinones (e.g., chloramphenicol, clindamycin, and linezolid), tedizolid, flucloxacillin, and fluoroquinolone.

In preferred embodiments, the Gram-negative bacterium that caused the infection is resistant to an antibiotic selected from an aminoglycoside, carbapenem, monobactam, colistin, cephalosporin, penicillin, macrolide, quinolone, sulfonamide/thrimethoprim, and chloramphenicol. Thus, certain embodiments of the invention provide improved methods of treating infections caused by Gram-negative bacteria that cannot be effective treated with the conventional antibiotics.

In preferred embodiments, the Gram-negative bacterium that causes the infection to be treated according to the methods disclosed herein belongs to a genus selected from *Acinetobacter, Actinobacillus, Bordetella, Brucella, Campylobacter, Cyanobacteria, Enterobacter, Erwinia, Escherichia, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio*, and *Yersinia*.

The terms "simultaneous" or "simultaneously" as applied to administering agents to a subject refer to administering one or more agents at the same time, or at two different time points that are separated by no more than 1 hour.

The term "sequentially" refers to administering more than one agent at two different time points that are separated by more than 1 hour, e.g., about 2 hours, about 5 hours, 8 hours, 1 day, 2 days, 3 days, 4 days, 5 days, 6 days, 7 days or longer.

Routes of Administration and Dosage Forms

In certain embodiments, a CNRP or a salt thereof may be administered intramuscularly, subcutaneously, intrathecally, intravenously or intraperitoneally by infusion or injection. Solutions of a CNRP or a salt thereof can be prepared in water, optionally mixed with a nontoxic surfactant. Under ordinary conditions of storage and use, these preparations can contain a preservative to inhibit the growth of microorganisms.

The pharmaceutical dosage forms suitable for injection or infusion can include sterile aqueous solutions or dispersions or sterile powders comprising a CNRP or a salt thereof that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating a CNRP or a salt thereof in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder a CNRP or a salt thereof plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the subject's diet. For oral therapeutic administration, a CNRP or a salt thereof may be combined with one or more excipients and used in the form of ingestible tablets, buccal tablets, troches, capsules, elixirs, suspensions, syrups, wafers, and the like. Such compositions and preparations should contain at least 0.1% of a CNRP or a salt thereof. The percentage of a CNRP or a salt thereof present in such compositions and preparations may, of course, be varied and may conveniently be between about 2% to about 60% of the weight of a given unit dosage form. The amount of a CNRP or a salt thereof in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain a CNRP or a salt thereof and sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, a CNRP or a salt thereof may be incorporated into sustained-release preparations and devices. For example, a CNRP or a salt thereof may be incorporated into time release capsules, time release tablets, time release pills, and time release polymers or nanoparticles.

Pharmaceutical compositions for topical administration of a CNRP or a salt thereof to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which a CNRP or a salt thereof can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions that can be used to deliver a CNRP or a salt thereof to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of a CNRP or a salt thereof in such formulations can vary widely depending on the nature of the formulation and intended route of administration. For example, the concentration of a CNRP or a salt thereof in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises a CNRP or a salt thereof and further in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing a CNRP or a salt thereof in further combination with carriers known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise a CNRP or a salt thereof in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising a CNRP or a salt thereof. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of a CNRP or a salt thereof.

A CNRP or a salt thereof may be combined with an inert powdered carrier and inhaled by the subject or insufflated.

Pharmaceutical compositions for administration by inhalation or insufflation can be provided in the form of a dry powder composition, for example, a powder mix of a CNRP or a salt thereof and a suitable powder base such as lactose or starch. Such powder composition can be provided in unit dosage form, for example, in capsules, cartridges, gelatin packs, or blister packs, from which the powder can be administered with the aid of an inhaler or insufflator.

The exact amount (effective dose) of a CNRP or a salt thereof can vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

A CNRP or a salt thereof can be conveniently administered in unit dosage form, containing for example, about 0.05 to about 10000 mg, about 0.5 to about 10000 mg, about 5 to about 1000 mg, or about 50 to about 500 mg of each of a CNRP or a salt thereof.

A CNRP or a salt thereof can be administered to achieve peak plasma concentrations of, for example, from about 0.25 to about 200 µM, about 0.5 to about 75 µM, about 1 to about 50 µM, about 2 to about 30 µM, or about 5 to about 25 µM of each of a CNRP or a salt thereof per unit dosage form. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of a CNRP or a salt thereof optionally in saline, or orally administered as a bolus containing about 1 to about 100 mg of a CNRP or a salt thereof. Desirable blood levels may be maintained by continuous or intermittent infusion.

A CNRP or a salt thereof can be included in the compositions within a therapeutically useful and effective concentration range, as determined by routine methods that are well known in the medical and pharmaceutical arts. For example, a typical composition can include a CNRP or a salt thereof at a concentration in the range of at least about 1 mg/ml, preferably at least about 4 mg/ml, more preferably at least 5 mg/ml and most preferably at least 6 mg/ml of each of a CNRP or a salt thereof.

A CNRP or a salt thereof may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a CNRP or a salt thereof.

Materials and Methods

Global Genome Mining of CNRPS

A total of 5,585 complete bacterial genomes (with cut-off on Oct. 20, 2016) were retrieved from NCBI Genome and subjected to BGC analysis utilizing the standalone version of antiSMASH v3.0.5. 6,879 NRP BGCs were identified from complete bacterial genomes spanning the entire domain of bacteria. To gain insight into the biosynthesis capacity of bacterial CNRPs, a series of scripts were created to collect BGC information from the antiSMASH-annotated files. Costume Node.js scripts were prepared to extract predicted amino acid building blocks from adenylation (A) domains in NRPS gene clusters. Amino acids predicted by Minowa and Stachelhaus code algorisms were collected, and their occurrences in each NRPS gene cluster were counted. After analyzing all complete genomes, the genera were ranked based on their abundance in CNRP BGCs containing two or more positively-charged amino acids (i.e. arginine, histidine, lysine, ornithine, and 2,4-diaminobutyric acid). Draft genomes (1,810) from the top 20 genera as well as all complete genomes were chosen for global genome mining of CNRPs. The top 20 genera were: *Actinoplanes, Alcanivorax, Arthrobacter, Azotobacter, Bacillus, Brevibacillus, Corallococcus, Cyanothece, Kibdelosporangium, Myxococcus, Nitrosomonas, Paenibacillus, Pandoraea, Photorhabdus, Polyangium, Pseudomonas, Saccharothrix, Sorangium, Vibrio*, and *Xenorhabdus*. Peptide sequence similarity networking was performed using the Enzyme Function Initiative-Enzyme Similarity Tool (EFI-EST). In total, 7,395 bacterial genomes were subjected to BGCs analysis, leading to the identification of 29,461 NRPS BGCs. Gene clusters containing protein SMCOG1080 (lysine/ornithine N-monooxygenase) were excluded from this study because their encoding products were mainly NRPS-dependent siderophores with N-formyl-N—OH-Lys/Orn residues. Costume Node.js scripts were developed to interrogate the predicted peptide sequences and convert the amino acids into their abbreviated forms. Non-proteinogenic amino acids were assigned to their proteinogenic counterparts based on their structural similarity or biosynthesis origin (Table 3). For each gene cluster, peptide sequences predicted by two algorisms (Minowa and Stachelhaus code) were concatenated to increase the prediction accuracy. The concatenated peptide sequences of all gene clusters were filtered according to the following rules: number of positively-charged amino acids (K, H and R)≥4 and sequence length≥11. 817 peptide sequences were selected and analyzed by EFI-EST (E-value=10E−3, Fraction=1). The resulting full network was visualized by Cytoscape. In particular, the polymyxin family contains an extremely high proportion of Dab and a limited amino acid composition, which lead to an inaccurate E-value in EFI-EST. Thus, the polymyxin family (23 BGCs) was manually selected and analyzed separately using BLASTP multiple alignment to construct the network (E-value<10E−3).

TABLE 3

Predicted amino acids residues and their assigned short forms.

| Predicted amino acids | Assigned amino acids |
|---|---|
| ala, abu, alaninol, b-ala, dhb, ala-d, apa, cha | A |
| cys | C |
| asp, measp, omasp | D |
| glu, 3mglu, aaa, ahp, aad, aeo | E |
| phe, phenylacetate, qa, sal, phg | F |
| gly, sar | G |
| his | H |
| ile | I |
| lys, 2-3-diaminoproprionate, blys, dab, orn, pip | K |
| leu | L |
| met | M |
| asn, hasn | N |
| pro, mpro, apc | P |
| gln, uda | Q |
| arg, capreomycidine, guanidinoacetic_acid, cit, end, gua | R |

TABLE 3-continued

Predicted amino acids residues and their assigned short forms.

| Predicted amino acids | Assigned amino acids |
|---|---|
| ser, hse | S |
| thr, bmt, thr-4-cl, tcl | T |
| val, hyv | V |
| trp | W |
| tyr, 3-hpa, 4-mha, bht, dhpg, homotyr, hpg, hpg2cl, kyn, qna, dpg, hty | Y |

Both proteogenic and non-proteogenic amino acids predicted by antiSMASH were assigned to their short forms according to Table 3. Non-proteinogenic amino acids were assigned to proteinogenic counterpart based on their structure similarity or biosynthesis origin.

UPLC-MS Analysis and Isolation of Compounds

For metabolic analysis, all samples dissolved in 100 μL of MeOH were analyzed with the ultra-high-performance liquid chromatography (UPLC) system (Waters ACQUITY, with a Waters BEH C18 reversed-phase UPLC column) coupled with a Bruker microTOF-q II mass spectrometer (Bruker Daltonics GmbH, Bremen, Germany).

*B. laterosporus* DSM 25 was cultivated for 1 d in five 2.5 L flasks containing 1.0 L of Modified Tryptic Soy Broth (MTSB, 30 g/L Tryptic Soy Broth, 20.0 g/L starch, 2.0 g/L $MgSO_4$-$7H_2O$, 10.0 g/L $CaCO_3$) at 30° C. for brevicidine production. The culture supernatant was extracted with Diaion® HP-20 (100 g; Sigma-Aldrich) and eluted with 20% IPA (2.0 L), 40% IPA (2.0 L), 60% IPA (2.0 L), and 80% IPA with 0.1% trifluoroacetic acid (1.0 L). All partitions were evaporated to dryness using a vacuum concentrator and dissolved in methanol for HPLC purification. The 60% IPA partition was separated using a semi-preparative RP-HPLC column with a gradient of 20-50% MeCN in water to yield compounds 1, 4-6. *B. laterosporus* ATCC 9141 was cultivated for 2 d in ten 2.5 L flasks containing 1.0 L of MTSB at 27° C. for laterocidine (2) production. The culture supernatant was extracted with Diaion® HP-20 (100 g) and eluted with 20% IPA (2.0 L), 40% IPA (2.0 L), 60% IPA (2.0 L), and 80% IPA with 0.1% trifluoroacetic acid (1.0 L). The last two partitions were evaporated to dryness and loaded into an ODS C-18 column, then eluted with 120 mL of 30%, 50%, 60%, 70%, 80%, 90%, 100% methanol, and 99% methanol supplemented with 1% trifluoroacetic acid. The 50% methanol partition was evaporated to dryness and separated using a semi-preparative RP-HPLC column with a gradient of 20-50% MeCN in water to yield compounds 2, 8-10.

TABLE 4
Compound characterization by MS analysis
| Structure | Compound | MSn fragments |
|---|---|---|
| 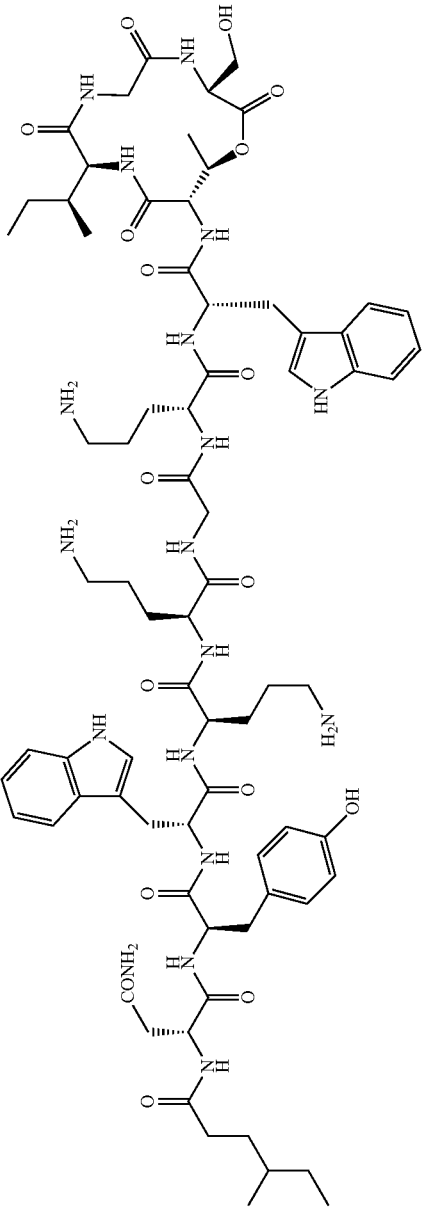 | 1 | [M + 2H]$^{2+}$ 760.4<br>y: 359.3, 545.2, 659.3, 716.3, 830.4, 944.4, 1130.5, 1293.5, 1389.6(−H$_2$O)<br>b: 227.1, 390.3, 576.3, 690.3, 804.4, 861.4, 975.4, 1161.5, 1244.5(−H$_2$O) |
| 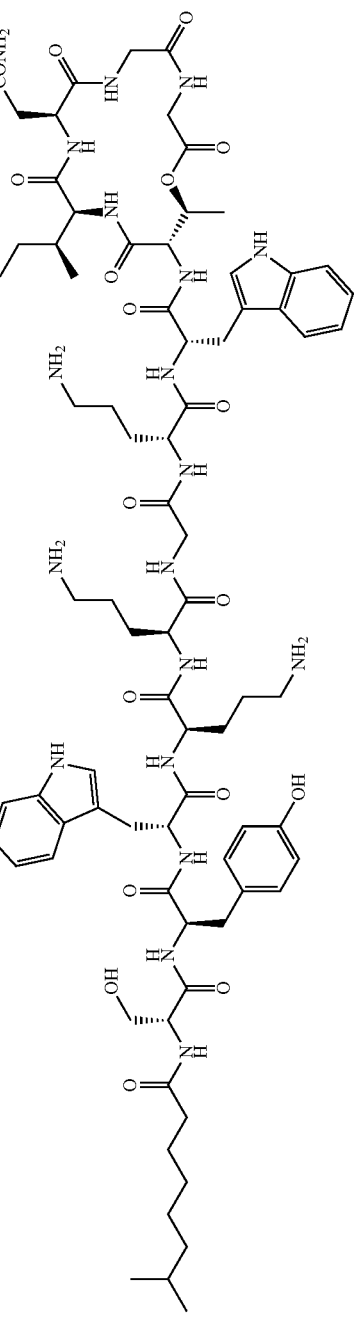 | 2 | [M + 2H]$^{2+}$ 802.9<br>y: 443.3, 629.3, 914.4, 1028.5, 1214.5<br>b: 391.3, 577.3, 691.4, 805.4, 976.5, 1162.5 |

TABLE 4-continued
Compound characterization by MS analysis
| Structure | Compound | MSn fragments |
|---|---|---|
| 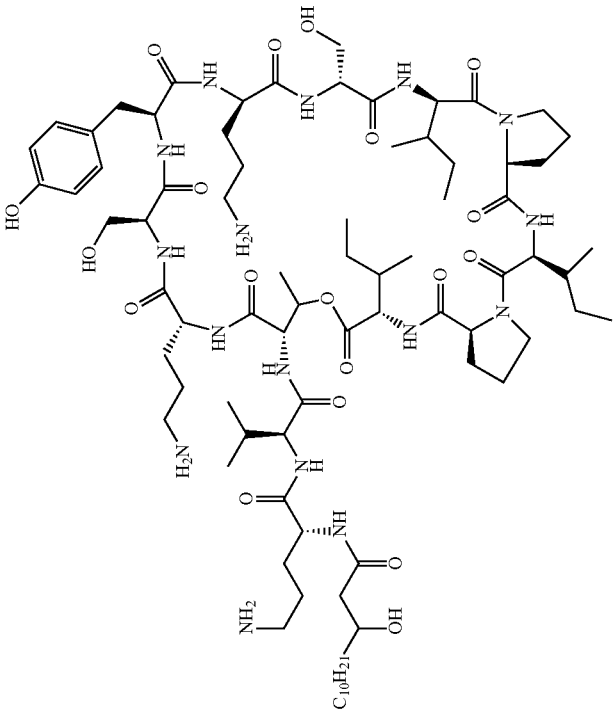 | 3 | $[M + 2H]^{2+}$ 813.5 |
| 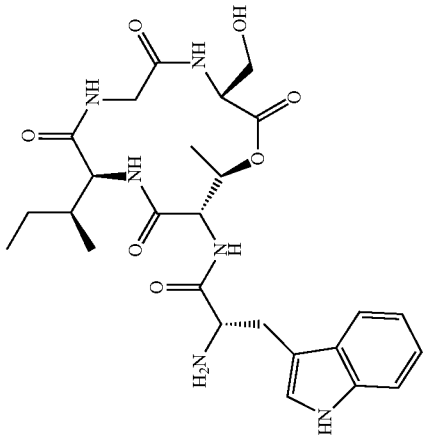 | 4 | $[M + H]^+$ 545.3<br>y: 276.2, 359.2<br>b: 458.3 |

TABLE 4-continued

Compound characterization by MS analysis

| Structure | Compound | MSn fragments |
|---|---|---|
| 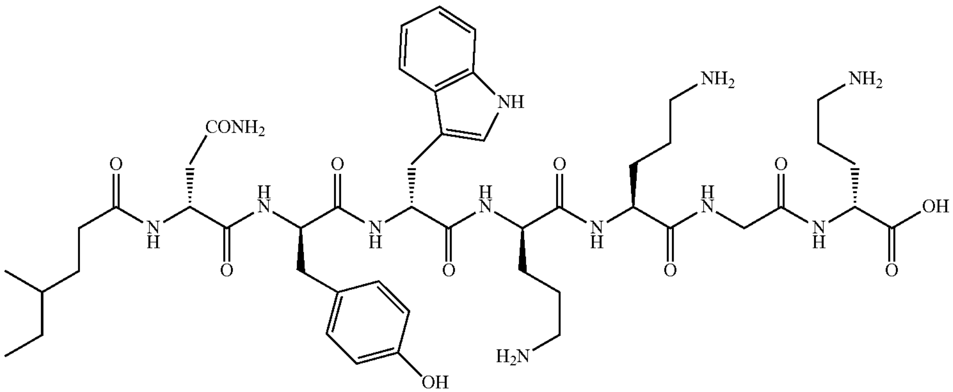 [SMILES: CCC(C)CCC(=O)N[C@H](CC(N)=O)C(=O)N[C@H](Cc1ccc(O)cc1)C(=O)N[C@H](Cc1c[nH]c2ccccc12)C(=O)N[C@H](CCCN)C(=O)N[C@@H](CCCN)C(=O)NCC(=O)N[C@H](CCCN)C(=O)O] | 5 | [M + H]+ 992.54<br>y: 190.1, 304.2, 418.3, 604.4, 767.4, 881.5<br>b: 227.1, 390.2, 576.3, 690.4, 804.5, 861.5 |
| 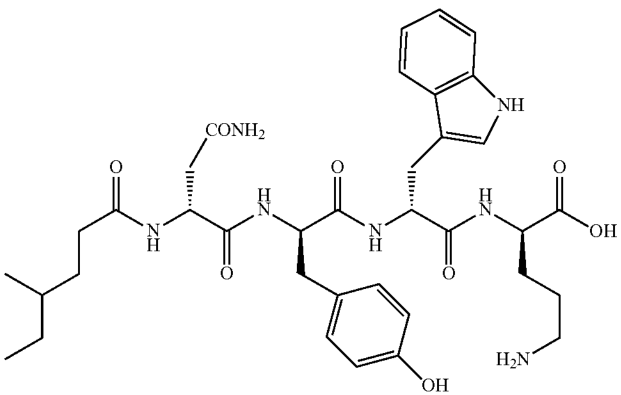 [SMILES: CCC(C)CCC(=O)N[C@H](CC(N)=O)C(=O)N[C@H](Cc1ccc(O)cc1)C(=O)N[C@H](Cc1c[nH]c2ccccc12)C(=O)N[C@H](CCCN)C(=O)O] | 6 | [M + H]+ 707.36<br>y: 319.2, 482.3, 596.3<br>b: 390.2, 576.3 |
| 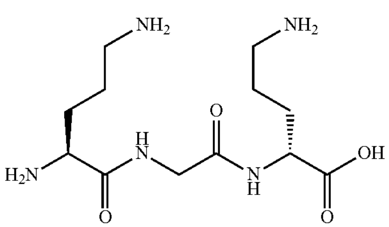 [SMILES: NCCC[C@H](N)C(=O)NCC(=O)N[C@H](CCCN)C(=O)O] | 7 | [M + H]+ 304.2<br>y: 133.1, 190.1<br>b: 115.1, 172.1 |

TABLE 4-continued

Compound characterization by MS analysis

| Structure | Compound | MSn fragments |
|---|---|---|
| 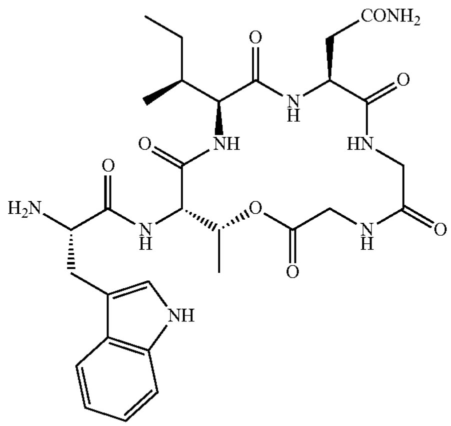 [SMILES: CC[C@H](C)[C@@H]1NC(=O)[C@@H](NC(=O)[C@@H](N)Cc2c[nH]c3ccccc23)[C@@H](C)OC(=O)CNC(=O)CNC(=O)[C@H](CC(N)=O)NC1=O] | 8 | [M + H]+ 629.3<br>b: 515.3, 553.2 |
| 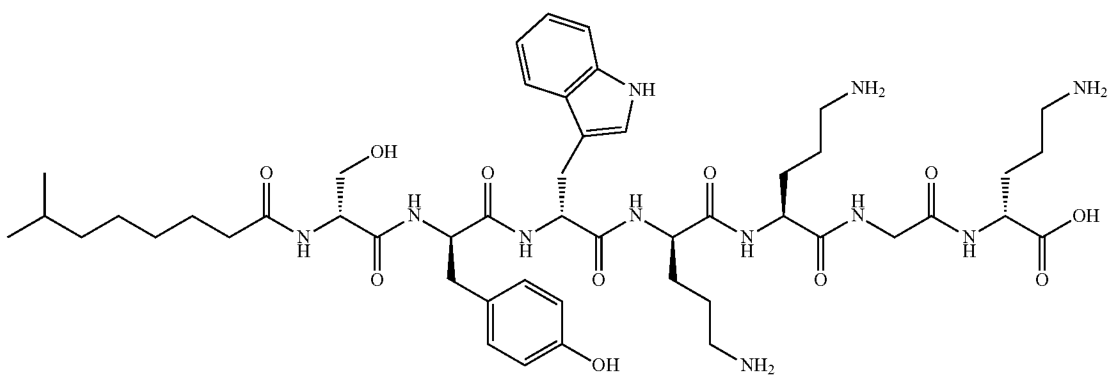 [SMILES: CC(C)CCCCCC(=O)N[C@H](CO)C(=O)N[C@H](Cc1ccc(O)cc1)C(=O)N[C@H](Cc1c[nH]c2ccccc12)C(=O)N[C@H](CCCN)C(=O)N[C@@H](CCCN)C(=O)NCC(=O)N[C@H](CCCN)C(=O)O] | 9 | [M + 2H]$^{2+}$ 497.3<br>y: 190.1, 304.2, 418.3, 604.4, 767.4, 854.4<br>b: 228.2, 391.3, 577.3, 691.4, 805.4 |

TABLE 4-continued

Compound characterization by MS analysis

| Structure | Compound | MSn fragments |
|---|---|---|
| 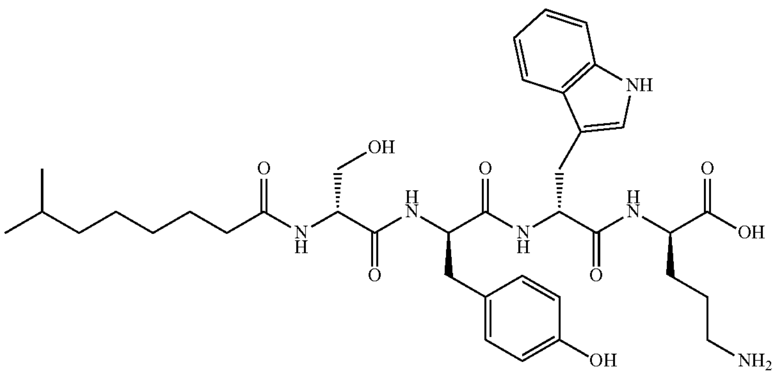 [SMILES: CC(C)CCCCCC(=O)N[C@H](CO)C(=O)N[C@H](Cc1ccc(O)cc1)C(=O)N[C@H](Cc1c[nH]c2ccccc12)C(=O)N[C@H](CCCN)C(=O)O] | 10 | [M + H]+ 709.4 y: 319.2, 482.2, 569.2 b: 391.2, 577.2 |
| 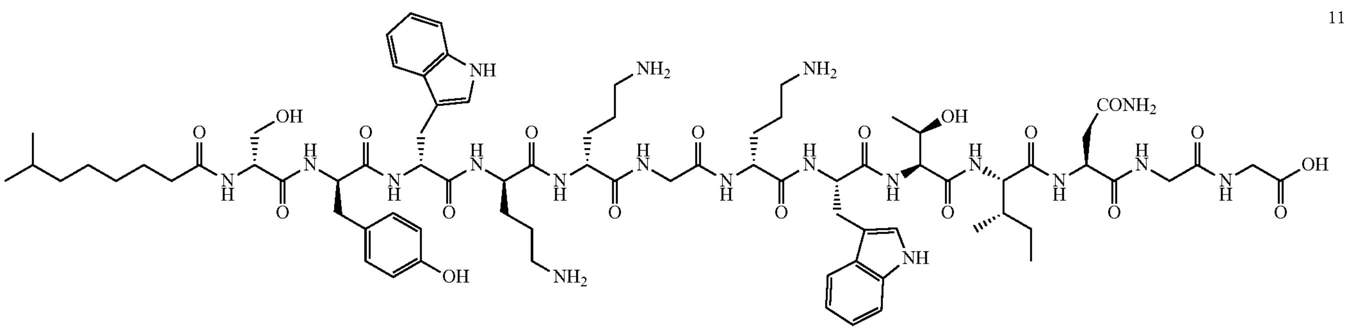 | 11 | [M + 2H]2+ 811.9 y: 247.1, 360.2, 461.2, 761.4, 818.4, 932.4, 1046.5, 1232.5 b: 391.3, 577.3, 691.4, 862.4, 976.5, 1162.5, 1263.5, 1376.6 |

Structure Elucidation $^1$H, $^1$H-$^1$H-COSY, $^1$H-$^{13}$C-HSQC, and $^1$H-$^{13}$C-HMBC NMR spectra for compounds 1, 2, 4 were recorded on a Bruker AV500 spectrometer (500 MHz) using MeOH-d$_4$ (1H-NMR MeOH-d$_4$: $\delta_H$=3.31 ppm; MeOH-d$_4$: $\delta_C$=49.00 ppm). Amino acid configurations of 1-2 were determined using the advanced Marfey's method. To further confirm the amino acid configurations of compounds 1-2, the D-Orn/Lys specific hydrolysis of 1-2 was performed in the 25% phosphate-buffered saline (PBS, pH 7.4, 80 μL) with 100 nM D-Orn/Lys specific peptidase BogQ[36] and 100 μM substrates (1-2) at 37° C. for 2 h. Three volumes of cold methanol (240 μL) were added to samples, which were then incubated at −80° C. for 1 h to precipitate protein. The samples were centrifuged at 15,000 rpm for 10 min, and the supernatant (2 μL) was injected into the same UPLC-MS system described above. The BogQ hydrolyzed fragments of 1 and 2 were purified using the semi-preparative RP-HPLC column with 25% MeCN in water with 0.1% trifluoroacetic acid to yield compounds 4-7 and 7-10. The purified compounds 1-2, 4-10 (0.1-0.2 mg) were hydrolyzed in 6 M HCl at 120° C. overnight. Each solution was evaporated to dryness under a stream of dry N$_2$ and the residue was dissolved in 100 μL of water and divided into two portions. Each portion was treated with 5 μL of NaHCO$_3$ (1M) and 50 μL of 1-fluoro-2,4-dinitrophenyl-5-L-leucinamide (L-FDLA) or D-FDLA (1M) at 40° C. for 2 h. The reaction was quenched with 5 μL of HCl (1M) and diluted with 200 μL of MeOH. The stereochemistry was determined by comparing the L-/D FDLA derivatized samples using UPLC-MS analysis.

TABLE 5

NMR data of brevicidine A (d$_6$-DMSO)

| Position | $^{13}$CNMR | $^1$HNMR |
|---|---|---|
| 1 | 172.0 | |
| 2 | 36.9 | 2.35 (d, 7.0, 15.0), 2.53 m |
| 3 | 49.6 | 4.54, m |
| 3-NH | | 8.02 (d, 8.0) |
| 4 | 172.0 | |
| 5 | 54.8 | 4.27,m |
| 5-NH | | 7.99 (d, 7.5) |
| 6 | 36.1 | 2.61 (dd, 8.0, 14.0), 2.79 m |
| 7 | 127.6 | |
| 8, 12 | 130.0 | 6.85 (2H, d, 8.2) |
| 9, 11 | 114.9 | 6.55 (2H, d, 8.2) |
| 10 | 155.8 | |
| 13 | 171.2 | |
| 14 | 53.9 | 4.49, m |
| 14-NH | | 8.13 (d, 6.5) |
| 15 | 27.2 | 3.17 m, 3.03 (dd, 10.0, 14.5) |
| 16 | 110.1 | |
| 17 | 123.7 | 7.17 brs |
| 18 | 136.1 | |
| 19 | 111.3 | 7.31 (d, 7.9) |
| 20 | 120.9 | 7.07 (t, 7.9) |
| 21 | 118.2 | 6.95 (t, 7.9) |
| 22 | 118.4 | 7.57 (d, 7.9) |
| 23 | 127.3 | |
| 24 | 171.3 | |
| 25 | 51.4 | 4.35, m |
| 25-NH | | 8.06 (d, 7.5) |
| 26 | 29.5 | 1.76, m 1.53, m |
| 27 | 23.6 | 1.54 (2H, m) |
| 28 | 38.5 | 2.78 (2H, m) |
| 28-NH2 | | 7.73 (2H, brs) |
| 29 | 171.5 | |
| 30 | 51.8 | 4.37, m |
| 30-NH | | 7.92 (d, 7.0) |
| 31 | 29.5 | 1.76, m 1.53, m |
| 32 | 23.5 | 1.54 (2H, m) |
| 33 | 38.5 | 2.78 (2H, m) |
| 33-NH2 | | 7.73 (2H, brs) |
| 34 | 171.4 | |
| 35 | 41.7 | 3.74, 3.83 |
| 35-NH | | 8.23 (d, 6.5) |
| 36 | 168.4 | |
| 37 | 51.8 | 4.38, m |
| 37-NH | | 8.11 (d, 6.5) |
| 38 | 29.5 | 1.40, m 1.32, m |
| 39 | 23.3 | 1.31, m |
| 40 | 38.4 | 2.59, m |
| 40-NH2 | | 7.65 (2H, brs) |
| 41 | 171.3 | |
| 42 | 52.9 | 4.73 (dt, 7.5, 6.5) |
| 42-NH | | 8.19 (d, 7.5) |
| 43 | 27.8 | 3.08 (dd, 7.5, 15.0) 2.96 (dd, 7.5, 15.0) |
| 44 | 109.6 | |
| 45 | 124.0 | 7.10 brs |
| 46 | 136.1 | |
| 47 | 111.4 | 7.33 (d, 8.0) |
| 48 | 120.8 | 7.04 (t, 8.0) |
| 49 | 118.3 | 6.98 (t, 8.0) |
| 50 | 118.4 | 7.57 (d, 8.0) |
| 51 | 127.4 | |
| 52 | 170.9 | |
| 53 | 53.9 | 4.55, m |
| 53-NH | | 8.21 (d, 7.5) |
| 54 | 69.8 | 4.90, m |
| 55 | 14.0 | 1.09 (d, 6.5) |
| 56 | 167.0 | |
| 57 | 58.8 | 4.12 (dd, 9.5, 10.5) |
| 57-NH | | 8.53 (d, 9.5) |
| 58 | 34.4 | 1.84, m |
| 59 | 15.4 | 0.84 (d, 7.0) |
| 60 | 24.5 | 1.05 m, 1.51, m |
| 61 | 10.5 | 0.85 (t, 7.5) |
| 62 | 171.1 | |
| 63 | 43.3 | 3.51 (dd, 6.0, 15.0), 3.90 (dd, 6.5, 15.0) |
| 64 | 169.1 | |
| 64-NH | | 7.6 (d, 8.6) |
| 65 | 54.4 | 4.43 (dd, 4.5, 8.0) |
| 66 | 61.3 | 3.60 (dd, 4.5, 12.0), 3.76 (dd, 7.0, 12.0) |
| 67 | 168.9 | |
| F-1 | 172.7 | |
| F-2 | 33.0 | 2.07 t |
| F-3 | 31.8 | 1.26, m 1.50, m |
| F-4 | 33.5 | 1.27, m |
| F-5 | 29.1 | 1.09 m, 1.27, m |
| F-6 | 11.2 | 0.81 (t, 7.5) |
| F-7 | 18.8 | 0.81 (d, 6.5) |

TABLE 6

NMR data of laterocidine (d6-DMSO).

| Position | $^{13}$CNMR | $^1$HNMR |
|---|---|---|
| 1 | 61.3 | 3.50 (2H, m) |
| 1-OH | | 5.13, brs |
| 2 | 54.7 | 4.26 (dt, 6.5, 7.0) |
| 2-NH | | 7.85 (d, 7.5) |
| 3 | 170.7 | |
| 4 | 54.3 | 4.33, m |
| 4-NH | | 8.01 |
| 5 | 35.8 | 2.62, m, 2.82 (dd, 4.0, 14.0) |
| 6 | 127.6 | |
| 7 | 129.8 | 6.89 (d, 8.0) |
| 8 | 114.7 | 6.56 (d, 8.0) |
| 9 | 155.8 | |
| 9-OH | | 9.16 |
| 10 | 114.7 | 6.56 (d, 8.0) |
| 11 | 129.8 | 6.89 (d, 8.0) |

TABLE 6-continued

NMR data of laterocidine (d6-DMSO).

| Position | $^{13}$CNMR | $^1$HNMR |
|---|---|---|
| 12 | 171.2 | |
| 13 | 53.3 | 4.51 (dt, 5.0, 8.0) |
| 13-NH | | 8.0, m |
| 14 | 27.1 | 2.94, m 3.14, m |
| 15 | 109.8 | |
| 16 | 123.5 | 7.14 (d, 8.5) |
| 16-NH | | 10.77 (d, 15.0) |
| 17 | 136 | |
| 18 | 111.1 | 7.32 (t, 8.5) |
| 19 | 120.7 | 7.05, m |
| 20 | 118 | 6.97, m |
| 21 | 118.2 | 7.57 (d, 8.0) |
| 22 | 127.2 | |
| 23 | 171.5 | |
| 24 | 51.2 | 4.41, m |
| 24-NH | | 8.09 (d, 8.0) |
| 25 | 29.1 | 1.51, m 1.70, m |
| 26 | 23.2 | 1.51 (2H, m) |
| 27 | 38.2 | 2.75 (2H, m) |
| 27-NH2 | | 7.76, brs |
| 28 | 171.2 | |
| 29 | 51.2 | 4.39, m |
| 29-NH | | 8.02 |
| 30 | 29.1 | 1.54, m 1.74, m |
| 31 | 23.2 | 1.58 (2H, m) |
| 32 | 38.2 | 2.79 (2H, m) |
| 32-NH2 | | 7.74, brs |
| 33 | 171.4 | |
| 34 | 41.5 | 3.75 (dd, 17.5, 4.0), 3.85 |
| 34-NH | | 8.24, m |
| 35 | 168.3 | |
| 36 | 51.2 | 4.38, m |
| 36-NH | | 8.06 (d, 8.0) |
| 37 | 29.2 | 1.28, m 1.43, m |
| 38 | 22.9 | 1.29 (2H, m) |
| 39 | 38.1 | 2.58 (2H, m) |
| 39-NH2 | | 7.65, m |
| 40 | 171.1 | |
| 41 | 52.7 | 4.75 (dt, 5.5, 8.5) |
| 41-NH | | 8.33, s |
| 42 | 27.1 | 2.94, m 3.14, m |
| 43 | 109.8 | |
| 44 | 123.5 | 7.14 (d, 8.5) |
| 44-NH | | 10.77 (d, 15.0) |
| 45 | 136 | |
| 46 | 111.1 | 7.32 (t, 8.5) |
| 47 | 120.7 | 7.05, m |
| 48 | 118 | 6.97, m |
| 49 | 118.2 | 7.57 (d, 8.0) |
| 50 | 127.2 | |
| 51 | 171.8 | |
| 52 | 53.7 | 4.68 (dd, 3.0, 9.0) |
| 52-NH | | 7.92 (d, 9.0) |
| 53 | 71.7 | 5.17, m |
| 54 | 15.2 | 1.09 (3H, d, 6.5) |
| 55 | 168.7 | |
| 56 | 58.1 | 3.90, m |
| 56-NH | | 8.30, m |
| 57 | 35.5 | 1.57, m |
| 58 | 14.6 | 0.85 (3H, d, 6.5) |
| 59 | 24.9 | 1.15, m 1.55, m |
| 60 | 10.8 | 0.87 (3H, t, 7.5) |
| 61 | 173.2 | |
| 62 | 51.2 | 4.12, m |
| 62-NH | | 9.40 (d, 6.5) |
| 63 | 34.9 | 2.66, m 2.88 (dd, 3.5, 16.5) |
| 64 | 171.9 | |
| 64-NH2 | | 7.74 |
| 65 | 172.8 | |
| 66 | 42.4 | 3.58 (dd, 17.0, 4.0) 4.02 (dd, 17.0, 8.0) |
| 66-NH | | 8.03 |
| 67 | 169.4 | |
| 68 | 40.8 | 3.38, m 4.45 (dd, 10.0, 6.5) |
| 68-NH | | 7.68 |
| 69 | 168.9 | |
| F-1 | 172.7 | |
| F-2 | 34.8 | 2.11 (2H, m) |
| F-3 | 25 | 1.45 (2H, m) |
| F-4 | 28.7 | 1.20 (2H, m) |
| F-5 | 28.7 | 1.23 (2H, m) |
| F-6 | 38.1 | 1.11 (2H, m) |
| F-7 | 27.2 | 1.47, m |
| F-8 | 22.3 | 0.83 (3H, d, 6.5) |
| F-9 | 22.3 | 0.83 (3H, d, 6.5) |

TABLE 7

NMR data of Compound 4 (CD$_3$OD).

| Position | $^{13}$C | $^1$H |
|---|---|---|
| 1 | 54.8 | 4.26 (t, 7.5) |
| 2 | 28.9 | 3.24 (dd, 7, 5, 15.0) 3.39 (dd, 7, 5, 15.0) |
| 3 | 107.8 | |
| 4 | 125.9 | 7.21 brs |
| 5 | 138.5 | |
| 6 | 112.7 | 7.38 (d, 8.0) |
| 7 | 122.9 | 7.13 (t, 8.0) |
| 8 | 120.4 | 7.06 (t, 8.0) |
| 9 | 118.4 | 7.62 (d, 8.0) |
| 10 | 128.4 | |
| 11 | 170.1 | |
| 12 | 55.9 | 4.67, (d, 5.1) |
| 13 | 71.9 | 5.22, (q, 6.4) |
| 14 | 14.7 | 1.25 (d, 6.4, 3H) |
| 14 | 14.7 | 1.25 (d, 6.4, 3H) |
| 15 | 169.3 | |
| 16 | 59.9 | 4.22 (dd, 9.5, 10.5) |
| 16-NH | | 8.60 (d, 9.6) |
| 17 | 35.8 | 1.94, m |
| 18 | 15.8 | 0.93 (d, 6.7) |
| 19 | 24.9 | 1.16 m, 1.62, m |
| 20 | 11.2 | 0.95 (t, 7.4) |
| 21 | 174.7 | |
| 22 | 44.7 | 3.37 (d, 14.7), 4.37 (d, 14.7) |
| 23 | 171.9 | |
| 24 | 54.4 | 4.50 (dd, 4.9, 3.7) |
| 25 | 62.9 | 3.97 (dd, 3.6, 11.0), 3.82 (dd, 4.0, 11.0) |
| 26 | 170.4 | |

Antibacterial Assays

Minimum inhibitory concentration (MIC) was determined by broth microdilution according to CLSI guidelines. The test medium for most species was Mueller-Hinton broth (MHB). Bacteria were grown overnight to early stationary phase and adjusted in MHB to $5.0 \times 10^5$ colony-forming units per mL (c.f.u./mL) in the wells of 96-well microtiter plates, mixed with varying concentrations of test compounds and incubated at 37° C. for 24 h. Cell growth was evaluated by measuring the optical density at 595 nm (Thermo Scientific Multiskan FC multiplate photometer) (Waltham, Mass., USA), and the lowest compound concentrations, which displayed no bacterial growth, were defined as the MIC. MHBs containing 10% fetal bovine serum (Gibco), 21 mM MgCl, or 1.0 mg/ml LPS (lipopolysaccharides from *Escherichia coli* O55:B5, Sigma-Aldrich) were used to test their inhibitory effects.

Bacterial Growth Kinetics and Time-Kill Assay

A fresh single colony of *E. coli* Top10 was inoculated into MHB (5 mL) and grown with shaking at 225 rpm overnight.

The bacteria were diluted to $1\times10^5$ c.f.u./mL in fresh MHB, grown overnight to early log-phase (OD=0.15) and treated with the antibiotics of interest in the wells of a 96-well plate. Final antibiotic concentrations varied from 1×MIC to 8×MIC. The plate was then incubated at 30° C. overnight, with OD 600 measurements taken every 30 seconds.

An overnight culture of *E. coli* Top10 or *Pseudomonas aeruginosa* PAO1 cells was diluted 1:10,000 in MHB and incubated at 37° C. with agitation at 180 rpm for 2 h (early exponential). The bacteria were then challenged with antibiotics at 10×MIC, brevicidine (20 μg/ml), laterocidine (20 μg/ml) or polymyxin B (10 μg/ml) at room temperature without shaking. An untreated sample of cells was used as a negative control. At intervals, 10 μL aliquots were removed, centrifuged at 10,000 g for 1 min and resuspended in 1.0 mL of sterile PBS. Tenfold-serially-diluted suspensions were plated on MHB agar plates and incubated at 37° C. overnight. Colonies were counted and the number of c.fu. per mL was calculated. For analysis of lysis, 300 μL of culture (OD600=1.0) were treated with 10×MIC of antibiotics for 24 h. Experiments were performed in triplicate.

Resistance Studies

*Escherichia coli* ATCC 25922 was inoculated into MHB overnight at 37° C. with continuous shaking. Cells were diluted 10,000 times in MHB to about $1\times10^6$ c.f.u./mL. 10 μL aliquots were drawn to a 96-well plate containing 90 μL of serial diluted brevicidine, laterocidine, and ciprofloxacin, at final concentrations of 0.25×, 0.5×, 1×, 1.5×, 2× and 4×MIC. Plates with bacteria were incubated at 37° C. without shaking. After 24 h, the MIC was recorded, and 1 μL aliquots from the culture with the second highest antibiotic concentration that showed visible growth were diluted 1,000 times in MHB for the subsequent assay. This process was repeated for 30 d, and the final MIC was confirmed by the same antibacterial assay described above. The experiment was performed in quadruplicate, and on each day, the sample that developed the highest resistance was measured to plot the curve.

Cytotoxicity and Hemolytic Activity

Human HeLa cells were used in the assay. 90 μL of $1\times10^5$/mL cells were placed into the wells of 96-microwell plates. After 12 h, 10 μL of a medium containing test compounds at various concentrations were added and incubated at 37° C. for 48 h. Afterwards, the supernatant was removed and 20 μL of MTT (2.5 mg mL$^{-1}$) in 1×PBS were added to each well. After incubation at 37° C. for 3 h, 80 μL of dimethyl sulfoxide (DMSO) were added to each well and incubated for an additional 15 min. The absorbance was then measured at 570 nm with a Thermo Scientific Multiskan FC multiplate photometer.

Hemolytic activity was determined with rabbit red blood cells freshly isolated from the blood of healthy rabbits. Brevicidine and laterocidine were added at final concentrations of 128, 64, 32 and 16 μg mL$^{-1}$ in 0.5% DMSO to 2% (v/v) erythrocytes in 1×PBS. The cells were incubated for 1 h at 37° C. and centrifuged for 5 min at 10,000 g. The supernatant was transferred to a 96-well plate and the absorbance was measured at a wavelength of 570 nm with a Thermo Scientific Multiskan FC multiplate photometer. The absorbance relative to the positive control which was treated with 10% Triton X-100 was defined as the percentage of hemolysis.

LPS Binding Determined by LTC

Microcalorimetric experiments of peptide binding to LPS were performed on an MCS isothermal titration calorimeter (ITC) (Microcal, Northampton, Mass.) at 37° C. LPS was prepared as a 50 μM aqueous suspension in 20 mM HEPES (pH 7.0) buffer by suspension, sonication and temperature cycling between 5° C. and 70° C. This suspension was stored at 4° C. overnight prior to use. 100 μM peptide solutions (brevicidine and polymyxin B) were prepared in the same buffer and all solutions were degassed prior to use by stirring under vacuum for 5 min at 37° C. After thermal equilibration, 5 μL aliquots of the peptide solution were added every 3 min into the lipid-containing cell at 37° C. and stirred constantly. The change in heat during the titration steps was registered in real time and raw data were processed using the Origin® 7 software provided with the instrument. In control experiments, the corresponding peptide solution (or LPS solution) was injected into the buffer without LPS (or without peptide). Heats of dilution were significantly lower than those during ligand-receptor binding.

Atomic Force Microscopy Imaging of Bacterial Cells

One hundred μL of log-phase *E. coli* ATCC 25922 cells (OD600=0.2) in an LB medium were incubated for 1.5 h at 37° C. with or without tested compounds at 10×MIC. The samples were then centrifuged at 8000 g for 10 min at 4° C., and the pellet was washed twice in 100 lpL of apyrogenic water. The bacteria resuspended in 50 μL of apyrogenic water were applied to mica disks and dried overnight at 28° C. before imaging. Atomic force micrographs were recorded on a Veeco Mulitmode AFM with NanoScope III controller operating in contact mode. The data were analyzed with NanoScope Analysis software v.1.40 (Veeco, USA). Scans were acquired at 25° C. at the rates of 1.0 Hz and 256 samples per line resolution. Downstream image processing and analysis were performed using NanoScope software (Bruker). Height images were flattened to compensate for cell curvature, and topographical sections were used to generate two-dimensional reconstructions of surface texture.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Mouse Thigh Infection Model

In vivo activities of brevicidine and laterocidine were tested using the mouse thigh infection model. Animal studies were performed by Pharmacology Discovery Services Taiwan Ltd. (Taipei, Taiwan) in general accordance with standard guidelines on animal welfare in an AAALAC-accredited facility. The protocol was reviewed and approved by the Institutional Animal Care and Use Committee. Groups of five female specific-pathogen-free ICR (CD-1) mice weighing 22±2 g (~5 weeks of age) were used. Animals were immunosuppressed with two intraperitoneal injections of cyclophosphamide, the first at 150 mg/kg 4 d before infection (day −4) and the second at 100 mg/kg 1 d before infection (day −1). On day 0, animals were inoculated intramuscularly (0.1 ml/thigh) in the right thigh with an *E. coli* ATCC 25922 suspension. Vehicle (10% DMSO, 1% Tween 80, 0.9% NaCl) and antibiotics were then subcutaneously injected 2 h and 8 h later. Due to limited amount of compounds 1-2, only one concentration of 1(30 mg/kg) or 2 (15 mg/kg) was used in this study. At 26 h after inoculation, animals were euthanized by $CO_2$ asphyxiation before the muscle of the right thigh was harvested from each test animal. The removed muscle was homogenized in 5 mL of PBS, pH 7.4, with a polytron homogenizer. Homogenates in the amount of 0.1 mL were used for serial tenfold dilutions and plated onto a nutrient agar medium for colony count (c.f.u./g) determination.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Laxminarayan, R. et al. Antibiotic resistance—the need for global solutions. *Lancet Infect. Dis.* 13, 1057-1098 (2013).
2. Boucher, H. W. et al. Bad bugs, no drugs: no ESKAPE! An update from the Infectious Diseases Society of America. *Clin. Infect. Dis.* 48, 1-12 (2009).
3. Fischbach, M. A. & Walsh, C. T. Antibiotics for emerging pathogens. *Science* 325, 1089-1093 (2009).
4. Lewis, K. Platforms for antibiotic discovery. *Nat. Rev. Drug Discov.* 12, 371-387 (2013).
5. Yeung, A. T. Y., Gellatly, S. L. & Hancock, R. E. W. Multifunctional cationic host defence peptides and their clinical applications. *Cell. Mol. Life Sci.* 68, 2161-2176 (2011).
6. Hancock, R. E. W. & Lehrer, R. Cationic peptides: a new source of antibiotics. *Trends Biotechnol.* 16, 82-88 (1998).
7. Epand, R. M. & Vogel, H. J. Diversity of antimicrobial peptides and their mechanisms of action. *Biochim. Biophys. Acta, Biomembr.* 1462, 11-28 (1999).
8. Marr, A. K., Gooderham, W. J. & Hancock, R. E. W. Antibacterial peptides for therapeutic use: obstacles and realistic outlook. *Curr. Opin. Pharmacol.* 6, 468-472 (2006).
9. Hancock, R. E. W. & Sahl, H. G. Antimicrobial and host-defense peptides as new anti-infective therapeutic strategies. *Nat. Biotechnol.* 24, 1551-1557 (2006).
10. Blin, K., Medema, M. H., Kottmann, R., Lee, S. Y. & Weber, T. The antiSMASH database, a comprehensive database of microbial secondary metabolite biosynthetic gene clusters. *Nucleic Acids Res.* 45, D555-D559 (2017).
11. Kosikowska, P. & Lesner, A. Antimicrobial peptides (AMPs) as drug candidates: a patent review (2003-2015). *Expert Opin. Ther. Pat.* 26, 689-702 (2016).
12. Fjell, C. D., Hiss, J. A., Hancock, R. E. W. & Schneider, G. Designing antimicrobial peptides: form follows function. *Nat. Rev. Drug Discov.* 11, 37-51 (2012).
13. Mahlapuu, M., Hakansson, J., Ringstad, L. & Bjorn, C. Antimicrobial peptides: an emerging category of therapeutic agents. *Front. Cell. Infect. Microbiol.* 6, 194 (2016).
14. Law, V. et al. DrugBank 4.0: shedding new light on drug metabolism. *Nucleic Acids Res.* 42, D1091-D1097 (2014).
15. Gordon, Y. J., E. G. & McDermott, A. M. A review of antimicrobial peptides and their therapeutic potential as anti-infective drugs. *Curr. Eye Res.* 30, 505-515 (2005).
16. Clardy, J., Fischbach, M. A. & Walsh, C. T. New antibiotics from bacterial natural products. *Nat. Biotechnol.* 24, 1541-1550 (2006).
17. Schwarzer, D., Finking, R. & Marahiel, M. A. Nonribosomal peptides: from genes to products. *Nat. Prod. Rep.* 20, 275-287 (2003).
18. Crosa, J. H. & Walsh, C. T. Genetics and assembly line enzymology of siderophore biosynthesis in bacteria. *Microbiol. Mol. Biol. Rev.* 66, 223-249 (2002).
19. Gerlt, J. A. et al. Enzyme Function Initiative-Enzyme Similarity Tool (EFI-EST): A web tool for generating protein sequence similarity networks. *Biochim. Biophys. Acta, Proteins Proteomics* 1854, 1019-1037 (2015).
20. Cochrane, S. A. & Vederas, J. C. Lipopeptides from *Bacillus* and *Paenibacillus* spp.: a gold mine of antibiotic candidates. *Med. Res. Rev.* 36, 4-31 (2016).
21. Huang, E. & Yousef, A. E. The lipopeptide antibiotic paenibacterin binds to the bacterial outer membrane and exerts bactericidal activity through cytoplasmic membrane damage. *Appl. Environ. Microbiol.* 80, 2700-2704 (2014).
22. Liu, Y. Y. et al. Emergence of plasmid-mediated colistin resistance mechanism MCR-1 in animals and human beings in China: a microbiological and molecular biological study. *Lancet Infect. Dis.* 16, 161-168 (2016).
23. Cochrane, S. A. et al. Antimicrobial lipopeptide tridecaptin A1 selectively binds to Gram-negative lipid II. *Proc. Natl. Acad. Sci. U.S.A* 113, 11561-11566 (2016).
24. Trimble, M. J., Mlynarcik, P., Kolar, M. & Hancock, R. E. W. Polymyxin: alternative mechanisms of action and resistance. *Cold Spring Harb. Perspect. Med.* 6 (2016).
25. Chu, J. et al. Discovery of MRSA active antibiotics using primary sequence from the human microbiome. *Nat. Chem. Biol.* 12, 1004-1006 (2016).
26. Gross, H. & Loper, J. E. Genomics of secondary metabolite production by *Pseudomonas* spp. *Nat. Prod. Rep.* 26, 1408-1446 (2009).
27. Bode, H. B. Entomopathogenic bacteria as a source of secondary metabolites. *Curr. Opin. Chem. Biol.* 13, 224-230 (2009).
28. Moon, S. H. et al. Novel linear lipopeptide paenipeptins with potential for eradicating biofilms and sensitizing Gram-negative bacteria to rifampicin and clarithromycin. *J. Med. Chem.* 60, 9630-9640 (2017).
29. Vaara, M. et al. A novel polymyxin derivative that lacks the fatty acid tail and carries only three positive charges has strong synergism with agents excluded by the intact outer membrane. *Antimicrob. Agents Chemother.* 54, 3341-3346 (2010).
30. Forst, S., Dowds, B., Boemare, N. & Stackebrandt, E. *Xenorhabdus* and *Photorhabdus* spp.: bugs that kill bugs. *Annu. Rev. Microbiol.* 51, 47-72 (1997).
31. Fuchs, S. W. et al. Neutral loss fragmentation pattern based screening for arginine-rich natural products in *Xenorhabdus* and *Photorhabdus*. *Anal. Chem.* 84, 6948-6955 (2012).

32. Stokes, J. M. et al. Pentamidine sensitizes Gram-negative pathogens to antibiotics and overcomes acquired colistin resistance. *Nat. Microbial.* 2, 17028 (2017).
33. Weber, T. et al. AntiSMASH 3.0-a comprehensive resource for the genome mining of biosynthetic gene clusters. *Nucleic Acids Res.* 43, W237-W243 (2015).
34. Smoot, M. E., Ono, K., Ruscheinski, J., Wang, P. L. & Ideker, T. Cytoscape 2.8: new features for data integration and network visualization. *Bioinformatics* 27, 431-432 (2010).
35. Fujii, K., Ikai, Y., Oka, H., Suzuki, M. & Harada, K. A nonempirical method using LC/MS for determination of the absolute configuration of constituent amino acids in a peptide: Combination of Marfey's method with mass spectrometry and its practical application. *Anal. Chem.* 69, 5146-5151 (1997).
36. Li et al. Resistance to nonribosomal peptide antibiotics mediated by D-stereospecific peptidase. *Nat. Chem. Biol.* Accepted.
37. Odds, F. C. Synergy, antagonism, and what the chequerboard puts between them. *J. Antimicrob. Chemother.* 52, 1 (2003).
38. DeRyke, C. A., Banevicius, M. A., Fan, H. W., & Nicolau, D. P. (2007). Bactericidal activities of meropenem and ertapenem against extended-spectrum-3-lactamase-producing *Escherichia coli* and *Klebsiella pneumoniae* in a neutropenic mouse thigh model. *Antimicrob. Agents Chemother.* 51(4), 1481-1486.
39. National Research Council. Guide for the care and use of laboratory animals. National Academies Press (2010).

We claim:

1. A pharmaceutical composition comprising a cationic nonribosomal peptide (CNRP) salt, wherein the CNRP comprises a hydrophobic N-terminal fatty acid chain, a linear cationic segment, and a hydrophobic tear peptide or pentapeptide ring, and the salt is:
   i) with an acid selected from hydrobromic acid, perchloric acid, nitric acid, thiocyanic acid, sulfuric acid, phosphoric acid, trifluoroacetic acid (TFA), cyclopentanepropionic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, 3-phenylpropionic acid, lauryl sulfuric acid, and hydroxynaphthoic acid; or
   ii) with a base selected from sodium hydroxide, ammonium hydroxide, potassium hydroxide, monoalkyl amine, dialkyl amine, trialkyl amine, and aryl amine.

2. The pharmaceutical composition of claim 1, further comprising a pharmaceutically acceptable carrier or excipient.

3. The pharmaceutical composition of claim 1, wherein the CNRP is brevicidine (SEQ ID NO: 1) or laterocidine (SEQ ID NO: 2).

4. A method of treating a bacterial infection, comprising administering to a subject in need thereof, the pharmaceutical composition of claim 1.

5. The method of claim 4, wherein the bacterium is a Gram-negative bacterium resistant to an antibiotic selected from an aminoglycoside, carbapenem, monobactam, colistin, cephalosporin, penicillin, macrolide, quinolone, sulfonamide/thrimethoprim, and chloramphenicol.

6. The method of claim 4, wherein the bacterium is a Gram-negative bacterium belonging to a genus selected from *Acinetobacter, Actinobacillus, Bordetella, Brucella, Campylobacter, Cyanobacteria, Enterobacter, Erwinia, Escherichia, Franeiscella, Helicobacter, Hemophilus, Klebsiella, Legionella, Moraxella, Neisseria, Pasteurella, Proteus, Pseudomonas, Salmonella, Serratia, Shigella, Treponema, Vibrio,* and *Yersinia*.

* * * * *